US008778945B2

(12) United States Patent
Hergenrother et al.

(10) Patent No.: US 8,778,945 B2
(45) Date of Patent: Jul. 15, 2014

(54) DESIGN, SYNTHESIS AND EVALUATION OF PROCASPASE ACTIVATING COMPOUNDS AS PERSONALIZED ANTI-CANCER DRUGS

(75) Inventors: Paul Joseph Hergenrother, Champaign, IL (US); Quinn Patrick Peterson, Savoy, IL (US); Danny Chung Hsu, Urbana, IL (US); Diana C. West, Champaign, IL (US); Timothy M. Fan, Mahomet, IL (US); Chris J. Novotny, Naperville, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 43 days.

(21) Appl. No.: 13/148,350

(22) PCT Filed: Feb. 9, 2010

(86) PCT No.: PCT/US2010/023543
§ 371 (c)(1),
(2), (4) Date: Nov. 2, 2011

(87) PCT Pub. No.: WO2010/091382
PCT Pub. Date: Aug. 12, 2010

(65) Prior Publication Data
US 2012/0040995 A1  Feb. 16, 2012

Related U.S. Application Data

(60) Provisional application No. 61/151,064, filed on Feb. 9, 2009.

(51) Int. Cl.
*A61K 31/495* (2006.01)
*C07D 295/104* (2006.01)

(52) U.S. Cl.
USPC ..................... 514/252.12; 544/400

(58) Field of Classification Search
None
See application file for complete search history.

(56) References Cited

U.S. PATENT DOCUMENTS

| 3,702,879 | A | 11/1972 | Hellmut et al. |
| 3,847,866 | A | 11/1974 | Iliopulos et al. |
| 3,879,498 | A | 4/1975 | Iliopulos et al. |
| 4,463,159 | A | 7/1984 | Besecke et al. |
| 5,569,673 | A | 10/1996 | Morre et al. |
| 6,303,329 | B1 | 10/2001 | Heinrikson et al. |
| 6,403,765 | B1 | 6/2002 | Alnemri |
| 6,444,638 | B2 | 9/2002 | Schwartz et al. |
| 6,489,476 | B1 | 12/2002 | Dang et al. |
| 6,534,267 | B1 | 3/2003 | Wang et al. |
| 6,548,536 | B2 | 4/2003 | Hara et al. |
| 6,558,900 | B2 | 5/2003 | Wang et al. |
| 6,605,589 | B1 | 8/2003 | Uckun et al. |
| 6,608,026 | B1 | 8/2003 | Wang et al. |
| 6,627,623 | B2 | 9/2003 | Ho et al. |
| 6,762,045 | B2 | 7/2004 | Krebs et al. |
| 6,878,743 | B2 | 4/2005 | Choong et al. |
| 7,041,784 | B2 | 5/2006 | Wang et al. |
| 7,053,071 | B2 | 5/2006 | Dawson et al. |
| 7,632,972 | B2 | 12/2009 | Hergenrother et al. |
| 2003/0032045 | A1 | 2/2003 | Wang et al. |
| 2003/0148966 | A1 | 8/2003 | Jayaram et al. |
| 2003/0198949 | A1 | 10/2003 | Goldmakher et al. |
| 2004/0077542 | A1 | 4/2004 | Wang et al. |
| 2004/0180828 | A1 | 9/2004 | Shi |
| 2005/0197511 | A1 | 9/2005 | Hergenrother et al. |
| 2007/0049602 | A1 | 3/2007 | Hergenrother et al. |
| 2011/0257398 | A1 * | 10/2011 | Fako et al. ................... 544/357 |
| 2012/0040995 | A1 | 2/2012 | Hergenrother et al. |

FOREIGN PATENT DOCUMENTS

| WO | WO 02/083114 | 10/2002 |
| WO | WO 2005/044191 | 5/2005 |
| WO | WO 2005/090370 | 9/2005 |
| WO | WO 2006/128173 | 11/2006 |
| WO | WO 2007/008529 | 1/2007 |
| WO | WO 2008/134474 | 11/2008 |
| WO | WO 2008134474 A2 * | 11/2008 |
| WO | WO 2010/091382 | 8/2010 |

OTHER PUBLICATIONS

Peterson, Q.P., et al. "Procaspase-3 Activation as an Anti-Cancer Strategy: Structure-Activity Relationship of Procaspase-Activating Compound I (PAC-1) and Its Cellular Co-Localization with Caspase-3." J. Med. Chem. (2009), vol. 52, pp. 5721-5731.*
CAS Registry. American Chemical Society. STN CAS Registry Database.*
American Cancer Society (ACS). "Cancer Types." © 2013. Available from: < http://www.cancer.org/cancer/showallcancertypes/index >.*
Navigating Cancer and Blood Disorders. "List of Cancer Chemotherapy Drugs." © 2013. Available from: < https://www.navigatingcancer.com/library/all/chemotherapy_drugs >.*
Fulda, S., et al. "Caspase Activation in Cancer Therapy." National Library of Medicine, National Institutes of Health. © 2000. Available from: < https://www.navigatingcancer.com/library/all/chemotherapy_drugs >.*
American Chemical Society (ACS). STN Chemical Abstract Service (CAS) RN database. © 2013.*
T. Bunyapaiboonsri et al., "Generation of Bis-Cationic Heterocyclic Inhibitors of *Bacillus subtilis* HPr Kinase/Phosphatase from a Ditopic Dynamic Combinatorial Library," J. Med. Chem. 46:5803-5811, 2003.
A. Ling et al., "Identification of Alkylidene Hydrazides as Glucagon Receptor Antagonists," J. Med. Chem. 44:3141-3149, 2001.
Q. Peterson et al., "Procaspase-3 Activation as an Anti-Cancer Strategy: Structure-Activity Relationship of Procaspase-Activating Compound 1 (PAC-1) and its Cellular Co-Localization with Caspase-3," J. Med. Chem. 52:5721-5731, 2009.

(Continued)

*Primary Examiner* — Noble Jarrell
*Assistant Examiner* — John S Kenyon
(74) *Attorney, Agent, or Firm* — Haukaas Fish PLLC; Michael H. Haukaas

(57) ABSTRACT

Compositions and methods are disclosed in embodiments relating to induction of cell death such as in cancer cells. Compounds and related methods for synthesis and use thereof, including the use of compounds in therapy for the treatment of cancer and selective induction of apoptosis in cells are disclosed. Compounds are disclosed that have lower neurotoxicity effects than other compounds.

16 Claims, 24 Drawing Sheets

(56) References Cited

OTHER PUBLICATIONS

A. Silva et al., "Synthesis and Vasodilatory Activity of New N-acylhydrazone Derivatives, Designed as LASSBio-295 Analogues," *Bioorganic & Medicinal Chemistry* 13:3431-3437, 2005.

M. Tiecco et al., "Factors Controlling the Selenium-Induced Cyclizations of Alkenyl Hydrazines to Pyridazine or Pyrrolidinamine Derivatives," *Tetrahedron* 53(30):10591-10602, 1997.

Adjei et al. (2003) "Novel Anticancer Agents in Clinical Development," *Cancer Biol. Ther.* S1:S5-S15.

Adler et al. (1997) "Protection by the Heavy Metal Chelator N,N,N',N'-Tetrakis (2-Pyridylmethyl)ethylenediamine (TPEN) Against the Lethal Action of Botulinum Neurotoxin A and B," *Toxicon* 35(7):1089-1100.

Aiuchi et al. (1998) "Zinc Ions Prevent Processing of Caspase-3 During Apoptosis Induced by Geranylgeraniol in HL-60 Cells," *J. Biochem*. 124:300-303.
Alley et al. (Feb. 1, 1988) "Feasibility of Drug Screening with Panels of Human Tumor Cell Lines Using a Microculture Tetrazolium Assay," *Cancer Res*. 48:589-601.
Anderson et al. (1996) "A Phase I Study of a 24 Hour Infusion of Gemcitabine in Previously Untreated Patients with Inoperable Non-Small-Cell Lung Cancer," *Br J Cancer* 74:460-462.
Becattini et al. (2004) "Rational Design and Real Time, In-Cell Detection of the Proapoptotic Activity of a Novel Compound Targeting Bcl-XL," *Chem. Biol*. 11:389-395.
Beyersmann et al. (2001) "Functions of Zinc in Signaling, Proliferation and Differentiation of Mammalian Cells," *BioMetals* 14:331-341.
Bhattacharya et al. (1981) "The Michaelis-Arbuzov Rearrangement," *Chem. Rev*. 81:415-430.
Blake et al. (Jun. 1997) "Estrogen Can Protect Splenocytes from the Toxic Effects of the Environmental Pollutant 4-*tert*-Octylphenol," *Endocrine* 6:243-249.
Blatt et al. (2001) "Signaling Pathways and Effector Mechanisms Pre-Programmed Cell Death," *Bioorg. Med. Chem. Lett*. 9:1371-1384.
Boatright et al. (2003) "Mechanisms of Caspase Activation," *Curr. Opin. Cell. Biol*. 15:725-731.
Boisselle et al. (1962) "Acetylene-Allene Rearrangements. Reactions of Trivalent Phosphorous Chlorides with Alpa-Acetylenic Alcohols and Glycols," *J. Org. Chem*. 27(5):1828-1833.
Bose et al. (2003) "An Uncleavable Procaspase-3 Mutant has a Lower Catalytic Efficiency but an Active Site Similar to that of Mature Caspase-3," *Biochemistry* 42:12298-12310.
Boyd et al. (1995) "Some Practical Considerations and Applications of the National Cancer Institute in Vitro Anticancer Drug Discovery Screen," *Drug Dev. Res*. 34:91-109.
Breen et al. (2008) "Evolutionarily Conserved Cytogenetic Changes in Hematological Malignancies of Dogs and Humans—Man and his Best Friend Share More than Companionship," *Chromosome Res*. 16:145-154.
Buckley et al. (Feb. 11, 1999) "RGD Peptides Induce Apoptosis by Direct Caspase-3 Activation," *Nature* 397:534-539.
Bundgaard, H. (1985) "Design of Prodrugs," *Methods Enzymol*. 42:309-396.
Bundgaard, (1988) "Glycolamide Esters as Biolabile Prodrugs of Carboxylic Acid Agents: Synthesis, Stability, Bioconversion, and Physicochemical Properties," J. Pharm. Sci. 77(4):285-298.
Bundgaard, H. (1991) "Design and Application of Prodrugs," In; *A Textbook of Drug Design and Development*, Krosgaard et al. eds., Ch. 5, pp. 113-191.
Bundgaard, H. (1992) "(C) Means to Enhance Penetration: (1) Prodrugs as a Means to Improve the Delivery of Peptide Drugs," *Adv. Drug Deliv. Rev*. 8:1-38.
Cannon-Albright et al. (Nov. 13, 1992) "Assignment of a Locus for Familial Melanoma, MLM, to Chromosome 9p13-p22," *Science* 258:1148-1152.
Chai et al. (1999) "Regulation of Caspase Activation and Apoptosis by Cellular Zinc Fluxes and Zinc Depreciation: A Review," *Immunol. Cell Biol*. 77:272-278.
Charkoudian et al. (2006) "A Pro-Chelator Triggered by Hydrogen Peroxide Inhibits Iron-promoted Hydroxyl Radical Formation," *J. Am. Chem. Soc*. 128:12424-12425.
Chemical Abstracts Service Accession No. 488086-61-9, Abstract, Feb. 10, 2003.
Chemical Abstracts Service Accession No. 315198-34-6, Abstract, Jan. 19, 2001.
Chimienti et al. (2001) "Role of Cellular Zinc in Programmed Cell Death: Temporal Relationship Between Zinc Depletion, Activaition of Caspases, and Cleavage of Sp Family Transcription Factors," *Biochem. Pharmacol*. 62:51-62.
Chun et al. (2000) "Evaluation of a High-Dose Chemotherapy Protocol with no Maintenance Therapy for Dogs with Lymphoma," *J. Vet. Intern. Med*. 14:120-124.
Ciardiello et al. (2000) "Antitumor Effect and Potentiation of Cytotoxic Drugs Activity in Human Cancer Cells by ZD-1839 (Iressa), an Epidermal Growth Factor Receptor-selective Tyrosine Kinase Inhibitor," *Clinical Cancer Research* 6:2053-2063.
Clark, D.E. (2003) "Silico Prediction of Blood-Brain Barrier Permeation," *Drug Discov Today* 8(20):927-933.
Cossarizza et al. (2001) "Analysis of Mitochondria During Cell Death," *Methods Cell Biol*. 63:467-486.
Dauzonne et al. (1997) "Synthesis and in Vitro Cytotoxicity of a Series of 3-Aminoflavones," *Eur. J. Med. Chem*. 32(1):71-82.
De Graaff et al. (1999) "In Vitro Antagonistic Cytotoxic Interactions Between Platinum Drugs and Taxanes on Bone Marrow Progenitor Cell CFU-GM," *Anticancer Drugs* 10:213-218.
Degterev et al. (2001) "Identification of Small-Molecule Inhibitors of Interaction Between the BH3 Domain and Bcl-XL," *Nature Cell Biol*. 3:173-182.
Denault et al. (2003) "Human Caspase-7 Activity and Regulation by its N-Terminal Peptide," *J. Biol. Chem*. 278:34042-34050.
Denicourt et al. (2004) "Targeting Apoptotic Pathways in Cancer Cells," *Science* 305:1411-1413.
Dominguez et al. (2003) "Zinc Chelation During Non-Lesioning Overexcitation Results in Neuronal Death in the Mouse Hippocampus," *Neuroscience* 116:791-806.
Dominguez et al. (2006) "Neural Overexcitation and Implication of NMDA and AMPA Receptors in a Mouse Model of Temporal Lobe Epilepsy Implying Zinc Chelation," *Epilepsia* 47(5):887-899.
Dothager et al. (Jun. 22, 2005) "Synthesis and Identification of Small Molecules that Potently Induce Apoptosis in Melanoma Cells Through G1 Cell Cycle Arrest," *J. Am. Chem. Soc*. 127(24):8686-8696.
Druker et al. (1996) "Effects of a Selective Inhibitor of the Abl Tyrosine Kinase on the Growth of Bcr-Abl Positive Cells," *Nat Med* 2(5):561-566.
Earnshaw et al. (1999) "Mammalian Caspases: Structure, Activation, Substrates, and Functions During Apoptosis," *Ann. Rev. Biochem*. 68:383-424.
Edelmann et al. (Mar. 12, 2011) "Homo Sapiens Caspase 7, Apoptosis-Related Cystene Peptidase," *NCBI Accession No*. NM_001227.
European Supplementary Search Report, Application No. EP 06771588, Jul. 19, 2010, 2 pages.
European Supplementary Search Report, Application No. EP 10739254, Jul. 25, 2012, 3 pages.
Fesik, S.W. (Nov. 2005) "Promoting Apoptosis as a Strategy for Cancer Drug Discovery," *Nat Rev Cancer* 5:876-885.
Fingl et al. (1975) "General Principles," In; *The Pharmacological Basis of Therapeutics*, Ch. 1, pp. 1-46.
Fink et al. (2001) "Elevated Procaspase Levels in Human Melanoma," *Melanoma Res*. 11:385-393.
Fountain et al. (Nov. 1, 1992) "Homozygous Deletions Within Human Chromosome Band 9p21 in Melanoma," *Proc. Nat. Acad. Sci. USA* 89:10557-10561.
Frederickson et al. (Jun. 2005) "The Neurobiology of Zinc in Health and Disease," *Nat. Rev. Neurosci*. 6:449-462.
Fujita et al. (1998) "Acceleration of Apoptotic Cell Death After the Cleavage of Bcl-XL Protein by Caspase-3-Like Proteases," *Oncogene* 17:1295-1304.

(56) References Cited

OTHER PUBLICATIONS

Gallagher et al. (Sep. 1979) "Characterization of the Continuous, Differentiating Myeloid Cell Line (HL-6-) from a Patient with Acute Promyelocytic Leukemia," *Blood* 54:713-733.
Garrett et al. (2002) "Evaluation of a 6-Month Chemotherapy Protocol with no Maintenance Therapy for Dogs with Lymphoma," *J. Vet. Intern Med.* 16:704-709.
Goode et al. (Aug. 4, 2005) "Using Peptidic Inhibitors to Systematically Probe the S1' Site of Caspase-3 and Caspase-7," *Org. Lett.* 7(16):3529-3532.
Grever et al. (Dec. 1992) "The National Cancer Institute: Cancer Drug Discovery and Development Program," *Seminars Oncology* 19(6):622-638.
Grossman et al. (1999) "Expression and Targeting of the Apoptosis Inhibitor, Survivin, in Human Melanoma," *J. Invest. Dermatol.* 113:1076-1081.
Hanahan et al. (Jan. 7, 2000) "The Hallmarks of Cancer," *Cell* 100:57-70.
Hartmann et al. (Mar. 14, 2000) "Caspase-3: A Vulnerable Factor and Final Effector in Apoptotic Death of Dopaminergic Neurons in Parkinson's Disease," *Proc. Nat. Acad. Sci. USA* 97:2875-2880.
Haskell, C.M. (1980) *Cancer Treatment*, 1$^{st}$ Ed., W.B. Saunders Company, pp. 62-87.
Haskell, C.M. (1991) *Cancer Treatment*, 3rd Ed., W.B. Saunders Company, pp. 62-87.
Haskell, C.M. (2001) *Cancer Treatment*, 5th Ed., W.B. Saunders Company, pp. 78-87.
Hatt, H.H. (1933) "The Constitutions of Some Phosphorus Derivatives of Triphenylmethane," *J. Chem. Soc.* :776-786.
Helmbach et al. (2001) "Drug-Resistance in Human Melanoma," *Int. J Cancer* 93:617-622.
Hergenrother, P.J. (2006) "Obtaining and Screening Compound Collections: A User's Guide and a Call to Chemists," *Curr. Opin. Chem. Biol.* 10(3):213-218.
Hsu et al. (Feb. 2009) "The Design, Synthesis and Evaluation of Procaspase Activating Compounds as Potential Personalized Anti-Cancer Drugs," Poster, Presented at the "Chemistry in Cancer Research: A Vital Partnership in Cancer Drug Discovery and Development," Conference, Feb. 8-11, 2009, New Orleans, LA. http://www.scs.uiuc.edu/~phgroup/comcollections.html.
Huang et al. (2007) "Highly Sensitive Fluorescent Probes for Zinc Ion Based on Triazolyl-Containing Tetradentate Coordination Motifs," *Org. Lett.* 9(24):4999-5002.
Huang et al. (Oct. 2002) "The Chemical Biology of Apoptosis: Exploring Protein-Protein Interactions and the Life and Death of Cells with Small Molecules," *Chem. Biol.* 9:1059-1072.
Huesca et al. (2009) "A Novel Small Molecule with Potent Anticencer Activity Inhibits Cell Growth by Modulating Intracellular Labile Zinc Homeostasis," *Mol. Cancer Therapeutics* 8:2586-2596.
Hwang et al. (2003) "N-Phenethyl-2-Phenylacetamide Isolated from *Xenorhabdus nematophilus* Induces Apoptosis Through Caspase Activation and Calpain-Mediated Bax Cleavage in U937 Cells," *Int. J. Oncol.* 22:151-157.
Igney et al. (Apr. 2002) "Death and Anti-Death: Tumor Resistance to Apoptosis," *Nature Rev. Cancer* 2:277-288.
International Search Report, International Application No. PCT/US2008/061510, Mailed Nov. 19, 2008, 3 pages.
International Search Report, International Application No. PCT/US06/20910, Mailed Apr. 3, 2007, 1 page.
International Search Report, International Application No. PCT/US04/35746, Mailed Jul. 22, 2005, 1 page.
International Search Report, International Application No. PCT/US2010/023543, Mailed Apr. 12, 2010, 3 pages.
Izban et al. (1999) "Characterization of the Interleukin-1 Beta-Converting Enzyme/Ced-3-Family Protease, Caspase-3/CPP32, in Hodgkin's Disease," *Am. J. Pathol.* 154:1439-1447.
Jemal et al. (2002) "Cancer Statistics," *CA Cancer J. Clin.* 52:23-47.
Jeong et al. (2000) "Aromatase Inhibitors from Isodon Excisus Var. Coreanuus," *Arch. Pharm. Res.* 23(3):243-245.
Jiang et al. (2003) "Distinctive Roles of PHAP Proteins and Prothymosin-Alpha in a Death Regulatory Pathway," *Science* 299:223-226.
Johnstone et al. (Jan. 25, 2002) "Apoptosis: A Link Between Cancer Genetics and Chemotherapy," *Cell* 108:153-164.
Karakas et al. (2009) "Structure of the Zinc-Bound Amino-Terminal Domain of the NMDA Receptor NR2B Subunit," *EMBO J.* 28:3910-3920.
Kers et al. (Sep. 15, 1997) "Aryl H-Phosphonates. 7. Studies on the Formation of Phosphorus-Carbon Bond in the Reaction of Trityl and Benzyl Halides with Dialkyl and Diphenyl H-Phosphonates," *Terahedron* 53(37):12691-12698.
Khan et al. (2003) "Three Tyrosine Inhibitors and Antioxidant Compounds from *Salsola foetida*," *Helvetics Chimica Acta* 86:457-464.
Khanna et al. (1990) "Newer Poperazino Oxadiazoled, Formazans, and Tetrazolium Salts as Antiparkinsonian Agents," *Ind. J. Chem. B Org. Chem. Inc. Med. Chem.* 29B(1):91-94.
Khanna et al. (2006) "The Dog as a Cancer Model," *Nat. Biotechnol.* 24(9):1065-1066.
Kimura et al. (2006) "Homo sapiens Caspase 7, Apoptosis-Related Cystene Peptidase (CASP7), Transcript Variant Alpha, mRNA," NCBI Accession No. NM_01227.
Klotzbucher et al. (2004) "Identification of Low Molecular Weight Compounds Mediating Apoptosis by Directly Inducing Cleavage of Procaspase 3," Abstract, In; *Proceedings of the 95$^{th}$ Annual Meeting , American Association for Cancer Research*, Mar. 27-31, Orlando Florida, Abstract No. 4894 (*Proc. Am. Assoc. Cancer. Res.* vol. 45).
Konstantinov et al. (1998) "Alkylphosphocholines: Effects on Human Leukemic Cell Lines and Normal Bone Marrow Cells," *Int. J. Cancer* 77:778-786.
Koty et al. (1999) "Antisense Bcl-2 Treatment Increases Programmed Cell Death in Non-Small Cell Lung Cancer Cell Lines," *Lung Cancer* 23:115-127.
Krepela et all. (Feb. 2004) "Increased Expression of Apaf-1 and Procaspase-3 and the Functionality of Intrinsic Apoptosis Apparatus in Non-Small Cell Lung Carcinoma," *Biol Chem* 385:153-168.
Kunishima et al. (2001) "Formation of Carboxamides by Direct Condensation of Carboxylic Acids and Amines in Alcohols Using a New Alcohol- and Water-Soluble Condensing Agent: DMT-MM," *Tetrahedron* 47:1551-1558.
Kunishima et al. (2002) "Approach to Green Chemistry of DMT-MM: Recovery and Recycle of Coproduct to Chloromethane-Free DMT-MM," *Tetrahedron Lett.* 43:3323-3326.
Lavoie et al. (2007) "Extracellular Chelation of Zinc Does Not Affect Hippocampal Excitability and Seizure-Induced Cell Death in Rats," *J Physiol* 578:275-89.
Lee et al. (2001) "Two New Constituents of *Isodon excisus* and Their Evaluation in an Apoptosis Inhibition Assay," *J. Nat. Prod.* 64:659-660.
Lee et al. (2002) "Agastinal and Agastenol, Novel Lignans from *Agastache rugosa* and Their Evaluation in an Apoptosis Inhibition Assay," *J. Nat. Prod.* 65:414-416.
Lev et al. (Jun. 1, 2004) "Exposure of Melanoma Cells to Dacarbazine Results in Enhanced Tumor Growth and Metastasis in Vivo," *J. Clin. Oncol.* 22:2092-2100.
Li et al. (2000) "Immunotoxicity of N,N-Diethylaniline in Mice: Effect an Natural Killer Activity, Cytotoxic T Lymphocyte Activity, Lymphocyte Proliferation Response and Cellular Components of the Spleen," *Toxicology* 150:179-189.
Li et al. (2004) "A Small Molecule Smac Mimic Potentiates TRAIL- and TNFa-Mediated Cell Death," *Science* 305:1471-1474.
Liang et al. (2002) "Role of Caspase 3-Dependent Bcl-2 Cleavage in Potentiation of Apoptosis by Bcl-2," *Mol. Pharmacol.* 61:142-149.
Lo Russo et al. (1999) "Preclinical Antitumor Activity of XK469 (NSC 656889)," *Invest. New Drugs* 16:287-296.
Lowe et al. (2004) "Intrinsic Tumor Suppression," *Nature* 432:307-315.
Lucas et al. (2011) "Pharmacokinetics and Derication of an Anticancer Dosing Regimen for PAC-1, A Preferential Small Molecule Activator of Procaspase-3, in Healthy Dogs," *Invest. New Drugs* 29:901-911 (Published online May 25, 2010).

(56) References Cited

OTHER PUBLICATIONS

Makin et al. (Jun. 2003) "Recent Advances in Understanding Apoptosis: New Therapeutic Opportunities in Cancer Chemotherapy," *Trends Mol. Med.* 9:251-255.

Marvel Library Compound Collection, http://www.scs.uiuc.eduh/~phgroup/comcollections.html, Downloaded on Jul. 18, 2006.

Marx, J. (Sep. 21, 2001) "New Leads on the 'How' of Alzheimers," *Science* 293:2192-2194.

Mattson et al. (Nov. 2000) "Apoptosis in Neurodegenerative Disorders," *Nat. Rev. Mol. Cell Biol.* 1:120-129.

McGovern et al. (1985) "Pathology of Melanoma: An Overview," In; *Cutaneous Melnoma: Clinical Management and Treatment Results Worldwide*, Ch 3, Balch et. al. eds., J.B. Lippincott Co., Philadelphia, pp. 29-42.

Meergans et al. (2000) "The Short Prodomain Influences Caspase-3 Activation in HeLa Cells," *Biochem. J.*349:135-140.

Middleton et al. (2000) "A Randomized Phase III Study Comparing Dacarbazine, BCNU, Cisplatin and Tamoxifen with Dacarbazine and Inerferon in Advanced Melanoma," *Br. J. Cancer* 82:1158-1162.

Migianu et al. (2005) "New Efficient Synthesis of 1-Hydroxymethylene-1,1-Bisphosphonate Monomethyl Esters," *Synlett.* 3:425-428.

Monks et al. (Oct. 1997) "The NCI Anti-Cancer Drug Screen: A Smart Screen to Identify Effectors of Novel Targets," *Anti-Cancer Drug Design* 12(7):533-541.

Mühlenbeck et al. (1996) "Formation of Hydroxycinnamoylamides and Alpha-Hydroxyacetovanillone in Cell Cultures of *Solanum khasianum*," *Phytochem.* 42(6):1573-1579.

Naganawa et al. (2006) "Further Optimization of Sulfonamide Analogs as EP1 Receptor Antagonists: Synthesis and Evaluation of Bioisosteres fr the carboxylic Acid Group," *Bioorg. Med. Chem.* 14:7121-7137.

Nakagawara et al. (1997) "High Levels of Expression and Nuclear Localization of Interleukin-1 Beta Converting Enzyme (ICE) and CPP32 in Favorable Human Neuroblastomas," *Cancer Res.* 57:4578-4584.

National Center for Biotechnology Information (NCBI) Database of the National Library of Medicine / National Institutes of Health (NIH) website: http://www.ncbi.nlm.nih.gov/ using the Gene database to search for CASP3 (caspase 3, apoptosis-related cysteine protease [*Homo sapiens*] GeneID: 836 Locus tag: HGNC:1504; MIM: 600636 updated May 15, 2005.

Negrel et al. (1996) "Ether-Linked Ferulic Acid Amides in Natural and Wound Periderms of Potato Tuber," *Phytochem.* 43(6):1195-1199.

Nesterenko et al. (2003) "The Use of pH to Influence Regio- and Chemoselectivity in the Asymmetric Aminohydroxylation of Styrenes," *Org. Lett.* 5(3):281-284.

Nesterenko et al. (Dec. 3, 2003) "Identification from a Combinatorial Library of a Small Molecule that Selectively Induces Apoptosis in Cancer Cells," *J. Am. Chem. Soc.* 125(48):14672-14673.

Newmeyer et al. (Feb. 21, 2003) "Mitochondria: Releasing Power for Life and Unleashing the Machineries of Death," *Cell* 112:481-490.

Nguyen et al. (Jun. 24, 2003) "Direct Activation of the Apoptosis Machinery as a Mechanism to Target Cancer Cells," *Proc. Nat. Acad. Sci. USA* 100:7533-7538.

Nielsen et al. (Apr. 1988) "Glycoamide Esters as Biolabile Prodrugs of Carboxilic Acid Agents: Synthesis, Stability, Bioconversion, and Physicochemical Properties," *J. Pharm. Sci.* 77(4):285-298.

Norgrady (1985) "Pro-Drugs and Soft Drugs," In; *Medicinal Chemistry A Biochemical Approach*, Oxford University Press, New York, pp. 388-392.

O'Donovan et al. (2003) "Caspase 3 in Breast Cancer," *Clin Cancer Res* 9:738-742.

Okada et al. (2004) "Pathways of Apoptotic and Non-Apoptotic Death in Tumour Cells," *Nature Rev. Cancer* 4:592-603.

Oltersdorf et al. (Jun. 2005) "An Inhibitor of Bcl-2 Family Proteins Induces Regression of Solid Tumours," *Nature* 435:677-681.

Oredipe et al. (2003) "Limits of Stimulation of Proliferation and Differentiation of Bone Marrow Cells of Mice Treated with Swainsonine," *Internation. Immunopharm.* 3:1537-1547.

Padhani et al. (2001) "The RECIST (Response Evaluation Criteria in Solid Tumors) Criteria: Implications for Diagnostic Radiologists," *Br. J. Radiol.* 74:983-986.

Paoloni et al. (2008) "Translation of New Cancer Treatments from Pet Dogs to Humans," *Nat Rev Cancer* 8:147-156.

Papadopoulos et al. (Aug. 2006) "The Role of Companion Diagnostics in the Development and use of Mutation-Targeted Cancer Therapies," *Nat Biotechnol* 24(8):985-995.

Patton et al. (2004) "Some Precautions in using Chelatos to Buffer Metals in Biological Solutions," *Cell Calcium* 35:427-431.

Persad et al. (2004) "Overexpression of Caspase-3 in Heptocellular Carcinomas," *Modern Patholo.* 17:861-867.

Peterson et al. (Web Release Aug. 26, 2009) "Procaspase-3 Activation as an Anti-Cancer Strategy: Structure-Activity Relationship of Procaspase-Activating Compound 1 (PAC-1) and its Cellular Co-Localization with Caspase-3," *J. Med. Chem.* 52(18):5721-5731.

Peterson et al. (Web Release Mar. 10, 2009) "PAC-1 Activates Procaspase-3 in Vitro Through Relief of Zinc-Mediated Inhibition," *J. Mol. Biol.* 388:144-158.

Peterson et al. (Web Release Sep. 7, 2010) "Discovery and Canine Preclinical Assessment of a Nontoxic Procaspase-3-Activating Compound," *Cancer Res.* 70(18):7232-7241.

Plowman, J. (1995) "Efficacy of the Quinocarmycins KW2152 and DX-52-1 Against Human Melanoma Lines Growing in Culture and in Mice," *Cancer Res.* 55(4):862-867.

Pop et al. (2003) "Mutations in the Procaspase-3 Dimer Interface Affect the Activity of the Zymogen," *Biochem.* 42:12311-12320.

Prater et al. (2002) "Single-Dose Topical Exposure to the Pyrethroid Insecticide, Permethrin in C57BL/6N Mice: Effects on Thymus and Spleen," *Food Chem. Toxicol.* 40:1863-1873.

Putt et al. (2005) "Direct Quantification of Poly(ADP-ribose) Polymerase (PARP) Activity as a Means to Distinguish Necrotic and Apoptotic Death in Cell and Tissue Samples," *ChemBioChem* 6:53-55.

Putt et al. (Aug. 27, 2006) "Small-Molecule Activation of Procaspase-3 to Caspase-3 as a Personalized Anticancer Strategy," *Nat. Chem. Biol.* 2(10):543-550.

Putt et al. (Mar. 1, 2004) "An Enzymatic Assay for Poly(ADP-ribose) Polymerase-1 (PARP-1 Via the Chemical Quantitation of NAD(+): Application to the High-Throughput Screening of Small Molecules as Petential Inhibitors," *Anal. Biochem.* 326(1):78-86.

Putt et al. (Oct. 15, 2004) "A Nonradiometric, High-Throughput Assay for Poly(ADP-ribose) Glycohydrolase (PARG): Application to Inhibitor Identification and Evaluation." *Anal. Biochem.* 333(2):256-264.

Rassnick et al. (2002) MOPP Chemotherapy for Treatment of Resistant Lymphoma in Dogs: A Retrospective Study of 117 Cases (1989-2000) *J. Vet Intern. Med.*16:576-580.

Reed et al. (Feb. 2002) "Apoptosis-Based Therapies," *Nat. Rev. Drug Dis.* 1:111-121.

Ren et al. (2008) "Characterization of the in Vivo and in Vitro Metabolic Profile of PAC-a Using Liquid Chromatography-Mass Spectrometry," *J. Chromatogr. B* 876(1):47-53.

Roy et al. (2001) "Maintenance of Caspase-3 Proenzyme Dormancy by an Intrinsic "Safety Catch" Regulatory Tripeptide," *Proc. Nat. Acad. Sci. USA* 98:6132-6137.

Sala et al. (Published online May 5, 2008) "BRAF Silencing by Short Hairpin RNA or Chemical Blockade by PLX4032 Leads to Different Responses in Melanoma and Thyroid Carcinoma Cells," *Mol Cancer Res* 6:751-759.

Salerno et al. (Jan. 2010) Cytostatic Activity of Adenosine Triphosphate-Competitive Kinase Inhibitors in BRAF Mutant Thyroid Carcinoma Cells. *J Clin Endocrinol Metab* 95(1): 450-455.

Satoh et al. (Published online May 26, 2009) "Phase I Study of YM155, a Novel Survivin Suppressant, in Patients with Advanced Solid Tumors," *Clin. Cancer Res.* 15:3872-3880.

Satyamoorthy et al. (May 2001) "No Longer a Molecular Black Box—New Clues to Apoptosis and Drug Resistance in Melanoma," *Trends Mol. Med.* 7:191-194.

(56) References Cited

OTHER PUBLICATIONS

Schadendorf et al. (Jan. 1, 1994) "Chemosensitivity Testing of Human Malignant Melanoma. A Retrospective Analysis of Clinical Response and in Vitro Drug Sensitivity," *Cancer* 73:103-108.
Sengupta et al. (1978) "Search for Potential Psychotropic Agents. Part II. N-Benzylidene Derivatives of 4-Arylpiperazine-1-Acetic Acid Hydrazides," *Polish J. Pharm. Pharmacy* 30(1):89-94.
Serrone et al. (2000) "Dacarbazine-Based Chemotherapy for Metastic Melanome: Thirty-Year Experience Overview," *J. Exp. Clin. Cancer Res.* 19:21-34.
Shermolovich et al. (1980) "Reactions of Fuchsone with Dialkyl Hydrogen and Trialkyl Phosphites," *J. Gen. Chem. USSR* 50(4):649-652, 811-815.
Shi, Y. (2002) "Mechanisms of Caspase Activation and Inhibition During Apoptosis," *Mol. Cell* 9:459-470.
Silverman et al. (2006) "Combinatorial Chemistry and Molecular Diversity Tools for Molecular Diversification and Their Applications in Chemical Biology," *Curr. Opin. Chem. Biol.* 10(3):185-187.
Singh et al. (Jan. 2004) "Sulforaphane Induces Caspase-Mediated Apoptosis in Cultured PC-3 Human Prostate Cancer Cells and Retards Growth of PC-3 Xeonografts in Vivo," *Carcinogenesis* 25(1):83-90.
Slee et al. (Apr. 1, 1996) "Benzyloxycarbonyl-Val-Ala-Asp (OMe) Fluoromethylketone (Z-VAD.FMK) Inhibits Apoptosis by Blocking the Processing of CPP32," *Biochem. J.* 315(1):21-24.
Soengas et al. (2003) "Apoptosis and Melanoma Chemoresistance," *Oncogene* 22:3138-3151.
Soengas et al. (Jan. 11, 2001) "Inactivation of the Apoptosis Effector Apaf-1 in Malignant Melanoma," *Nature* 409:207-211.
Stennicke et al. (1998) "Pro-Caspase-3 Is a Major Physiologic Target of Caspase-8," *J. Biol. Chem.* 273:27084-27090.
Sun et al. (Oct. 2008) "Design of Small-Molecule Peptidic and Nonpeptidic Smac Mimetics," *Acc. Chem. Res.* 41(10):1264-1277.
Sundström et al. (1976) "Establishment and Characterization of a Human Histiocytic Lymphoma Cell Line (U-937)," *Int. J. Cancer* 17:565-577.
Supplementary European Search Report, Corresponding to European Application No. EP 06 77 1588, Completed Jul. 19, 2010.
Supplementary European Search Report, Corresponding to European Application No. EP 10 73 9254, Completed Jul. 25, 2012.
Svingen et al. (2004) "Components of the Cell Death Machine and Drug Sensitivity of the National Cancer Institute Cell Line Panel," *Clin. Cancer Res.* 10:6807-6820.
Tagawa et al. (1985) "Low-Dose Cytosine Arabinoside Regimen Induced a Complete Remission with Normal Karyotypes in a Case with Hypoplastic Acute Myeloid Leukaemia with No. 8-Trisomy: In Vitro and in Vivo Evidence for Normal Haematopoietic Recovery," *Br J Haematol* 60:449-455.
Tomita et al. (Dec. 1990) "A New Screening Method for Melanin Biosynthesis Inhibitors Using *Streptomyces bikiniensis*," *J. Antibiotics* 43(12):1601-1605.
Tovar et al. (Feb. 7, 2006) "Small-Molecule MDM2 Antagonists Reveal Aberrant p53 Signaling in Cancer: Implications for Therapy," *PNAS* 103(6):1888-1893.
Traven et al. (2004) "Protein Hijacking: Key Proteins Held Captive Against Their Will," *Cancer Cell* 5:107-108.
Vassilev et al. (2004) "In Vivo Activation of the p53 Pathway by Small-Molecule Antagonists of MDM2," *Science* 303:844-848.
Vail et al., (2004) "Vetrinary Co-operative Oncology Group—Common Terminology Criteria for Adverse Events (VCOG-CTCAE) Following Chemotherapy of Biological Antineoplastic Therapy in Dogs and Cats v1.0," *Vet Comp. Oncol.* 2:195-213.
Vichai et al. (Published online Aug. 17, 2006) "Sulforhodamine B Colorimetric Assay for Cytotoxicity Screening," *Nat. Protocols* 1(3):1112-1116.
Vogelstein et al. (2001) "Achilles' Heel of Cancer," *Nature* 412:865-866.
Vogelstein et al. (Aug. 2004) "Cancer Genes and the Pathways they Control," *Nat Med* 10(8):789-799.
Wadsworth et al. (1973) "Ethyl Cyclohexylideneacetate," *Organic Synthesis Coll.* 5:547, 45:44.
Wajant et al. (2003) "Targeting the FLICE Inhibitory Protein (FLIP) in Cancer Therapy," *Mol. Interv.* 3:124-127.
Wang et al. (2000) "Structure-Based Discovery of an Organic Compound that Binds Bcl-2 Protein and Induces Apoptosis of Tumor Cells," *Proc. Natl. Acad. Sci.* 97:7124-7129.
Wright et al. (Oct. 6, 1997) "Activation of CPP32-Like Proteases is Not Sufficient to Trigger Apoptosis: Inhibition of Apoptosis by Agents that Suppress Activation of AP24, but not CPP32-Like Activity," *J. Exp. Med.* 186(7):1107-1117.
Yamaura et al. (Feb. 2002) "Inhibition of the Antibody Production by Acetaminophen Independent of Liver Injury in Mice," *Bio. Pharm. Bull.* 25(2):201-205.
Young et al. (1956) "The Use of Phosphorous Acid Chlorides in Peptide Synthesis," *J. Am. Chem. Soc.* 78:2126-2131.
Zalupski et al. (Jul. 3, 1991) "Phase III Comparison of Doxorubicin and Dacarbazine Given by Bolus Versus Infusion in Patients With Soft-Tissue Sarcomas: A Southwest Oncology Group Study," *J. Natl. Cancer Inst.* 83(13):926-932.
Zornig et al. (2001) "Apoptosis Regulators and their Role in Tumorigenesis," *Biochim. Biophys. Acta* 1551:F1-F37, abstract only.
Dorn et al. (1970) "The Epidemiology of Canine Leukemia and Lymphoma," *Bibl Haematol.* :403-415.
Franklin et al. (2005) "Zinc and Zinc Transporters in Normal Prostate and the Pathogenesis of Prostate Cancer," *Front. Biosci.* 10:2230-2239.
Kahl, B. (2008) "Chemotherapy Combinations with Monoclonal Antibodies in non-Hodgkin's Lymphoma," *Semin Hematol* 45:90-94.
Wang et al. (Jan. 2002) "CPP32 Expression and its Significance in Multidrug-Resistant Tumor Cells and their Parent Cells," *Di Yi Jun Yi Da Xue Xue Bao* 22(1):32-34.

\* cited by examiner

A)

B)

Day 0

Day 7

DESIGN, SYNTHESIS AND EVALUATION OF PROCASPASE ACTIVATING COMPOUNDS AS PERSONALIZED ANTI-CANCER DRUGS

STATEMENT ON FEDERALLY SPONSORED RESEARCH OR DEVELOPMENT

This invention was made with government support under R01-CA120439 awarded by the National Institutes of Health, 1 T32 GM070421 awarded by the National Institutes of Health, and F31-CA13013801S1 awarded by the National Institutes of Health. The government has certain rights in the invention.

CROSS REFERENCE TO RELATED APPLICATIONS

This application is the U.S. National Stage of International Application No. PCT/US2010/023543, filed Feb. 9, 2010, which claims the benefit of U.S. Provisional Patent Application Ser. No. 61/151,064 filed Feb. 9, 2009 both of which are incorporated by reference in entirety.

BACKGROUND OF THE INVENTION

Apoptosis, or programmed cell death, plays a central role in the development and homeostasis of all multicellular organisms (Shi Y, 2002, Molecular Cell 9:459-470). A frequent hallmark of cancer is resistance to natural apoptotic signals. Depending on the cancer type, this resistance is typically due to up- or down-regulation of key proteins in the apoptotic cascade or to mutations in genes encoding these proteins. Such changes occur in both the intrinsic apoptotic pathway, which funnels through the mitochondria and caspase-9, and the extrinsic apoptotic pathway, which involves the action of death receptors and caspase-8. For example, alterations in proper levels of proteins such as p53, Bim, Bax, Apaf-1, FLIP and many others have been observed in cancers. The alterations can lead to a defective apoptotic cascade, one in which the upstream pro-apoptotic signal is not adequately transmitted to activate the executioner caspases, caspase-3 and caspase-7. FIG. 1 shows aspects of the apoptotic cascade.

As most apoptotic pathways ultimately involve the activation of procaspase-3, upstream genetic abnormalities are effectively "breaks" in the apoptotic circuitry, and as a result such cells proliferate atypically. Given the central role of apoptosis in cancer, efforts have been made to develop therapeutics that target specific proteins in the apoptotic cascade. For instance, peptidic or small molecule binders to cascade members such as p53 and proteins in the Bcl family or to the inhibitor of apoptosis (IAP) family of proteins have pro-apoptotic activity, as do compounds that promote the oligomerization of Apaf-1. However, because such compounds target early (or intermediate to high) positions on the apoptotic cascade, cancers with mutations in proteins downstream of those members can still be resistant to the possible beneficial effects of those compounds.

For therapeutic purposes it would be advantageous to identify a small molecule that directly activates a proapoptotic protein far downstream in the apoptotic cascade. The approach to our invention involves such a relatively low position in the cascade, thus enabling the killing of even those cells that have mutations in their upstream apoptotic machinery. Moreover, the therapeutic strategies disclosed herein can have a higher likelihood of success if that proapoptotic protein were upregulated in cancer cells. In the present invention, our efforts to identify small molecules began with targeting the significant downstream effector protein of apoptosis, procaspase-3.

The conversion or activation of procaspase-3 to caspase-3 results in the generation of the active "executioner" caspase form that subsequently catalyzes the hydrolysis of a multitude of protein substrates. Active caspase-3 is a homodimer of heterodimers and is produced by proteolysis of procaspase-3. In vivo, this proteolytic activation typically occurs through the action of caspase-8 or caspase-9. To ensure that the proenzyme or zymogen is not prematurely activated, procaspase-3 has a 12 amino acid "safety catch" that blocks access to the ETD site (amino acid sequence, ile-glu-thr-asp) of proteolysis. See Roy, S. et al.; Maintenance of caspase-3 proenzyme dormancy by an intrinsic "safety catch" regulatory tripeptide, Proc. Natl. Acad. Sci. 98, 6132-6137 (2001).

This safety catch enables procaspase-3 to resist autocatalytic activation and proteolysis by caspase-9. Mutagenic studies indicate that three consecutive aspartic acid residues appear to be the critical components of the safety catch. The position of the safety catch is sensitive to pH; thus, upon cellular acidification (as occurs during apoptosis) the safety catch is thought to allow access to the site of proteolysis, and active caspase-3 can be produced either by the action of caspase-9 or through an autoactivation mechanism.

In particular cancers, the expression of procaspase-3 is upregulated. A study of primary isolates from 20 colon cancer patients revealed that on average, procaspase-3 was upregulated six-fold in such isolates relative to adjacent noncancerous tissue (Roy et al., 2001). In addition, procaspase-3 is upregulated in certain neuroblastomas, lymphomas, and liver cancers (Nakagawara, A. et al., 1997, Cancer Res. 57:4578-4584; Izban, K. F. et al., Am. J. Pathol. 154:1439-1447; Persad, R. et al., Modern Patholo. 17:861-867). Furthermore, a systematic evaluation was performed of procaspase-3 levels in the 60 cell-line panel used for cancer screening by the National Cancer Institute (NCI) Developmental Therapeutics Program. The evaluation revealed that certain lung, melanoma, renal, and breast cancers show greatly enhanced levels of procaspase-3 expression (Svingen, P. A. et al., Clin. Cancer Res. 10:6807-6820).

Due to the role of active caspase-3 in achieving apoptosis, the relatively high expression levels of procaspase-3 in certain cancerous cell types, and the intriguing safety catch-mediated suppression of its autoactivation, we reasoned that small molecules that directly modify procaspase-3 could be identified and that such molecules could have great applicability in targeted cancer therapy.

Herein we disclose, inter alia, compositions and methods including small molecules capable of inducing cell death. In embodiments, compositions and methods involve compounds which can interact directly or indirectly with programmed cell death pathway members such as procaspase-3. In embodiments, compositions and methods of the invention have reduced neurotoxicity as compared to other compounds which interact directly or indirectly with programmed cell death pathway members such as procaspase-3.

SUMMARY OF THE INVENTION

The invention broadly provides compounds, compositions, and methods of therapeutic treatment. In embodiments, the inventions are applicable in the context of a variety of cancer diseases and cancer cell types such as breast, lymphoma, adrenal, renal, melanoma, leukemia, neuroblastoma, lung, brain, and others known in the art.

As a further introduction, compounds capable of activating an enzyme that is often overexpressed in its inactive form in cancer cells have been discovered. The compounds induce programmed cell death (apoptosis) in cancer cells, including those that have upregulated procaspase-3. Many cancers resist standard chemotherapy. Compounds of the invention can take advantage of a biological target that may be upregulated in cancer cells and thus can prove effective even in cells with defects in their apoptotic machinery. These compounds can also be successful in targeted cancer therapy, where there can be advantages of selectivity in the killing of cancer cells with comparably reduced adverse reactions to noncancerous cells having lower levels of procaspase-3. These adverse reactions can include toxicity, particularly neurotoxicity.

Without wishing to be bound by a particular theory, it is believed that embodiments of compounds, compositions and methods of the invention may act via the mechanism of modulation of apoptosis or programmed cell death to be effective in the treatment of cancer cells. In a preferred embodiment, the modulation of apoptosis is by induction of apoptosis. In another embodiment, the modulation of apoptosis is by inhibition of apoptosis.

Provided are compounds having an N-acyl hydrazone zinc-chelating core with at least one polar group attached to a terminal phenyl ring. Also provided are compounds having an ortho-hydroxyl N-acyl hydrazone zinc-chelating core with at least one polar group attached to a terminal phenyl ring.

More specifically, provided are compounds having formula (FX1):

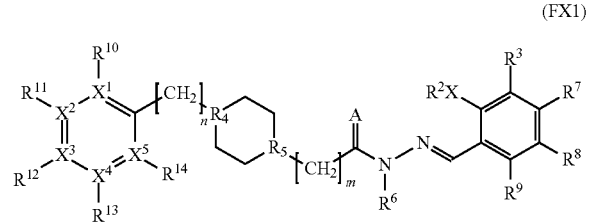

(FX1)

wherein
$X^1$, $X^2$, $X^3$, $X^4$, and $X^5$ are each independently C or N, wherein when $X^1$, $X^2$, $X^3$, $X^4$, and $X^5$ is N, the corresponding $R^{10}$, $R^{11}$, $R^{12}$, $R^{13}$, or $R^{14}$ is absent;
one of $R^{10}$, $R^{11}$, $R^{12}$, $R^{13}$, $R^{14}$, $R^3$, $R^7$, $R^8$, or $R^9$ contains a polar group selected from the group consisting of: a sulfonamide group, a nitro group, an amino group, a carboxylate group, a sulfonyl group, and an aryl sulfonyl group;
the others of $R^{10}$, $R^{11}$, $R^{12}$, $R^{13}$, $R^{14}$, $R^3$, $R^7$, $R^8$, or $R^9$ are each independently selected from the group consisting of: hydrogen, halogen, a sulfonamide group, a nitro group, an amino group, a carboxylate group, a sulfonyl group, an aryl sulfonyl group, an alkoxy group, C1-C6 alkyl, C1-C6 alkoxy, and C2-C6 alkenyl; n and m are each independently integers from 1 to 3; $R_4$ and $R_5$ are each independently CH or N; A is O or S; $R^6$ is hydrogen or $C_1$-$C_6$ alkyl; X is oxygen; and $R^2$ is hydrogen, C1-C6 alkyl, or C1-C6 alkoxy.

Also provided is a compound having formula (FX11):

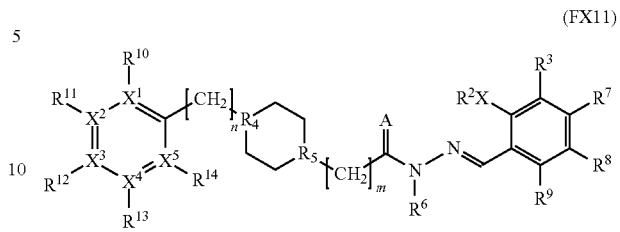

(FX11)

wherein
$X^1$, $X^2$, $X^3$, $X^4$, and $X^5$ are each independently C or N, wherein when $X^1$, $X^2$, $X^3$, $X^4$, and $X^5$ is N, the corresponding $R^{10}$, $R^{11}$, $R^{12}$, $R^{13}$, or $R^{14}$ is absent;
one of $R^{10}$, $R^{11}$, $R^{12}$, $R^{13}$, and $R^{14}$ contains a polar group selected from the group consisting of: a sulfonamide group, a nitro group, an amino group, a carboxylate group, a sulfonyl group, and an aryl sulfonyl group;
the others of $R^{10}$, $R^{11}$, $R^{12}$, $R^{13}$, and $R^{14}$ are each independently selected from the group consisting of: H, halogen, a sulfonamide group, a nitro group, an amino group, a carboxylate group, a sulfonyl group, an aryl sulfonyl group, and an alkoxy group; n and m are each independently integers from 1 to 3; $R_4$ and $R_5$ are each independently CH or N; A is O or S; $R^6$ is hydrogen or C1-C6 alkyl; $R^3$, $R^7$, $R^8$, $R^9$ are each independently selected from hydrogen, halogen, C1-C6 alkyl, C1-C6 alkoxy or $C_2$-$C_6$ alkenyl; X is oxygen; and $R^2$ is hydrogen, C1-C6 alkyl, or C1-C6 alkoxy.

In an embodiment, $R^2X$ is —OH in any of the formulas and structures provided herein. In an embodiment, $R^3$ is methoxy or allyl in any of the formulas and structures provided herein. In an embodiment, in Formula (FX1), one of $R^{10}$, $R^{11}$, $R^{12}$, $R^{13}$, $R^{14}$, $R^3$, $R^7$, $R^8$, or $R^9$ is selected from the group consisting of: —NO$_2$;

—COOH;

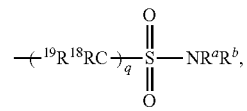

where $R^a$ and $R^b$ are each independently hydrogen, C1-C6 alkyl, and C1-C6 alkoxy; $R^{18}$ and $R^{19}$ are each independently selected from the group consisting of hydrogen and C1-C6 alkyl; and q is an integer from 0 to 3; and

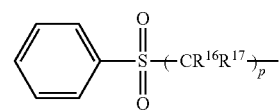

where $R^{16}$ and $R^{17}$ are each independently selected from the group consisting of hydrogen and C1-C6 alkyl, and p is an integer from 0 to 3.

In an embodiment, in Formula (FX1) or (FX11), one of $R^{10}$, $R^{11}$ or $R^{12}$ is selected from the group consisting of:
—$NO_2$;
—COOH:

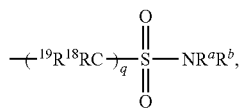

where $R^a$ and $R^b$ are each independently hydrogen, C1-C6 alkyl, and C1-C6 alkoxy; $R^{18}$ and $R^{19}$ are each independently selected from the group consisting of hydrogen and C1-C6 alkyl; and q is an integer from 0 to 3; and

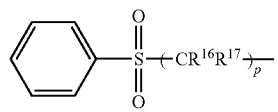

where $R^{16}$ and $R^{17}$ are each independently selected from the group consisting of hydrogen and C1-C6 alkyl, and p is an integer from 0 to 3.

In an embodiment, in Formula (FX1), one of $R^{10}$, $R^{11}$, $R^{12}$, $R^{13}$, $R^{14}$, $R^3$, $R^7$, $R^8$, or $R^9$ is

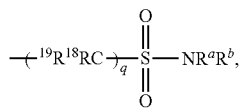

where $R^a$ and $R^b$ are each independently hydrogen, C1-C6 alkyl, and C1-C6 alkoxy; $R^{18}$ and $R^{19}$ are each independently selected from the group consisting of hydrogen and C1-C6 alkyl; and q is an integer from 0 to 3.

In an embodiment, in Formula (FX1) or (FX11), one of $R^{10}$, $R^{11}$, $R^{12}$, $R^{13}$, or $R^{14}$ is

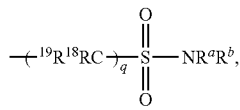

where $R^a$ and $R^b$ are each independently hydrogen, C1-C6 alkyl, and C1-C6 alkoxy; $R^{18}$ and $R^{19}$ are each independently selected from the group consisting of hydrogen and C1-C6 alkyl; and q is an integer from 0 to 3.

In an embodiment, in Formula (FX1) or (FX11), $R^{12}$ is

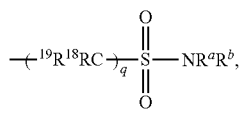

where $R^a$ and $R^b$ are each independently hydrogen, C1-C6 alkyl, and C1-C6 alkoxy; $R^{18}$ and $R^{19}$ are each independently selected from the group consisting of hydrogen and C1-C6 alkyl; and q is an integer from 0 to 3. In an embodiment, in $R^{12}$, $R^a$ and $R^b$ are each hydrogen and q is 0.

In an embodiment, $R^3$ is allyl, X is O and $R^2$ is hydrogen. In an embodiment, $R^{12}$ is —S(=O)$_2$—NH$_2$. In an embodiment, $R^{11}$, $R^{12}$ and $R^{13}$ are methoxy. In an embodiment, $R^3$ is allyl, X is O and $R^2$ is hydrogen. In an embodiment, one or two of $X^1$, $X^2$, $X^3$, $X^4$, and $X^5$ are N.

Also provided is a compound of Formula (FX1) or (FX11) having formula (FX2):

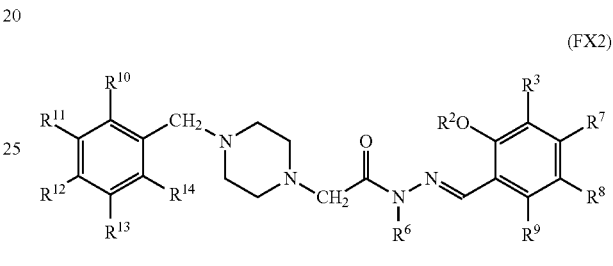

where the variables are as described elsewhere herein for Formulas (FX1) or (FX11).

Also provided is a compound of Formula (FX1) or (FX11) having formula (FX12):

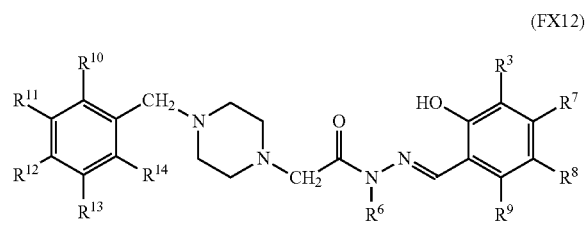

where the variables are as described elsewhere herein for Formulas (FX1) or (FX11).

Also provided is a compound of Formula (FX1) or (FX11) having formula (FX3), (FX4), (FX5), or (FX6):

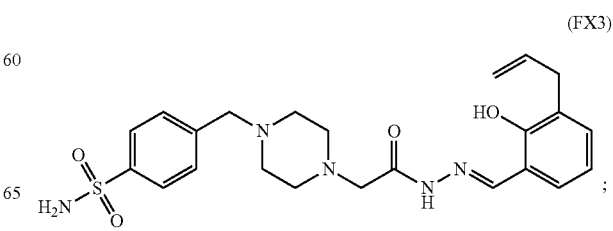

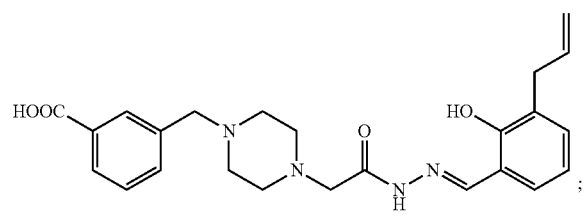
(FX4)
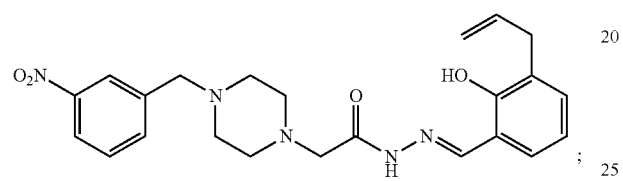
(FX5)
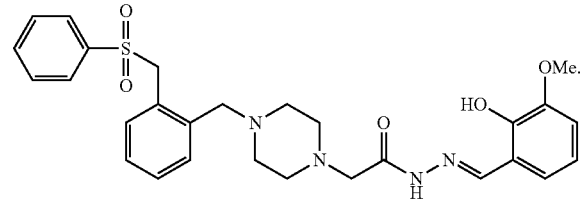
(FX6)
Also provided is a compound of Formula (FX1) or (FX11) having formula (FX7) or (FX8):
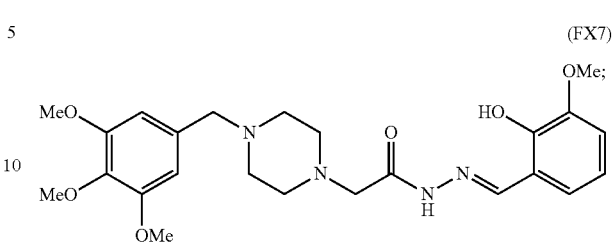
(FX7)
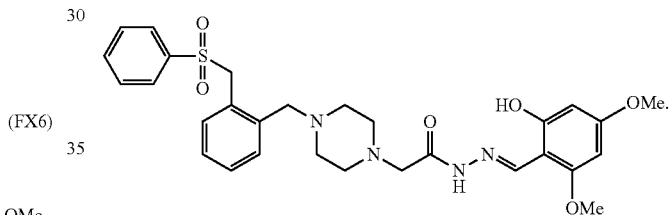
(FX8)
Also provided is a compound of Formula (FX1) or (FX11) which includes a fluorescent label. Also provided is a compound of Formula (FX1) or (FX11) having the structure (FX9):
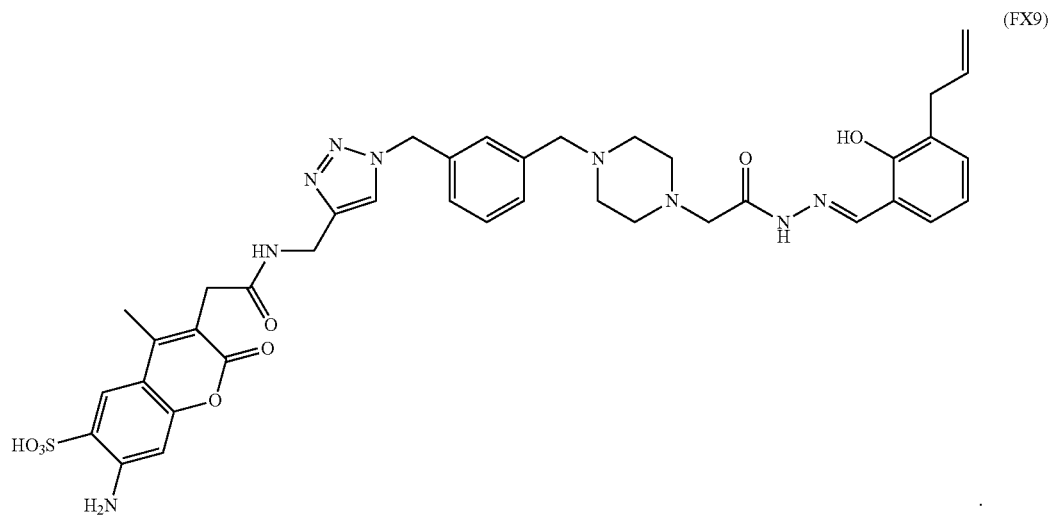 [SMILES: C=CCc1cccc(/C=N/NC(=O)CN2CCN(Cc3cccc(Cn4cc(CNC(=O)Cc5c(C)c6cc(S(=O)(=O)O)c(N)cc6oc5=O)nn4)c3)CC2)c1O ; "."]
(FX9)

Also provided in an embodiment is a method of selectively inducing apoptosis in a cancer cell, comprising administering to said cancer cell a compound capable of modifying a procaspase-3 molecule of said cancer cell; wherein said compound is the compound of Formula (FX1) or (FX11). Also provided in an embodiment is a method of selectively inducing apoptosis in a cancer cell, comprising administering to said cancer cell a compound capable of modifying a procaspase-3 molecule of said cancer cell; wherein said compound is the compound of Formula (FX1) or (FX11), and wherein said cancer cell is in a patient in need of treatment. Also provided in an embodiment is a method of treating a cancer cell, comprising (a) identifying a potential susceptibility to treatment of a cancer cell with a procaspase activator compound; and (b) exposing said cancer cell to an effective amount of the procaspase activator compound; wherein the procaspase activator compound is the compound of Formula (FX1) or (FX11). Also provided in an embodiment is a method of treating a cancer cell, comprising (a) identifying a potential susceptibility to treatment of a cancer cell with a procaspase activator compound; and (b) exposing said cancer cell to an effective amount of the procaspase activator compound; wherein the procaspase activator compound is the compound of Formula (FX1) or (FX11) wherein said procaspase activator compound is capable of activating at least one of procaspase-3 and procaspase-7. Also provided in an embodiment is a method of inducing death in a cancer cell, comprising administering to said cancer cell a compound capable of activating a procaspase-3 molecule of said cancer cell, wherein said compound is the compound of Formula (FX1) or (FX11). Also provided in an embodiment is a medicament comprising an effective amount of one or more compounds of Formula (FX1) or (FX11). Also provided in an embodiment is a method of making a medicament for treatment of a cancer cell which comprises one or more compounds of Formula (FX1) or (FX11). Also provided in an embodiment is a method of inducing apoptosis in a cell, comprising administering to said cell a compound of Formula (FX1) or (FX11). Also provided is a method as described herein wherein the procaspase activator compound has a log BB of −0.4 to −2. Also provided is a method as described herein wherein the compound of formula (FX1) or (FX11) has a log BB of −0.4 to −2. Also provided is a method as described herein wherein the compound does not cross the blood-brain barrier to such as extent to cause appreciable neurotoxic effects in a patient. Also provided is an ex vivo method comprising contacting a cell with an effective amount of a compound of Formula (FX1) or (FX11). Also provided is a method of treating a cell, the method comprising the step of contacting a cell with an effective amount of a compound of Formula (FX1) or (FX11). Also provided is a compound according to Formula (FX1) or (FX11) for use in therapy. Also provided is a compound according to Formula (FX1) or (FX11) or the treatment of cancer. Also provided is the use of a compound according to Formula (FX1) or (FX11). In the manufacture of a medicament for the treatment of cancer.

In an aspect, at least one substituent on the compounds of the invention is a polar group. In an embodiment, A is O. In an embodiment, both $R^4$ and $R^5$ are N. In an embodiment, m and n are both 1. In an embodiment, $X^1$, $X^2$, $X^3$, $X^4$, and $X^5$ are all C. In an embodiment, $R^6$ is H. In an embodiment, $R^7$, $R^8$ and $R^9$ are all H. In an embodiment, R3 is allyl. In an embodiment, R10 and R14 are H and R11, R12 and R13 are each methoxy. In an embodiment, $R^2X$ is —OH. In an embodiment, $R^3$ is methoxy. In an embodiment, one of R3, R7, R8 and R9 is methoxy. In an embodiment, two of R3, R7, R8 and R9 are methoxy. In an embodiment, three of R3, R7, R8 and R9 is methoxy. In an embodiment, one of $R^{10}$, $R^{11}$, $R^{12}$, $R^{13}$, and $R^{14}$ is methoxy. In an embodiment, two of $R^{10}$, $R^{11}$, $R^{12}$, $R^{13}$, and $R^{14}$ are methoxy. In an embodiment, $R^{10}$ and $R^{13}$ are methoxy. In an embodiment, three of $R^{10}$, $R^{11}$, $R^{12}$, $R^{13}$, and $R^{14}$ are methoxy. In an embodiment, only one of $R^{10}$, $R^{11}$, $R^{12}$, $R^{13}$, and $R^{14}$ is not hydrogen. In an embodiment, only one of $R^{11}$, $R^{12}R^{13}$, and $R^{14}$ is not hydrogen. In an embodiment, $R^{11}$ or $R^{12}$ is not hydrogen.

In an aspect of the invention, a compound of any of the formulas described and shown herein is labeled with a fluorescent label. The use of a fluorescent label with the compounds and methods of the invention allows tracking the compound in a desired system, determination of the concentration of the compound, and has other uses, as known in the art. The identity, use, synthesis, and choice of a particular fluorescent label is within the level of skill of one of ordinary skill in the art. In a particular embodiment, the fluorescent label is Alexa Fluor 350. Other fluorescent labels are intended to be included and disclosed here as if they were individually listed.

In an aspect of the invention, compounds of the invention do not cross the blood-brain barrier in a sufficient amount to cause an amount of neurotoxicity that would require termination of treatment or other adverse effects. In an aspect of the invention, compounds of the invention have a log BB of −0.4 to −2, for example.

In an aspect of the invention, compounds of the invention induce cell death in cancer cells. In embodiments of this aspect of the invention, compounds of the invention induce cell death in lymphoma, leukemia, melanoma, cervical and breast cancer cells.

As used herein, a "polar group" comprises at least one bond that is at least partially polar as the term is used in the art. A polar group contains at least one bond with a dipole moment. A "polar group" as used herein may include a polar group as a part of an overall chemical "group" as the term is used in the art.

As used herein, a sulfonamide group has the structure:

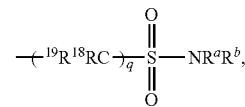

where $R^a$ and $R^b$ are each independently hydrogen, C1-C6 alkyl, and C1-C6 alkoxy; $R^{18}$ and $R^{19}$ are each independently selected from the group consisting of hydrogen and C1-C6 alkyl; and q is an integer from 0 to 6. In an embodiment, $R^a$ and $R^b$ are each hydrogen.

As used herein, a sulfonyl group contains the structure: —SO₂—. In an embodiment, the sulfonyl group is a part of an aryl sulfonyl group having the structure:

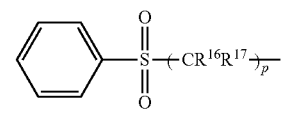

where $R^{16}$ and $R^{17}$ are each independently selected from the group consisting of hydrogen and C1-C6 alkyl, where the aryl group may be optionally substituted with one or more heteroatoms in the ring and may be optionally substituted with one or more halogen atoms, nitro groups, C1-C6 alkyl groups, and C1-C6 alkoxy groups and p is an integer from 0 to 6. A sulfonyl group may be terminated by any suitable substituent such as hydrogen or C1-C6 alkyl.

As used herein, allyl refers to the alkenyl group —$CH_2$—$CH=CF_{12}$.

As used herein, a nitro group contains the structure: —$NO_2$. In an embodiment, a nitro group may be the terminal group of an alkylnitro group, where one to 6 optionally substituted methylene groups precede the nitro functional group. As used herein, a carboxylate group contains the structure: —COOH. In an embodiment, the carboxylate group is terminated by a C1-C6 alkyl group instead of hydrogen.

DETAILED DESCRIPTION OF THE INVENTION

Figure 1:
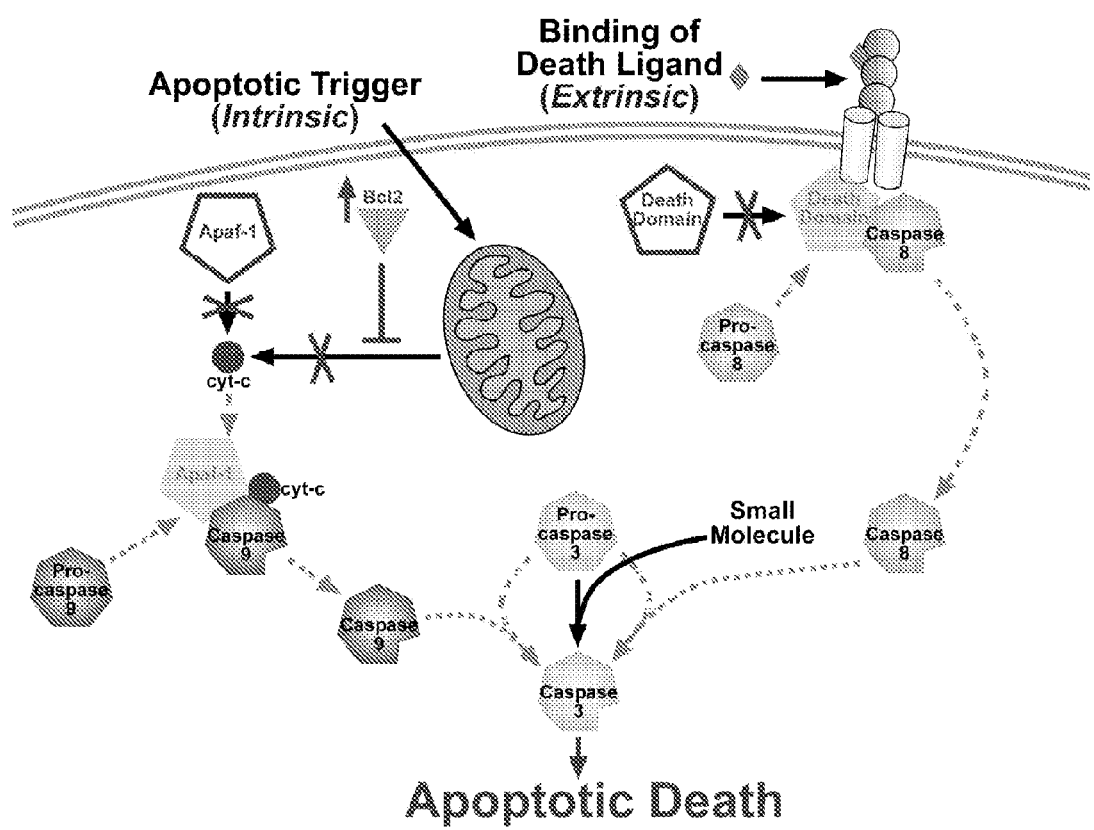
FIG. 1 shows some aspects of small molecule activation of procaspase-3.

In general, the terms and phrases used herein have their art-recognized meaning, which can be found by reference to standard texts, journal references and contexts known to those skilled in the art.

The following abbreviations are applicable. IAP, inhibitor of apoptosis; PAC-1, procaspase activating compound 1; PARP, Poly(ADP-ribose) polymerase.

The definitions are provided to clarify their specific use in the context of the invention.

When used herein, the term "chemotherapeutic agent" refers to any substance capable of reducing or preventing the growth, proliferation, or spread of a cancer cell, a population of cancer cells, tumor, or other malignant tissue. The term is intended also to encompass any antitumor or anticancer agent.

When used herein, the term "effective amount" is intended to encompass contexts such as a pharmaceutically effective amount or therapeutically effective amount. For example, in embodiments the amount is capable of achieving a beneficial state, beneficial outcome, functional activity in a screening assay, or improvement of a clinical condition.

When used herein, the term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art.

The term "alkyl" refers to a monoradical branched or unbranched saturated hydrocarbon chain preferably having from 1 to 22 carbon atoms and to cycloalkyl groups having one or more rings having 3 to 22 carbon atoms. Short alkyl groups are those having 1 to 6 carbon atoms including methyl, ethyl, propyl, butyl, pentyl and hexyl groups, including all isomers thereof. Long alkyl groups are those having 8-22 carbon atoms and preferably those having 12-22 carbon atoms as well as those having 12-20 and those having 16-18 carbon atoms.

The term "cycloalkyl" refers to cyclic alkyl groups of from 3 to 22 carbon atoms having a single cyclic ring or multiple condensed rings. Cycloalkyl groups include those having 3-8 member rings and those having 5 and 6 member rings. Cycloalkyl groups include, by way of example, single ring structures such as cyclopropyl, cyclobutyl, cyclopentyl, cyclohexyl, cyclooctyl, and the like, or multiple ring structures such as adamantanyl, and the like.

The term "alkenyl" refers to a monoradical of a branched or unbranched unsaturated hydrocarbon group preferably having from 2 to 22 carbon atoms and to cycloalkenyl groups having one or more rings having 3 to 22 carbon atoms wherein at least one ring contains a double bond. Alkenyl groups may contain one or more double bonds (C=C) which may be conjugated. Preferred alkenyl groups are those having 1 or 2 double bonds. Short alkenyl groups are those having 2 to 6 carbon atoms including ethylene (vinyl) propylene, butylene, pentylene and hexylene groups, including all isomers thereof. Long alkenyl groups are those having 8-22 carbon atoms and preferably those having 12-22 carbon atoms as well as those having 12-20 carbon atoms and those having 16-18 carbon atoms. The term "cycloalkenyl" refers to cyclic alkenyl groups of from 3 to 22 carbon atoms having a single cyclic ring or multiple condensed rings in which at least one ring contains a double bond (C=C). Cycloalkenyl groups include, by way of example, single ring structures such as cyclopropenyl, cyclobutenyl, cyclopentenyl, cyclooctenyl, cylcooctadienyl and cyclooctatrienyl. The term allyl refers to the alkenyl group —CH$_2$—CH=CH$_2$.

The term "alkynyl" refers to a monoradical of an unsaturated hydrocarbon preferably having from 2 to 22 carbon atoms and having one or more triple bonds (C≡C). Alkynyl groups include ethynyl, propargyl, and the like. Short alkynyl groups are those having 2 to 6 carbon atoms, including all isomers thereof. Long alkynyl groups are those having 8-22 carbon atoms and preferably those having 12-22 carbon atoms as well as those having 12-20 carbon atoms and those having 16-18 carbon atoms.

The term "aryl" refers to a group containing an unsaturated aromatic carbocyclic group of from 6 to 22 carbon atoms having a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Aryls include phenyl, naphthyl and the like. Aryl groups may contain portions that are alkyl, alkenyl or akynyl in addition to the unsaturated aromatic ring(s). The term "alkaryl" refers to the aryl groups containing alkyl portions, i.e., -alkylene-aryl and -substituted alkylene-aryl). Such alkaryl groups are exemplified by benzyl (—CH$_2$-phenyl), phenethyl and the like.

Alkyl, alkenyl, alkynyl and aryl groups are optionally substituted as described herein (the term(s) can include substituted variations) and may contain 1-8 non-hydrogen substituents dependent upon the number of carbon atoms in the group and the degree of unsaturation of the group. All such variable as described herein can be unsubstituted (in which any variables groups that can be hydrogen are hydrogen) or substituted with one or more non-hydrogen substituents selected from halogen, including fluorine, chlorine, bromine or iodine, C1-C3 haloalkyl, hydroxyl (OH), thiol (HS—), C1-C6 alkyl, C1-C3 alkyl, C1-C6 alkoxy, C1-C3 alkoxy, phenyl, benzyl, alkenyl, C2-C4 alkenyl, alkynyl, C2-C4 alkynyl, —NH$_2$, —NR'H, —NR'R", R'CO—, R'R"NCO—, R'CO—NH—, or R'CO—NR'-, where R' and R" are C1-C6 alkyl, C1-C3 alkyl or phenyl.

The term "amino group" refers to the group —NH$_2$ or to the group —NR'R" where each R' and R" is independently selected from the group consisting of hydrogen, alkyl or aryl groups.

An alkoxy group is an alkyl group that has been modified by linkage to oxygen and can be represented by the formula R—O and may also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to CH$_3$O—.

"Haloalkyl" refers to alkyl as defined herein substituted by one or more halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "halo" or "halogen" refers to a halogen group such as a fluoro (—F), chloro (—Cl), bromo (—Br), iodo (—I) or astato (—At).

The term "heteroaryl" refers to an aromatic group of from 2 to 22 carbon atoms having 1 to 4 heteroatoms selected from oxygen, nitrogen and sulfur within at least one ring (if there is more than one ring). Heteroaryl groups may be optionally substituted. Heteroaryl groups include among others those having 5 and 6-member rings and those having one or two nitrogens in the ring, those having one or two oxygens in the ring as well as those having one or two sulfurs in the ring.

The term "heterocycle" or "heterocyclic" refers to a monoradical saturated or unsaturated group having a single ring or multiple condensed rings, from 2-22 carbon atoms and from 1 to 6 hetero atoms, preferably 1 to 4 heteroatoms, selected from nitrogen, sulfur, phosphorus, and/or oxygen within at least one ring. Heterocyclic groups may be substituted. Rings preferably have 3-10 members and more specifically have 5 or 6 members.

The term "ester" refers to chemical entities as understood in the art and in particular can include groups of the form (RCO—).

As to any of the above groups which contain one or more substituents, it is understood, that such groups do not contain any substitution or substitution patterns which are sterically impractical and/or synthetically non-feasible. The compounds of this invention include all novel stereochemical isomers arising from the substitution of disclosed compounds.

As is customary and well known in the art, hydrogen atoms in the formulas described herein are not always explicitly shown, for example, hydrogen atoms bonded to the carbon atoms of aromatic and alicyclic rings are not always explicitly shown in formulas. The structures provided herein, for example in the context of the description of the formulas, are intended to convey to one of reasonable skill in the art the chemical composition of compounds of the methods and compositions of the invention, and as will be understood by one of skill in the art, the structures provided do not indicate the specific bond angles between atoms of these compounds.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods and materials are now described. Nothing herein is to be construed as an admission that the invention is not entitled to antedate such disclosure by virtue of prior invention.

In some embodiments, a liposome or micelle may be utilized as a carrier or vehicle for the composition.

Every formulation or combination of components described or exemplified herein can be used to practice the invention, unless otherwise stated.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations may also include aerosol formulation, creams, gels, solutions, etc. The present compositions, preparations and formulations are administered in doses effective to achieve the desired diagnostic and/or therapeutic effect. Such doses may vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations may also optionally include stabilizing agents and skin penetration enhancing agents. A "patient" or "subject", used equivalently herein, refers to an animal. In particular, an animal refers to a mammal, preferably a human. The subject may either: (1) have a condition diagnosable, preventable and/or treatable by administration of a compound or composition of the invention; or (2) is susceptible to a condition that is diagnosable, preventable and/or treatable by administering a compound or composition of this invention.

In an embodiment, a composition of the invention is a chemotherapeutic agent.

In an embodiment, the invention provides compounds and methods involving effective concentrations preferably from about 10 nM to about 100 µM of the disclosed structural formulas. In another preferred embodiment, the effective concentrations are from about 200 nM to about 5 µM. In an embodiment, the effective concentration is considered to be a value such as a 50% activity concentration in a direct procaspase activation assay, in a cell apoptosis induction assay, or in an animal clinical therapeutic assessment. In a preferred embodiment, such value is less than about 200 µM. In a preferred embodiment, the value is less than about 10 µM.

Compounds of the invention and compounds useful in the methods of this invention include those of the disclosed formulas and salts and esters of those compounds, including preferably pharmaceutically-acceptable salts and esters.

In an embodiment, the invention provides prodrug forms of compositions. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. A biomolecule such as a precursor protein or precursor nucleic acid can be a prodrug. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

In an embodiment, a composition of the invention is in a form that is isolated or purified.

It is recognized that regardless of the ultimate correctness of any mechanistic explanation or hypothesis believed or disclosed herein, an embodiment of the invention can nonetheless be operative and useful.

When a group of substituents is disclosed herein, it is understood that all individual members of that group and all subgroups, including any isomers and enantiomers of the group members, are disclosed separately. When a Markush group or other grouping is used herein, all individual members of the group and all combinations and subcombinations possible of the group are intended to be individually included in the disclosure. It is intended that any one or more members of any Markush group or listing provided in the specification can be excluded from the invention if desired. When a compound is described herein such that a particular isomer or enantiomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Specific names of compounds are intended to be exemplary, as it is known that one of ordinary skill in the art can name the same compounds differently.

Molecules disclosed herein may contain one or more ionizable groups [groups from which a proton can be removed (e.g., —OH, —COOH, etc.) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. For example, in general any anions can be employed in the formation of salts of compounds herein; e.g. halide, sulfate, carboxylate, acetate, phosphate, nitrate, trifluoroacetate, glycolate, pyruvate, oxalate, malate, succinate, fumarate, tartarate, citrate, benzoate, methanesulfonate, ethanesulfonate, p-toluenesulfonate, salicylate and others.

Compounds of the present invention, and salts or esters thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, the compounds may have trans and cis isomers and may contain one or more chiral centers, therefore existing in enantiomeric and diastereomeric forms. The invention can encompass all such isomers, individual enantiomers, as well as mixtures of cis and trans isomers, mixtures of diastereomers; non-racemic and racemic mixtures of enantiomers (optical isomers); and the foregoing mixtures enriched for one or more forms; except as stated otherwise herein. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Every formulation or combination of components described or exemplified herein can be used to practice the invention, unless otherwise stated.

Whenever a range is described in the present application, for example, a temperature range, a time range, a log BB, or a composition or concentration range, all intermediate ranges and subranges, as well as all individual values included in the ranges given are intended to be included in the disclosure.

Information in any references disclosed herein can in some cases indicate the state of the art, for example for patent documents as of their effective filing dates; it is intended that such information can be employed herein, if needed, to exclude specific embodiments that are actually found to be in the prior art. For example, when a compound is disclosed and/or claimed, it should be understood that compounds qualifying as prior art with regard to the present invention, including compounds for which an enabling disclosure is provided in the references, are not intended to be included in the composition of matter claims herein.

Some references provided herein are incorporated by reference to provide details concerning sources of starting materials, additional starting materials, additional reagents, additional methods of synthesis, additional methods of analysis, and additional uses of the invention. One of ordinary skill in the art will appreciate that starting materials, reagents, solid substrates, synthetic methods, purification methods, and analytical methods other than those specifically exemplified can be employed in the practice of the invention based on knowledge in the art and without resort to undue experimentation.

The invention may be further understood by the following non-limiting examples.

Example 1

PAC-1 and Personalized Anticancer Therapy

As discussed further herein, apoptosis is a type of programmed cell death common in multicellular organisms. Evasion of apoptosis is a hallmark of cancer and many cancers are resistant to natural apoptotic signals. This resistance is most often due to the aberrant expression and mutation of upstream apoptotic proteins which prevent the proper transmission of proapoptotic signals to downstream cysteine-aspartic acid proteases, the caspases. Ultimately, the activation of the executioner caspase-3 is the key committed step in most apoptotic pathways. Surprisingly, procaspase-3 is upregulated in many cancers but alterations in the upstream apoptotic cascade prevent it from being activated.

A number of proapoptotic compounds have been developed to target apoptotic proteins upstream of caspase-3. However, the aforementioned roadblocks often prevent these compounds from having their desired proapoptotic effect in cancerous cells. A personalized and more effective anticancer strategy involves the direct activation of proapoptotic proteins downstream of any roadblocks in the cascade. FIG. 1 shows some aspects of small molecule activation of procaspase-3.

We have reported PAC-1 as a small molecule that directly activates procaspase-3 to caspase-3 in vitro and in many cancer cell lines, inducing apoptosis in cancerous cells (Nat. Chem. Biol. 2006, 2, 543-550). PAC-1 has also shown efficacy in multiple mouse models of cancers.

Mutations and aberrant expression of upstream apoptotic proteins prevent pro-apoptotic signals from reaching downstream effector caspases. The key executioner, procaspase-3 is upregulated in many cancers. Much effort has been expended in the goal of a small molecule capable of directly activating procaspase-3. Some of this effort is described here as a further background for the present invention.

Scheme 1 shows an exemplary high Throughput Screening for Procaspase-3 Activator.

Scheme 1

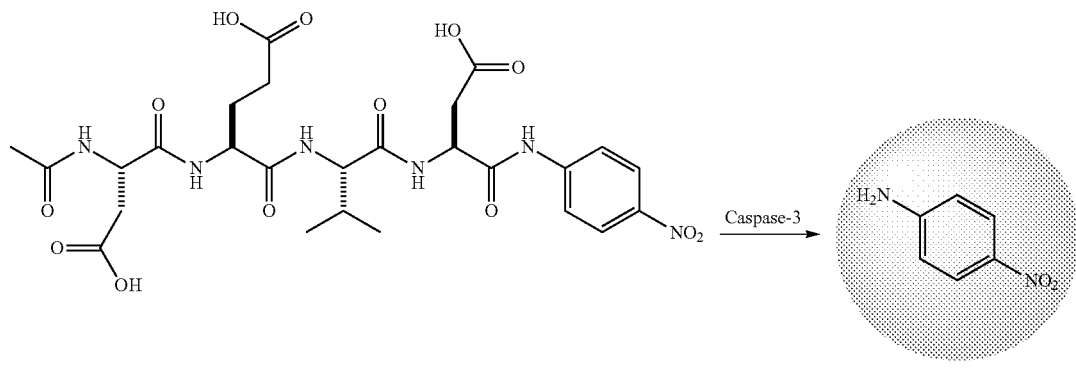

$\lambda_{max} = 405$ nm

~20,000 compounds were screened with a chromogenic substrate for their ability to activate procaspase-3 to active caspase-3. PAC-1 was identified as a compound capable of activating procaspase-3 in a dose dependent manner. PAC-1-I-8 is a structurally related compound that shows no activity.

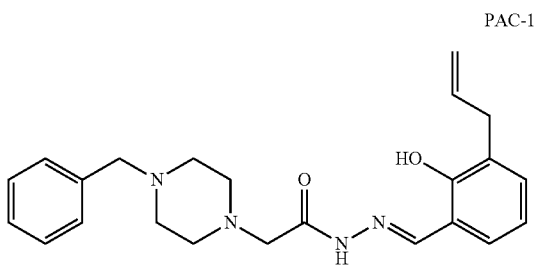 [SMILES: C=CCc1cccc(/C=N/NC(=O)CN2CCN(Cc3ccccc3)CC2)c1O]

PAC-1

Figure 2:
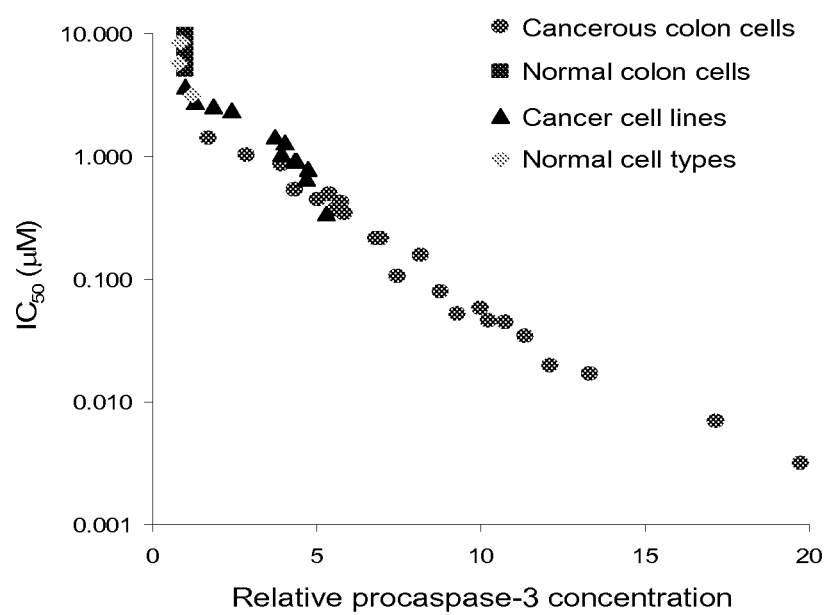
FIG. 2 shows PAC-1 selectively kills a variety of cancer cells.

FIG. 2 shows that PAC-1 Selectively Kills Cancer Cells. PAC-1 induces death in cells isolated from freshly resected colon tumors. Freshly resected primary colon tumors (together with adjacent noncancerous tissue) were obtained from 23 people, the cancerous and noncancerous tissue were separated. PAC-1 induces cell death in a manner proportional to the cellular concentration of procaspase-3. The circles represent the primary cancerous cells from the 23 colon tumors. The black triangles represent a variety of cancer cell lines. The diamonds are four noncancerous cell types: Hs888Lu (lung fibroblast cells), MCF-10A (breast fibroblast cells), Hs578Bst (breast epithelial cells) and white blood cells isolated from the bone marrow of a healthy donor. The squares are the primary noncancerous cells isolated from the tumor margins of the 23 people.

Figure 3:
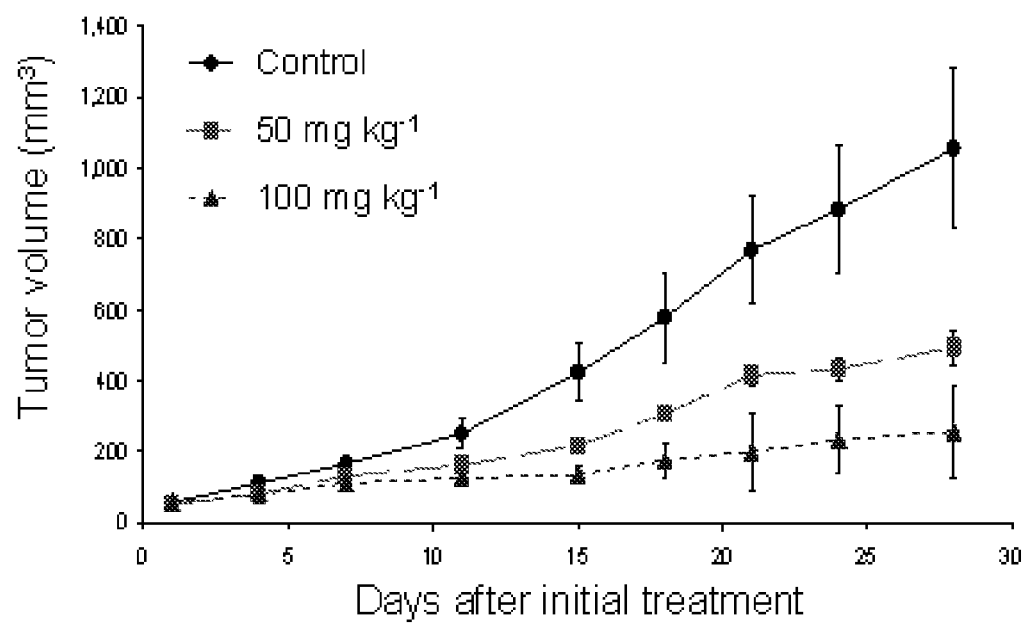
FIG. 3 shows PAC-1 retardation of tumor growth in mouse xenograft models of cancer.
Figure 4:
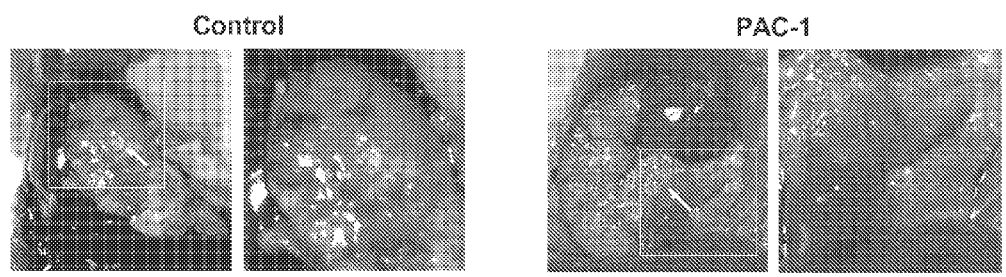
FIG. 4 shows PAC-1 retardation of tumor growth in mice.

FIGS. 3 and 4 show PAC-1 retardation of tumor growth in mouse xenograft models of cancer. (Putt, et al. *Nat. Chem. Biol.* 2006, 2, 543-550.) For FIG. 3, tumors were formed in mice using the NCI-H226 (lung cancer) cell line by subcutaneous injection, with eight mice in each group and three tumors per mouse. PAC-1 or vehicle was administered once a day by oral gavage on days 1-21. Error bars are s.e.m. For FIG. 4, Mice were injected with the NCI-H226 cell line. The mice were treated with PAC-1 (100 mg kg-1) via oral gavage following the protocol described in (Putt, et al. *Nat. Chem. Biol.* 2006, 2, 543-550.). The lungs of control mice have a large amount of gray tumor mass, whereas the mice that received PAC-1 have almost no visible tumor.

Figure 5:
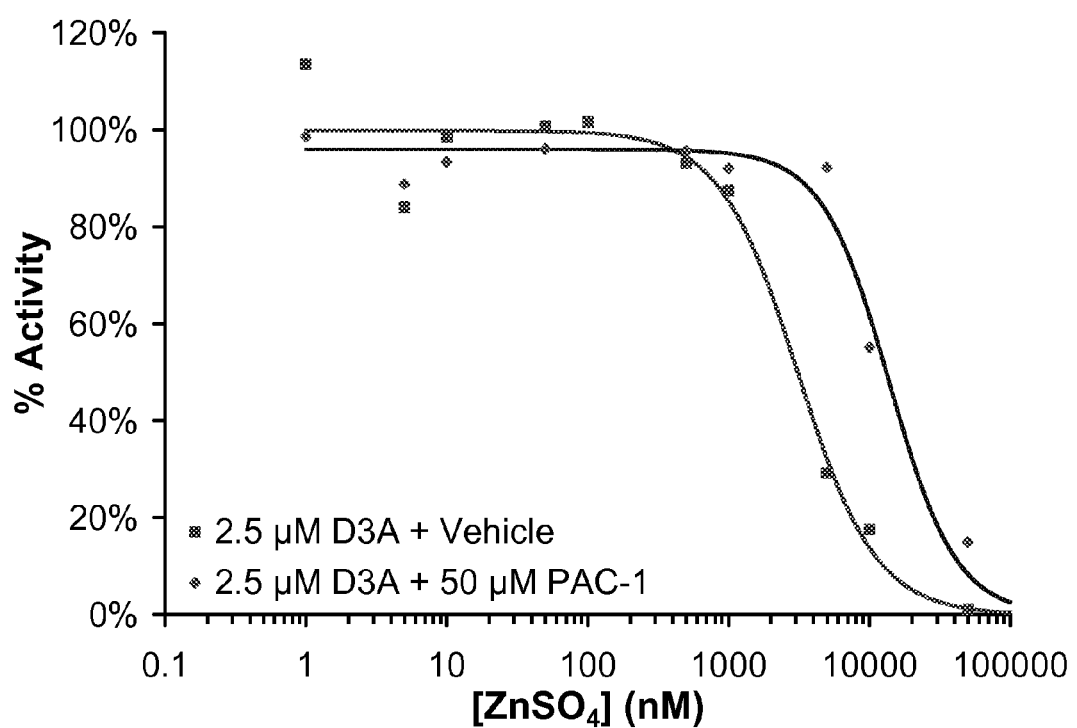
FIG. 5 shows PAC-1 Relieves $Zn^{2+}$ Inhibition of Procaspase-3. As assessed by the cleavage of the Ac-DEVD-pNA substrate, the ability of zinc to inhibit the procaspase-3(D9A/D28A/D175A) mutant (D3A, 2.5 µM) activity in vitro is reduced in the presence of PAC-1 (50 µM). Data shown is representative of three trials.
Figure 6:
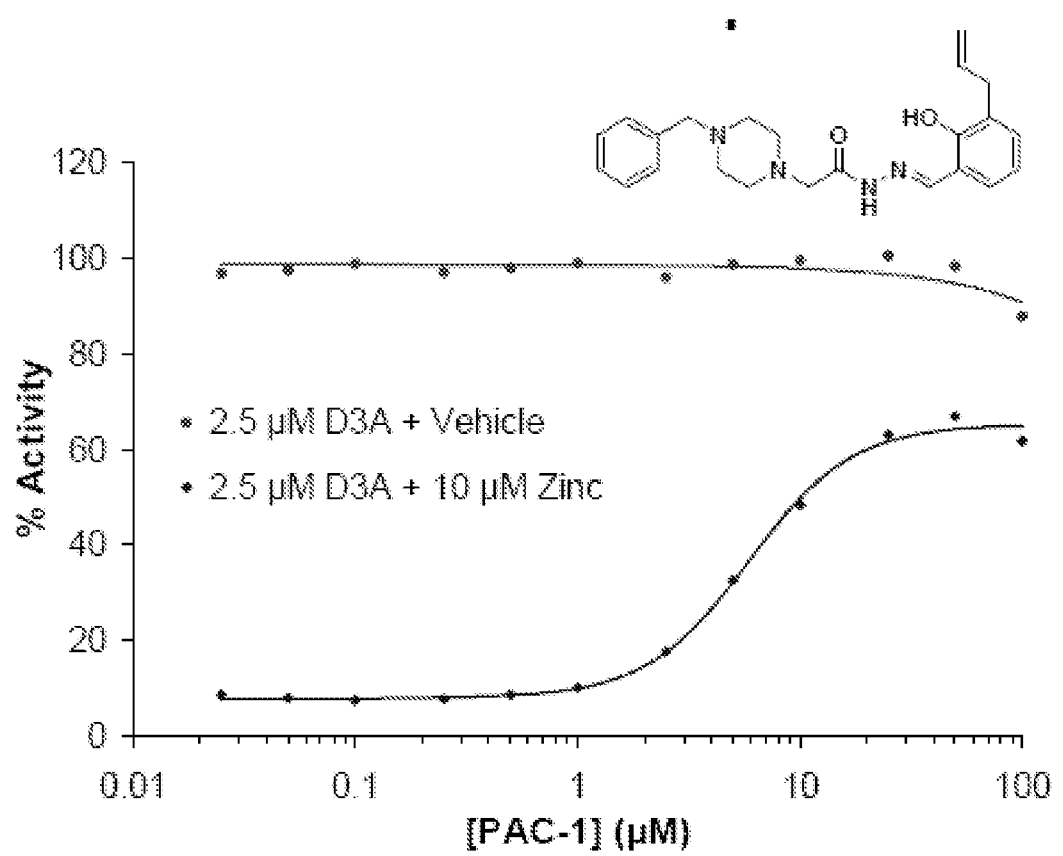
FIG. 6 shows PAC-1 enhances the procaspase-3(D9A/D28A/D175A) (D3A) mutant activity when assayed in a buffer containing 10 µM ZnSO4.
Figure 7:
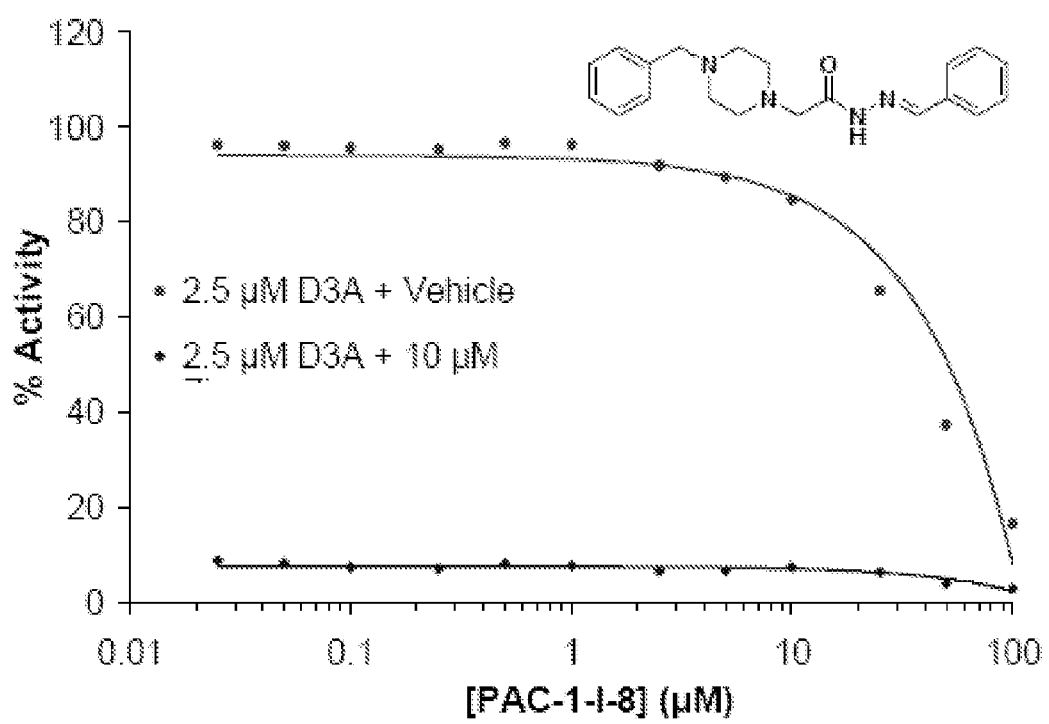
FIG. 7 shows PAC-1-I-8 enhances the procaspase-3(D9A/D28A/D175A) (D3A) mutant activity when assayed in a buffer containing 10 µM $ZnSO_4$.

Zinc ions are known to inhibit procaspase-3. PAC-1 is able to activate procaspase-3 in the presence of zinc in a dose-dependent manner and shift the IC50 of zinc inhibition. PAC-1-I-8 is not able to activate procaspase-3, but shows inhibition at high concentrations. FIGS. 5, 6 and 7 show PAC-1 relieves Zn2+ Inhibition of Procaspase-3. The effect of a range of concentrations of zinc on caspase-3 and procaspase-3 enzymatic activity was examined. All buffers were first treated with Chelex® resin to remove any trace metal contaminants. As procaspase-3 will slowly autoproteolyze itself to active caspase-3, created the triple mutant of procaspase-3 in which all three caspase cleavage sites have been removed (D9A/D28A/D175A) was created, Consistent with data in the literature, this procaspase-3 triple mutant is proteolytically stable and has activity ~200-fold less than that of caspase-3 (data not shown). Enzyme assays in the presence of zinc indicate that this metal powerfully inhibits caspase-3 (data not shown), procaspase-3 (data not shown), and the procaspase-3(D9A/D28A/D175A) mutant (FIG. 5). FIG. 6 shows PAC-1 enhances the procaspase-3(D9A/D28A/D175A) (D3A) mutant activity when assayed in a buffer containing 10 µM ZnSO4. As shown, PAC-1 actually inhibits these three enzymes at high compound concentrations. Data shown is representative of three trials. FIG. 7 shows PAC-1-I-8 enhances the procaspase-3(D9A/D28A/D175A) (D3A) mutant activity when assayed in a buffer containing 10 µM ZnSO4. PAC-1-I-8 actually inhibits this enzyme at high compound concentrations even in the absence of ZnSO4.

Figure 8:
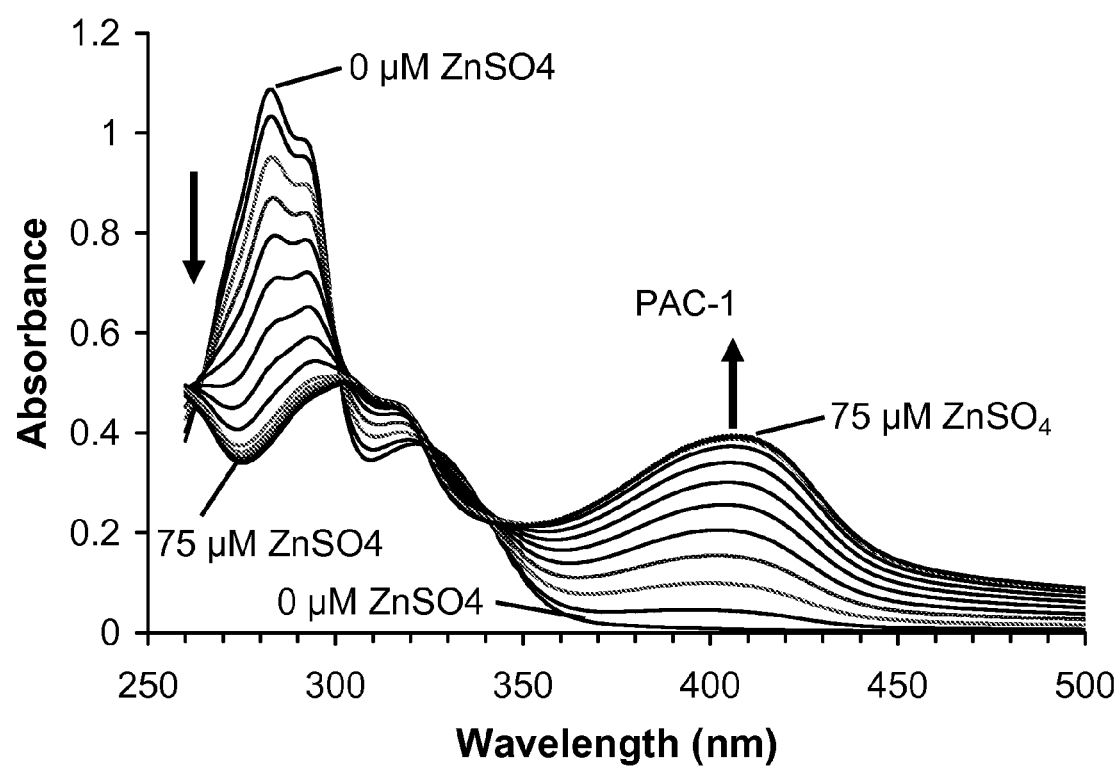
FIG. 8 shows titration of ZnSO4 into a solution of PAC-1 (50 µM in 50 mM Hepes, 100 mM KNO3, pH 7.2 buffer) causes a change in the UV-visible spectra of PAC-1. Shown are ZnSO4 concentrations of 0 to 75 µM in 5 µM increments.
Figure 9:
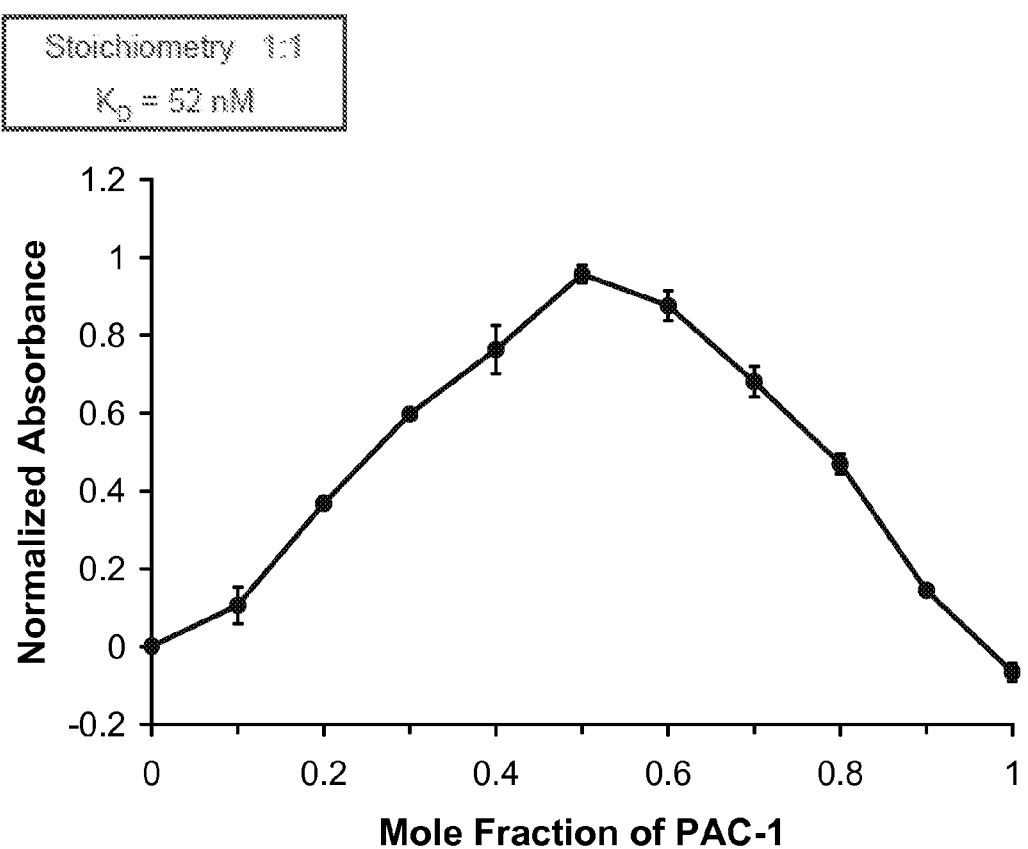
FIG. 9 shows analysis of the PAC-1-$Zn^{2+}$ binding interaction and stoichiometry by the continuous variations method. Based on the location of the peak value, the stoichiometry was determined to be 1:1, and the Kd was determined to be 42 nM. Error bars represent standard deviation from the mean.
Figure 10:
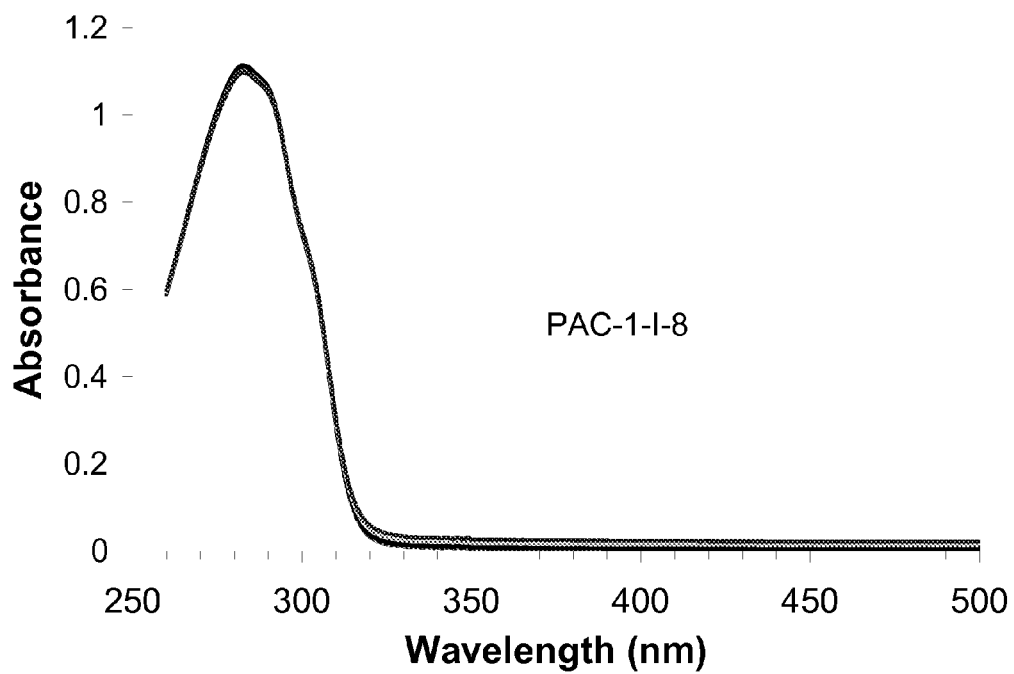
FIG. 10 shows a titration of ZnSO4 into a solution of PAC-1-I-8 (50 µM in 50 mM Hepes, 100 mM KNO3, pH 7.2 buffer) does not cause a change in the UV-visible spectra of PAC-1-I-8.

FIGS. 8, 9 and 10 show PAC-1 is a metal chelator. In the presence of zinc, PAC-1 shows a characteristic increase in absorbance at 405 nm. The inactive derivative does not show any change in absorbance even at high concentrations of zinc. Using this absorbance shift the binding constant for the PAC-1:Zn2+ complex can be determined by the continuous variation method. As shown in FIG. 8, titration of PAC-1 with increasing amounts of ZnSO4 results in a change in the UV-visible spectrum of this compound. This shift in molar absorptivity upon Zn2+ binding provides a convenient method to determine both the stoichiometry of PAC-1-Zn2+ binding and the dissociation constant of this interaction. A modified version of the method of continuous variations was used for this determination. The absorbance at 410 nm was acquired for various mole fractions of ZnSO4 and PAC-1 with a total concentration of 50 µM. These values were then normalized versus the maximal absorbance possible at the stoichiometric point (i.e., when all of the Zn2+ is bound by excess PAC-1), which was set as 1. Application of the continuous variations method revealed that PAC-1 binds Zn2+ in a 1:1 stoichiometry, as evidenced by the peak at 0.5 mol fraction in the graph in FIG. 9. Also apparent from FIG. 9 is the very strong nature of this small molecule-metal interaction. At the 1:1 stoichiometry, PAC-1 has almost entirely shifted its absorption to the zinc-bound state (96% of PAC-1 is Zn2+ bound at a 1:1 ratio of PAC-1-Zn2+). Using this 96% value and the equation log Ka=0.3010–log M+log ymax–2 log (1–ymax), we obtain a Kd=42 nM for the PAC-1-Zn2+ interaction. While the Kd for the PAC-1-Zn2+ interaction is 42 nM, as shown in FIG. 8, an absorbance change is still observed with micromolar concentrations of zinc. This is due to the high concentration of total ligand (50 µM) in this experiment relative to the Kd. Based on the concentrations of zinc and PAC-1 utilized in this experiment, the Adair equation predicts a half maximal population average site occupancy for the PAC-1-Zn2+ complex at ~30 µM zinc, consistent with the data obtained (FIG. 8). Titration of ZnSO4 into PAC-1-I-8 gave no spectral change as monitored by UV-vis spectroscopy, consistent with the notion that PAC-1-8 does not bind Zn2+. To confirm this result, a second method was used to determine the PAC-1-Zn2+ dissociation constant. In this experiment, a preformed complex of PAC-1 and Zn2+ was titrated with EGTA [ethylene glycol bis(β-aminoethyl ether) N,N'-tetraacetic acid, a metal binder with a known affinity for Zn2+], and the absorbance at 410 nm was monitored. Using the literature value for the EGTA-Zn2+ association constant, we calculated the PAC-1-Zn2+ dissociation constant as 55 nM, in general agreement with Kd of 42 nM calculated through the method of continuous variations. FIG. 10 shows titration of ZnSO4 into a solution of PAC-1-I-8 (50 µM in 50 mM Hepes, 100 mM KNO3, pH 7.2 buffer) does not cause a change in the UV-visible spectra of PAC-1-I-8. Shown are ZnSO4 concentrations of 0 to 70 µM in 5 µM increments.

Example 2

Syntheses of PAC-1 and Derivatives

Figure 15:
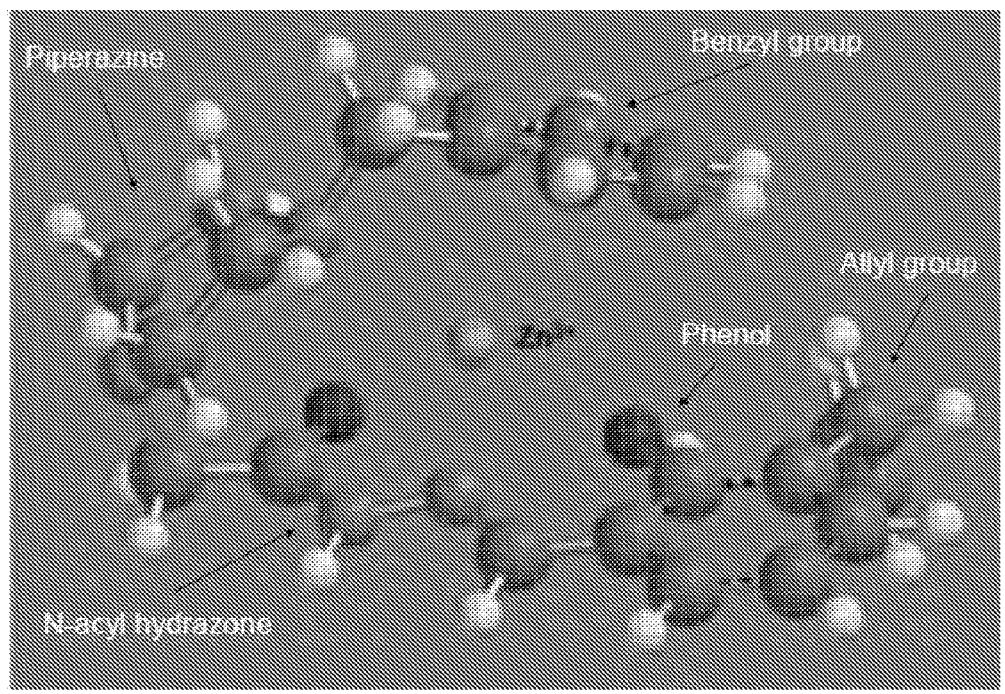
FIG. 15 shows the lowest energy conformer of the PAC-1-$Zn^{2+}$ complex.

Molecular modeling resulted in the lowest energy conformer of the PAC-1-Zn2+ complex shown in FIG. 15. This structure was obtained from a conformational search out of 23 low-energy conformers using MMFF force field. The model suggests interaction with the N-acyl hydrazone backbone, the phenolic hydroxyl and a cation-pi interaction with the benzyl ring.

A family of structurally modified PAC-1 derivatives was synthesized to investigate these structural components and their role in zinc binding and the cytotoxic potential of this family of compounds.

Four classes of derivatives were synthesized to investigate the phenolic position (class I), the benzyl group (class II), the combination of these rings (class III) and the N-acyl hydrazone backbone (class IV). These classes are shown above in Scheme 2.

Scheme 2

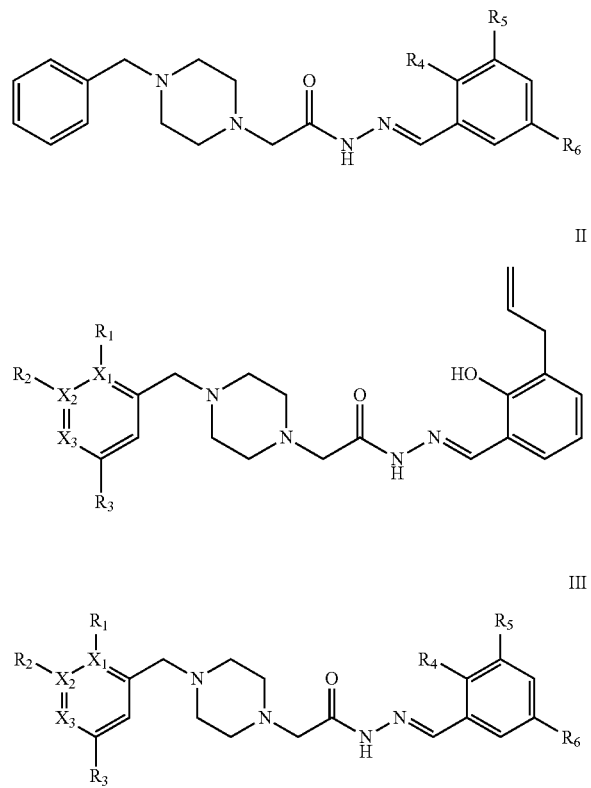

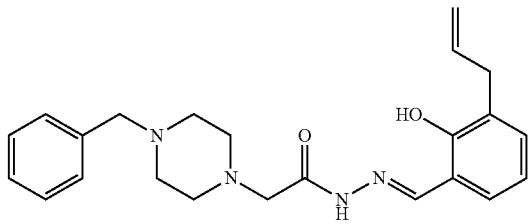

Additional information about these compounds and classes is found in: Peterson, et al., J. Med. Chem. 2009, 52, 5721-5731. The majority of the Class I-III compounds were synthesized as shown in Scheme 3A, via condensation of the appropriate hydrazides and aldehydes. As shown in Scheme 3A, yields for this condensation were between 72 and 95%, the exception being 1 g, which spontaneously forms a disulfide dimer, resulting in a diminished yield. Through such condensation reactions, 11 Class I derivatives (1a-k), 7 Class II derivatives (2a-g), and 1 Class III derivative (3) were synthesized. The hydrazide building blocks in Scheme 1 were synthesized through the reaction of various benzyl chlorides with piperazine, alkylation of the resulting products with ethyl chloroacetate, followed by reaction of the resulting ester with hydrazine. The aldehyde building blocks were either purchased or synthesized from simple starting materials. Three Class IV derivatives could also be synthesized through analogous condensation reactions. Thus, compounds lacking one of two piperazine nitrogens (4a-c) were synthesized from the corresponding hydrazides and aldehyde as shown in Scheme 3, eqs 1 and 2. However, a number of the derivatives in Class IV could not be synthesized via analogous condensation reactions and required alternative synthetic routes. Thus, compound 4d was synthesized by reduction of the hydrazone in PAC-1 using NaCNBH3 (Scheme 4A, eq 3). Compounds 4e-g were synthesized through the reaction of 27 with the appropriate chloride (Scheme 4A, eqs 4-6). These classes probe the electronics of these ring systems as well as the coordinating heteroatoms involved in the complex.

Scheme 3. Synthesis of PAC-1

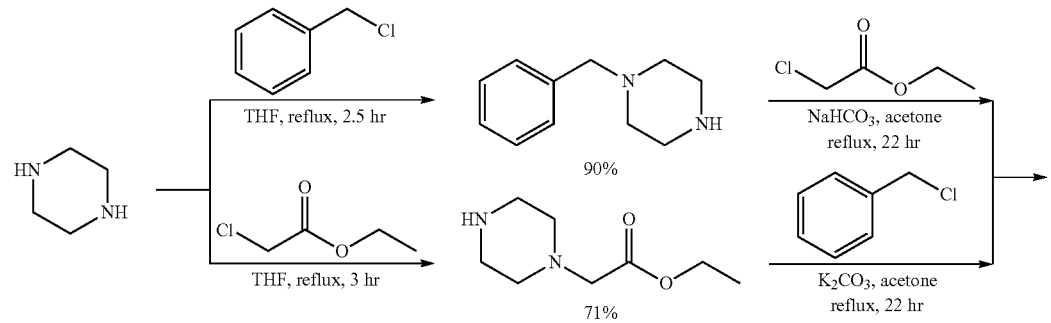

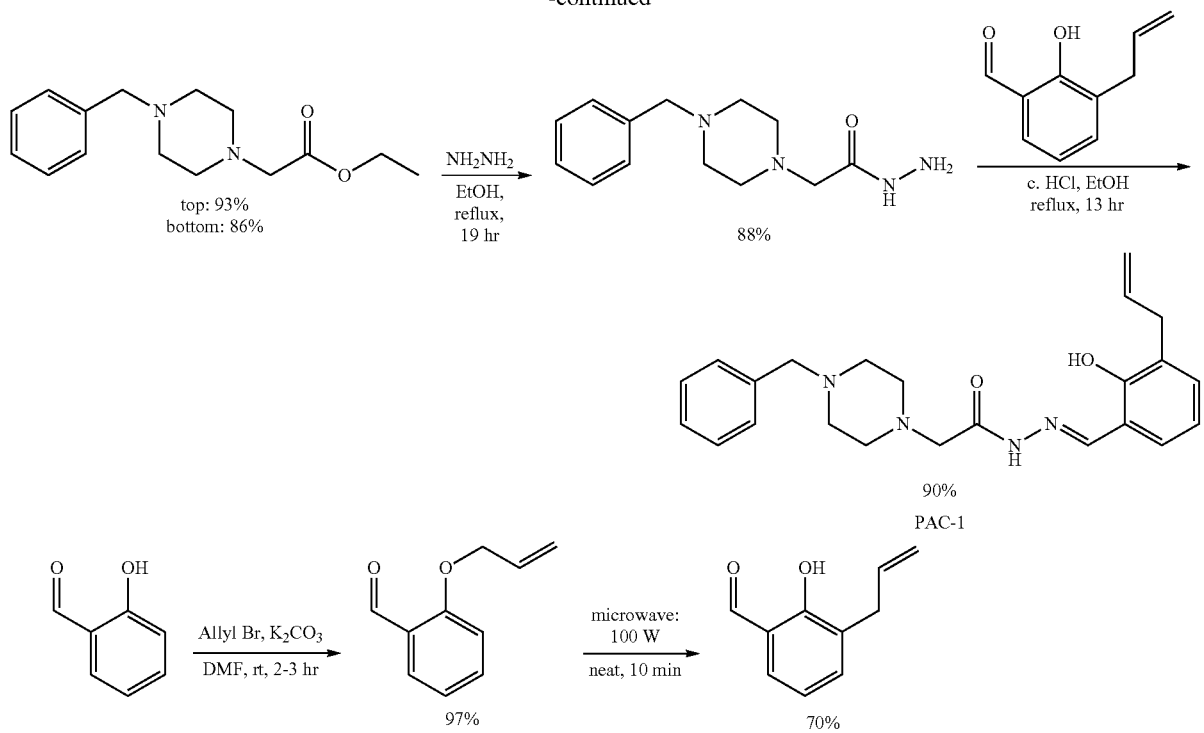

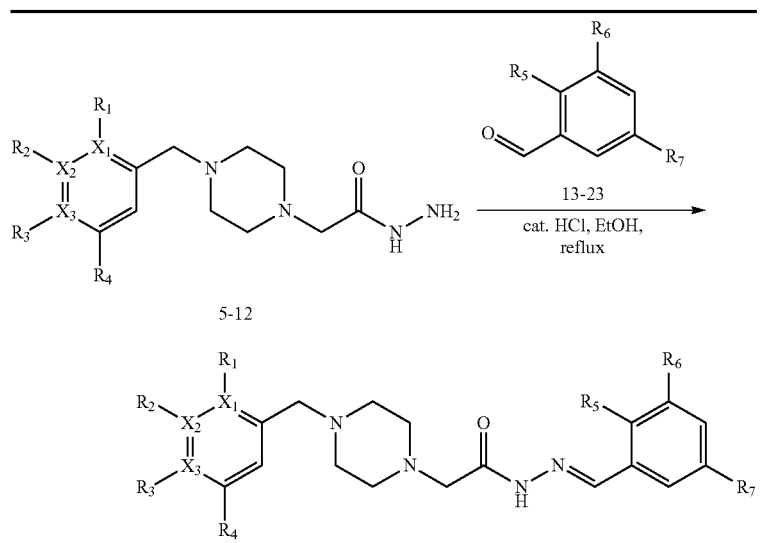

With substituent alternation at both rings, class I-III PAC-1 derivatives were synthesized with the same route as shown in Scheme 3A:

| Hydrazide | Aldehyde | Product | Yield |
|---|---|---|---|
| 5. $R_1, R_2, R_3, R_4 = H, X_1, X_2, X_3 = C$ | 13. $R_5 = OH, R_6 = Allyl, R_7 = H$ | 1 | 95% |
| 5. $R_1, R_2, R_3, R_4 = H, X_1, X_2, X_3 = C$ | 14. $R_5 = OH, R_6, R_7 = H$ | 1a | 72% |
| 5. $R_1, R_2, R_3, R_4 = H, X_1, X_2, X_3 = C$ | 15. $R_5 = MeS, R_6, R_7 = H$ | 1b | 88% |
| 5. $R_1, R_2, R_3, R_4 = H, X_1, X_2, X_3 = C$ | 16. $R_5 = NH_2, R_6, R_7 = H$ | 1c | 78% |
| 5. $R_1, R_2, R_3, R_4 = H, X_1, X_2, X_3 = C$ | 17. $R_5 = COOH, R_6, R_7 = H$ | 1d | 79% |
| 5. $R_1, R_2, R_3, R_4 = H, X_1, X_2, X_3 = C$ | 18. $R_5 = CO_2Me, R_6, R_7 = H$ | 1e | 72% |
| 5. $R_1, R_2, R_3, R_4 = H, X_1, X_2, X_3 = C$ | 19. $R_5 = Cl, R_6, R_7 = H$ | 1f | 94% |
| 5. $R_1, R_2, R_3, R_4 = H, X_1, X_2, X_3 = C$ | 20. $R_5 = SH, R_6, R_7 = H$ | 1g | 18% |
| 5. $R_1, R_2, R_3, R_4 = H, X_1, X_2, X_3 = C$ | 21. $R_5, R_6, R_7 = H$ | 1h | 75% |
| 5. $R_1, R_2, R_3, R_4 = H, X_1, X_2, X_3 = C$ | 22. $R_5 = OH, R_6 = Allyl, R_7$ Allyl | 1j | 93% |

-continued

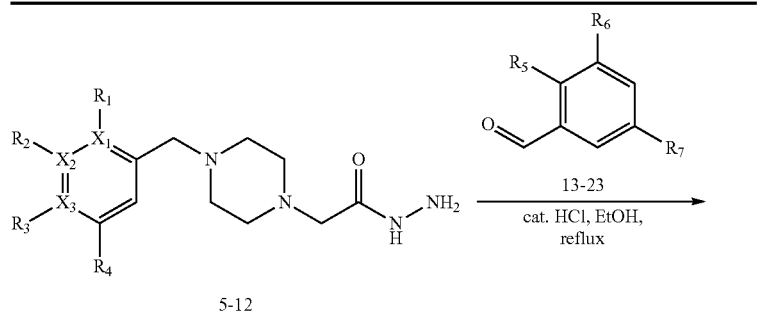

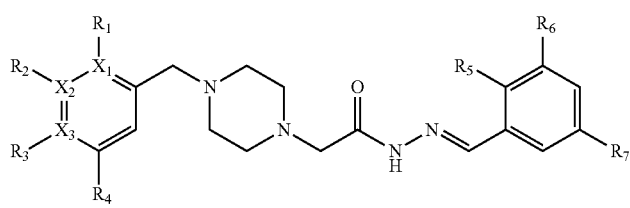

| Hydrazide | Aldehyde | Product | Yield |
|---|---|---|---|
| 5. $R_1, R_2, R_3, R_4 = H, X_1, X_2, X_3 = C$ | 23. $R_5 = OMe, R_6 = Allyl, R_7 = H$ | 1k | 85% |
| 6. $R_1, R_2, R_3, R_4 = H, X_1 = N, X_2, X_3 = C$ | 13. $R_5 = OH, R_6 = Allyl, R_7 = H$ | 2a | 83% |
| 7. $R_1, R_2, R_3, R_4 = H, X_1 = C, X_2 = N, X_3 = C$ | 13. $R_5 = OH, R_6 = Allyl, R_7 = H$ | 2b | 88% |
| 8. $R_1, R_2, R_3, R_4 = H, X_1, X_2 = C, X_3 = N$ | 13. $R_5 = OH, R_6 = Allyl, R_7 = H$ | 2c | 90% |
| 9. $R_1, R_2 = H, R_3 = F, R_4 = H, X_1, X_2, X_3 = C$ | 13. $R_5 = OH, R_6 = Allyl, R_7 = H$ | 2d | —* |
| 10. $R_1 = OMe, R_2, R_3 = H, R_4 = OMe, X_1, X_2, X_3 = C$ | 13. $R_5 = OH, R_6 = Allyl, R_7 = H$ | 2e | 80% |
| 11. $R_1, R_2 = H, R_3 = OMe, R_4 = H, X_1, X_2, X_3 = C$ | 13. $R_5 = OH, R_6 = Allyl, R_7 = H$ | 2f | 81% |
| 12. $R_1 = H, R_2 = NO_2, R_3, R_4 = H, X_1, X_2, X_3 = C$ | 13. $R_5 = OH, R_6 = Allyl, R_7 = H$ | 2g | 74% |
| 10. $R_1 = OMe, R_2, R_3 = H, R_4 = OMe, X_1, X_2, X_3 = C$ | 14. $R_5 = OH, R_6, R_7 = H$ | 3 | 82% |

Scheme 3A. Note the "R" variables are provided for this scheme and the usage is not necessarily the same as in the remainder of the disclosure. All such variations throughout the disclosure are easily understood by one of ordinary skill in the art.

Class IV compounds were synthesized with slight modification as shown below.

Scheme 4. Synthesis of class IV compounds.

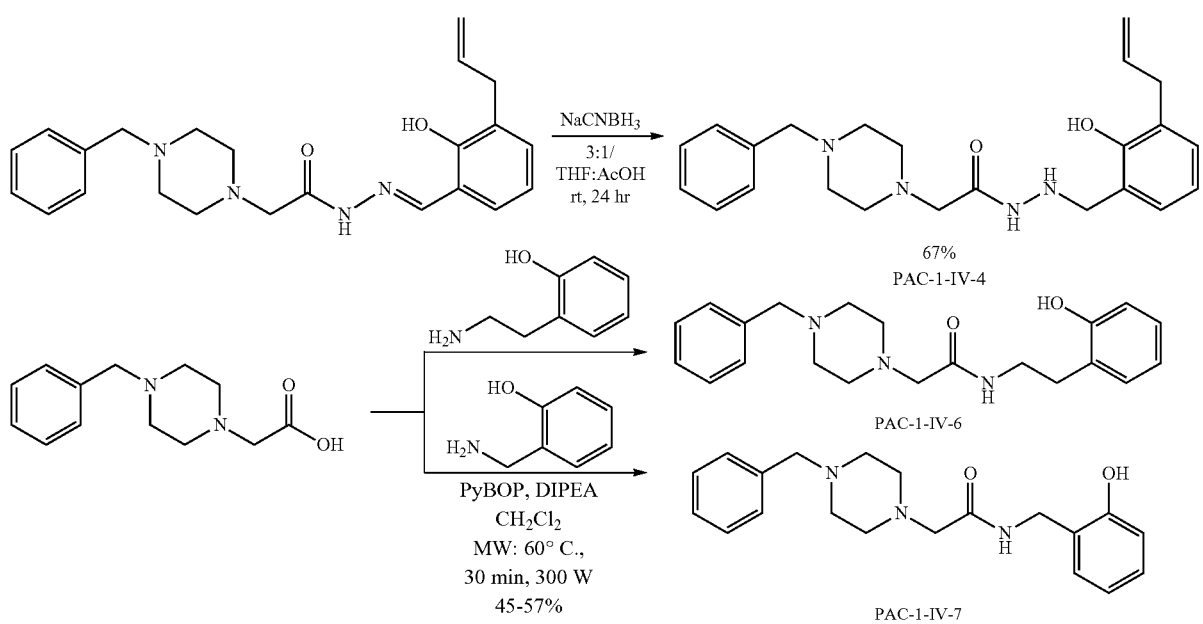

Some additional class IV compounds were synthesized using the method shown in Scheme 4A.
Scheme 4A.
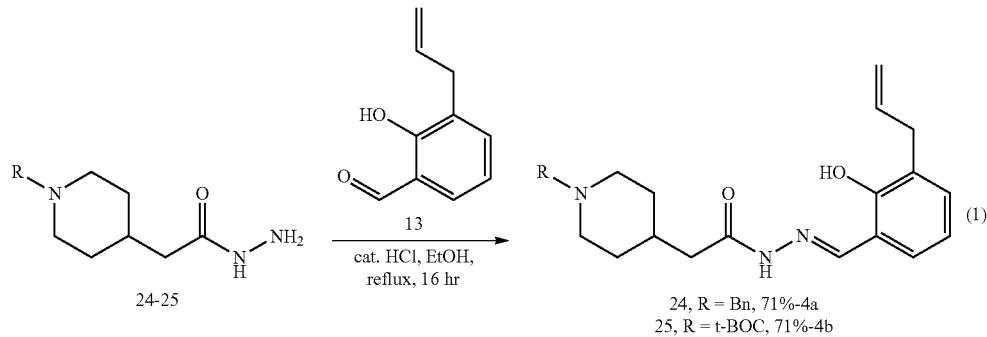
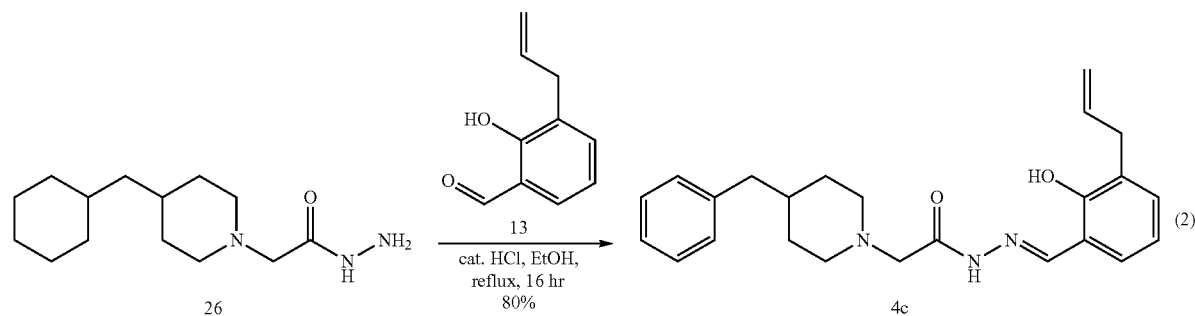
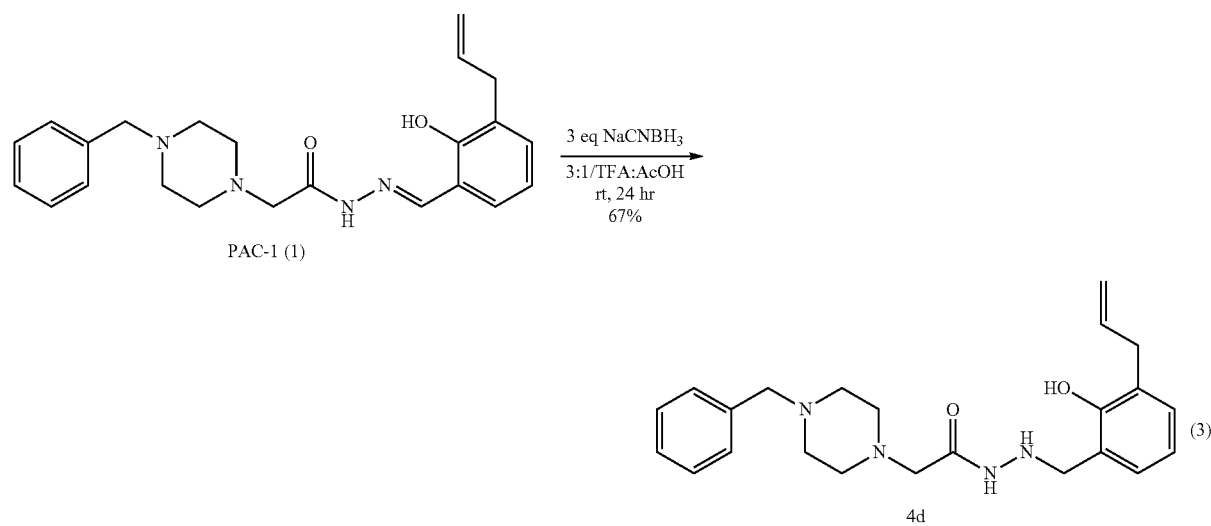

-continued

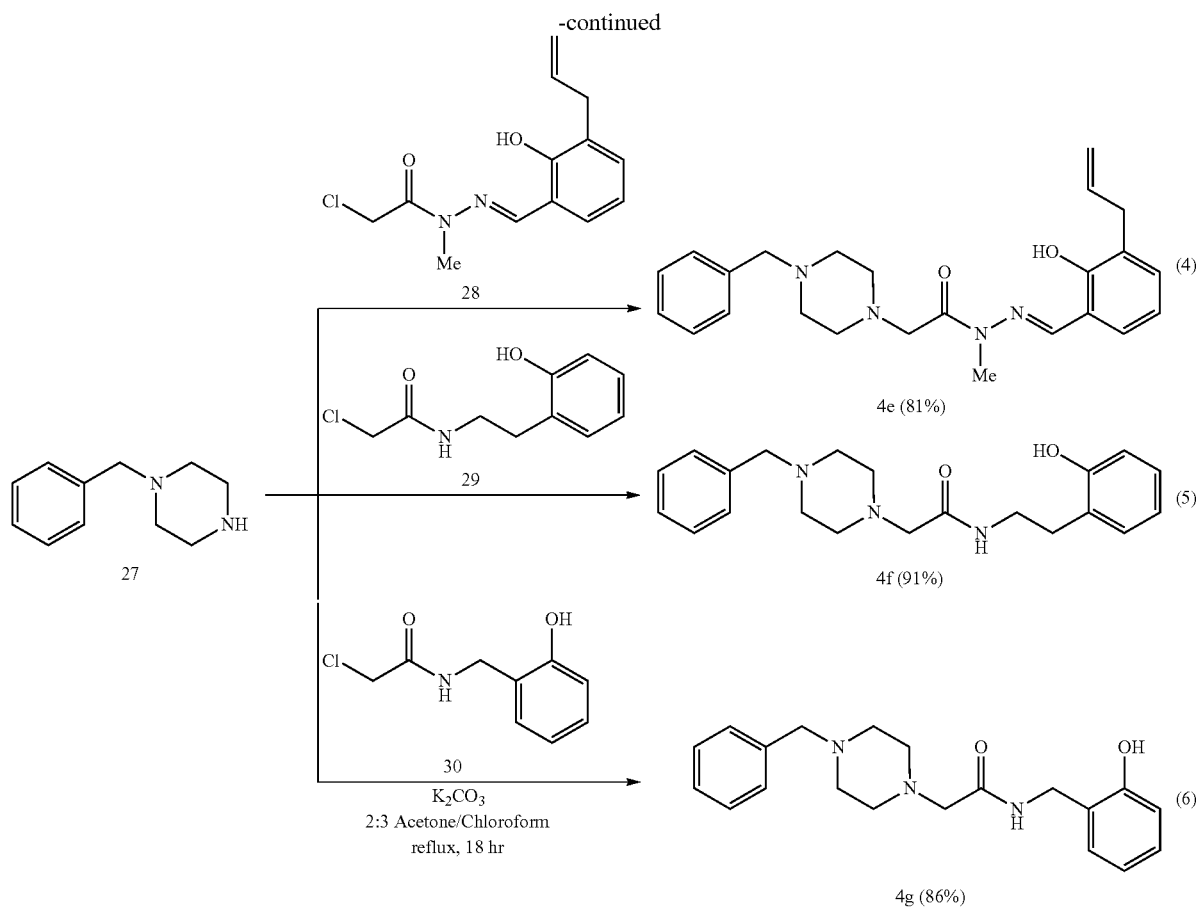

Synthetic methods for the four classes of compounds are provided here. Materials—All reagents were obtained from Fisher unless otherwise indicated. All buffers were made with MilliQ purified water. Ac-DEVD-pNA was synthesized. Luria broth (LB) was obtained from EMD. Etoposide was obtained from Sigma. Caspase Activity Buffer contains 50 mM Hepes (pH 7.4), 300 mM NaCl and is Chelex® treated. Ni NTA binding buffer contains 50 mM Tris (pH 8.0), 300 mM NaCl, and 10 mM imidazole. Ni NTA Wash Buffer contains 50 mM Tris (pH 8.0), 300 mM NaCl, and 20 mM imidazole. Ni NTA Elution Buffer contains 50 mM Tris (pH 8.0), 300 mM NaCl, and 500 mM imidazole. Annexin V Binding Buffere contains 10 mM HEPES pH 7.4, 140 mM NaCl, 2.5 mM CaCl2, 0.1% BSA. The C-terminal 6×His-tagged procaspase-3 proteins were expressed as described below.

Cell Culture—U937 human lymphoma cells and SK-MeI-5 human melanoma cells were obtained from ATCC. Cells were cultured in RPMI 1640 growth media supplemented with 10% FBS and 1% pen-strep. Cells were incubated at 37° C. and 5% CO2. Subculture of SK-MeI-5 cells was achieved through trypsinization of the cell monolayer using 0.05% Trysin-EDTA (Gibco) dilution and further culture in RPMI 1640 growth media supplemented with FBS and pen-strep as above.

Cell Death Assay—U937 human lymphoma cells were plated into the wells of 96 well plate at a density of 5000 cells per well in 200 μL of RPMI 1640 growth media with 10% FBS and 1% pen-strep. To each well was added 2 μL of 100× compound stock solutions in DMSO at varying concentrations so that the cells were treated with concentrations between 0 μM and 100 μM compound. Each concentration was tested in quintuplicate. In each plate 5 wells received 10 μM etoposide as a positive control and 5 wells received 2 μL of DMSO as a negative control. The plates were then incubated at 37° C. and 5% CO2 for 72 hours. After the 72 hour incubation period, the plates were analyzed using a Sulforhodamine B assay as previously described. 1 Specifically, to each well of the plate was added 50 μL of an 80% (w/v) solution of TCA in H2O and the plates were allowed to rest at 4° C. overnight. The plates were then washed gently with a steam of H2O five times to remove the excess TCA and precipitated serum proteins. The plates were then allowed to air dry after which 100 μL of a 0.057% (w/v) Sulforhodamine B in a 1% (v/v) acetic acid solution was added to each well and allowed to stain for 30 minutes at room temperature. After staining, the wells were gently washed 5 times with 100 μL of 1% (v/v) acetic acid to remove the unbound dye. The plates were then allowed to air dry. 200 μL of 10 mM Tris base (pH 10.5) was then added to each well and the plates were placed on an orbital shaker for five minutes. The OD was then read at 510 nm in a Molecular Dynamics plate reader and the percent cell death calculated and normalized to the positive control (100% cell death) and the negative control (0% cell death). The percent cell death was averaged for each compound concentration and plotted as a function of compound concentration. The data were fit to a logistical dose response curve using Table curve 2D and the IC50 value was calculated. The experiment was repeated three times and the average of the calculated IC50 values was reported. The standard error of the mean (SEM) was determined and reported for the triplicate experiments. The individual dose-response curves are not shown.

Recombinant expression and purification of procaspase-3/caspase-3—Procaspase-3 and caspase-3 were recombinantly expressed and purified exactly as previously described. Briefly, procaspase-3 and caspase-3 were expressed from the pHC332 expression plasmid in the electrocompetent BL21 (DE3) strain of *Escherichia coli* (Novagen). The C-terminally 6×His-tagged protein was purified using the Ni NTA resin (Qiagen). Protein containing fractions were collected and pooled. The purified protein was then further purified to remove any contaminating zinc by applying the protein to a PD-10 column (GE Healthcare) charged with Caspase Activity Buffer that had been treated with Chelex® resin. The resulting zinc free, protein containing fractions in Caspase Activity Buffer were pooled, the concentration determined, and the protein solution was flash-frozen in liquid nitrogen and stored at −80° C.

Caspase-3 Activity Assays—Zinc-free stocks (2×) of caspase-3 (1 μM) were prepared in Caspase Activity Buffer. Compound stock solutions were made (2×) at various concentrations from 200 μM to 200 nM in Caspase Activity Buffer. A stock (10×) of ZnSO4 (25 μM) in Caspase Activity Buffer was prepared. To each well of 384 well plate was added 20 μL of caspase-3 (500 nM final), 20 μL compound stock, and 5 μL of ZnSO4 (2.5 μM final) or buffer. Each plate contained positive control wells (0 μM zinc and no compound) and negative control wells (2.5 μM zinc and no compound). The plates were incubated at room temperature for 30 minutes. Then, to each well of the plate was added 5 μL of a 2 mM stock of Ac-DEVD-pNA substrate and the absorbance at 405 nm was immediately monitored every 1 minute for 30 minutes on a spectramax plate reader (Molecular Devices, Sunny Vale, Calif.). The slope of each well was used to determine the activity and was normalized to the positive and negative control wells to give a percent activity. The data for each compound concentration (4 wells) was averaged and the percent activity was plotted as a function of compound concentration. The data was analyzed using Table Curve 2D and fitted to a logistical dose-response curve. The majority of compounds achieved a maximal activity at 10 μM. The percent activity at 10 μM was determined for each compound and reported as an average of the three replicate experiments with the corresponding SEM. The individual dose-response curves are not shown.

EGTA Fluorescence Titration Assay—This titration assay is based on a published protocol. Before titration, cuvette was filled with EDTA (10 mM) for 10 min, followed by sterile deionized water and acetone washing for removing any residue metal ions. PAC-1 or derivative (60 μM) was added to a cuvette containing buffer (Hepes: 50 mM, KNO3: 100 mM, pH 7.2) with EGTA (7.3 mM) to achieve a 10-fold dilution (final PAC-1 concentration: 6 μM). Zn(OTf)2 (0-10 mM) was added incrementally. The formation of Zn-PAC-1 (or derivative) complex was monitored by the increase in fluorescence intensity (ex/em: 410 nm/475 nm). Fluorescence intensity at 475 nm was plotted against free Zn concentration ([Zn]f/M) calculated using MaxChelator program. The data was analyzed using KaleidaGraph and fitted to a formation curve based on Eq S1 derived by published protocol.

$$I = (I_{min}K_D + I_{max}[Zn]f)/(K_D + [Zn]f)$$

where Imin and Imax were defined as the fluorescence intensity of the free probe (PAC-1 or derivative in this case) and that of the Zn-probe complex respectively.

Immunofluorescent Staining—Round 18 mm no. 1 borosilicate coverglass (VWR) were coated with poly-lysine by shaking the coverglass in a poly-lysine solution (Sigma) for 1 hour and then washing with MilliQ. SK-MeI-5 human melanoma cells were grown on the poly-lysine coated coverglass in the bottom of a 12 well plate. When Cells achieved ~80% confluency, the cells were treated with either DMSO or 100 μM PAC-1 in DMSO (total DMSO <1%) for 1 hour. The cells were then washed two times with 1 mL of PBS and fixed in 3.7% formaldehyde in PBS for 10-15 minutes at room temperature. The cells were then washed again two times with PBS and then permeabilized with 0.1% Triton X-100 in PBS for 5 minutes. The cells were then blocked in 3% BSA in PBS for 10 minutes and incubated with a 1:500 rabbit anti-procaspase-3 antibody for 1 hour. The coverglass was then washed 5 times with PBS and incubated with a 1:1000 dilution of the secondary anti-rabbit Alexafluor 647 conjugated antibody for 20 minutes protected from light. The coverglass was again washed 5 times with PBS and once with MilliQ H2O. The coverglass were then mounted on glass slides using Fluorosave (Calbiochem) and stored in the dark until imaging. Cells were imaged on a Leica SP2 Multiphoton Confocal microscope.

Live Cell Imaging—SK-MeI-5 cells were grown on the bottom of no. 1 borosilicate growth chambers (Nunc) to a confluency of ~80%. Cells were then treated with DMSO, 25 μM FAM-DEVD-fmk in DMSO, 25 μM AF350-PAC-1 in DMSO, or both 25 μM FAM-DEVD-fmk and 25 μM AF350-PAC-1 concurrently for 1 hour at 37° C. and 5% CO2. Cells were then washed 5 times with RPMI 1640 growth media lacking phenol red. The cells were then allowed to further incubate at 37° C. for 2 hours before imaging. For cells stained with SYBR green for nuclear staining, a 1:100,000 dilution of SYBR green in media was added immediately prior to imaging. Cells were imaged on a Leica SP2 Multiphoton Confocal microscope.

Image Analysis—Images were adjusted in brightness and contrast to allow for clarity. For in the images, the red channel was adjusted using Image J to reflect a linear intensity gradient between 10 and 28. For the green channel, the images were adjusted to a linear intensity gradient between 0 and 44. To account for the offset of the microscope optics, the red channel was manually offset by 5 pixels in the x direction and the green channel was manually offset by 6 pixels in the y direction. The images were filtered with a Gaussian blur with a radius of 1 pixel to improve the signal to noise ratio. Using the Image J plug in, JACoP, the % overlap was determined using the Manders overlap coefficient.

Induction of Apoptosis by PAC-1 derivatives—U937 Cells (1 mL of 1×106 cells/mL) were treated with 5 μL ethanol stocks of the various compounds to achieve a final concentration of 50 μM. The cells were incubated at 37° C. for 12 hours. The cells were centrifuged (200 g for 5 min), washed with PBS (2 mL), resuspended in 500 μL Annexin V Binding Buffer. To each sample was added 10 μL of FITC conjugated Annexin V stain (Southern Biotech) and 10 μL of propidium iodide (Sigma) to a final concentration of 50 μg/mL. Cell populations were analyzed on a Benton Dickinson LSR II cell flow cytometer.

Materials and Methods
General

All reactions requiring anhydrous conditions were conducted under a positive atmosphere of nitrogen or argon in oven-dried glassware. Standard syringe techniques were used for anhydrous addition of liquids. Dry tetrahydrofuran was obtained by passing over activated alumina columns or molecular sieves in a commercial solvent purification system (Innovative Technologies). Unless otherwise noted, all starting materials, solvents, and reagents were acquired from commercial suppliers and used without further purification. Flash chromatography was performed using 230-400 mesh silica gel. Hydrazide 5, PAC-1, 1a, 1 h, 3-allylsalicylaldehyde, 2-mercaptobenzaldehyde, 23, 30, 44 were prepared according to the literature method with modifications.

Compound Analysis

All NMR experiments were recorded either in CDCl3 (Sigma), CD3OD (sigma) or Acetone-d6 (Sigma) on a Varian Unity 400 MHz or 500 MHz spectrometer with residual undeuterated solvent as the internal reference. Chemical shift, δ (ppm); coupling constants, J (Hz); multiplicity (s=singlet, d=doublet, t=triplet, q=quartet, m=multiplet); and integration are reported. High-resolution mass spectral data was recorded on a Micromass Q-T of Ultima hybrid quadrupole/time-of-flight ESI mass spectrometer at the University of Illinois Mass Spectrometry Laboratory. All melting points are uncorrected. Analytical HPLC performed on a Altima C18 column, 2.1×20 mm, mobile phase A is 0.1% TFA in $H_2O$, B is acetonitrile using a gradient system from 0-45% B over 5 min, then 45-55% B from 5-10 min, then 55-100% B over 10-15 min, constant 100% over 15-20 min, and from 100-0% over 20-25. LC-MS performed on a C18 column, 2.1×5 mm, mobile phase A is 0.1% TFA in $H_2O$, B is acetonitrile using a gradient system with constant 0% B over 0-2 min, then 0-50% B from 2-5 min, then 50-100% B over 5-7 min, constant 100% over 7-8 min, and from 100-0% over 8-10.

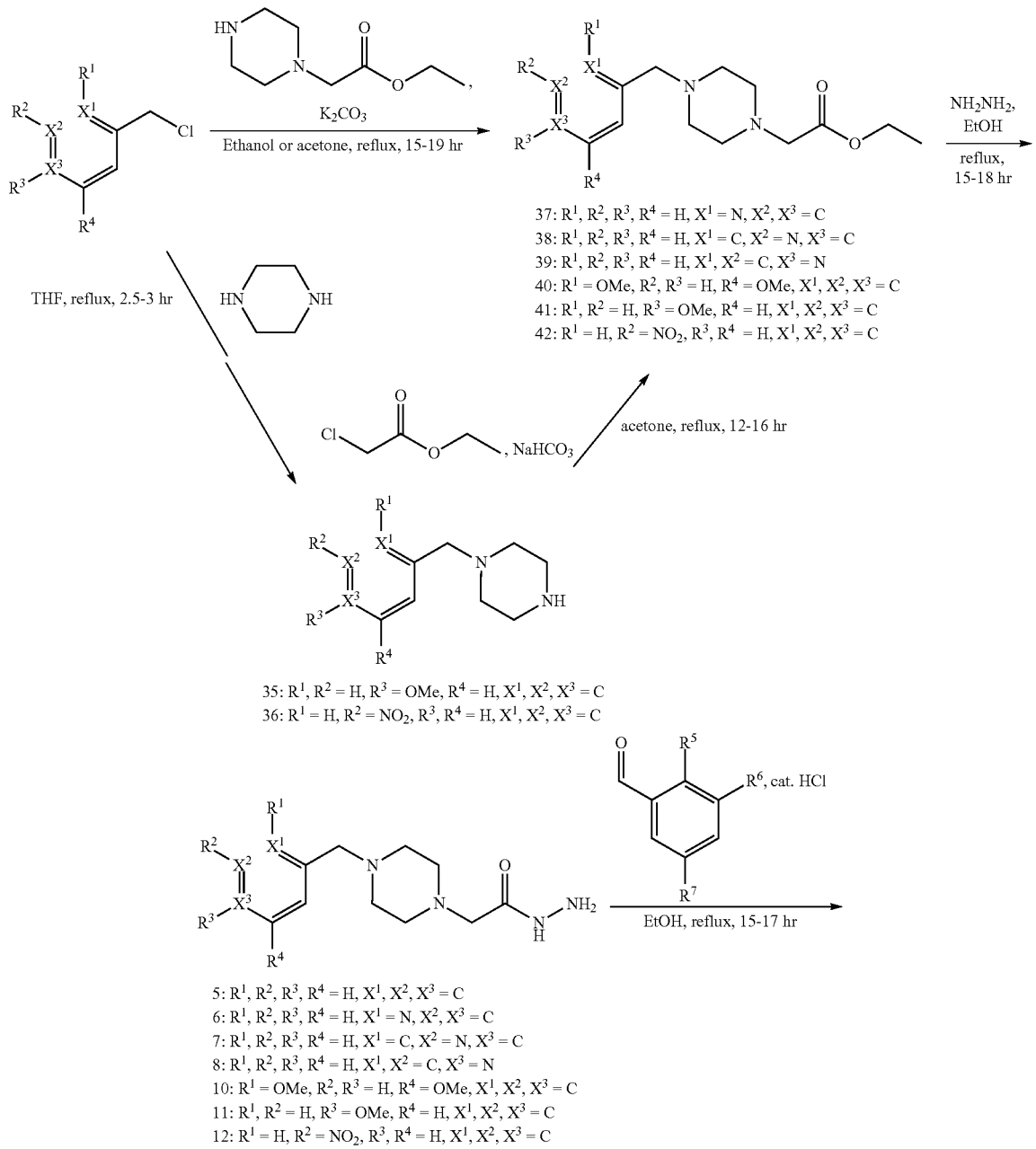

Scheme S1. Syntheses of PAC-1 derivatives

-continued
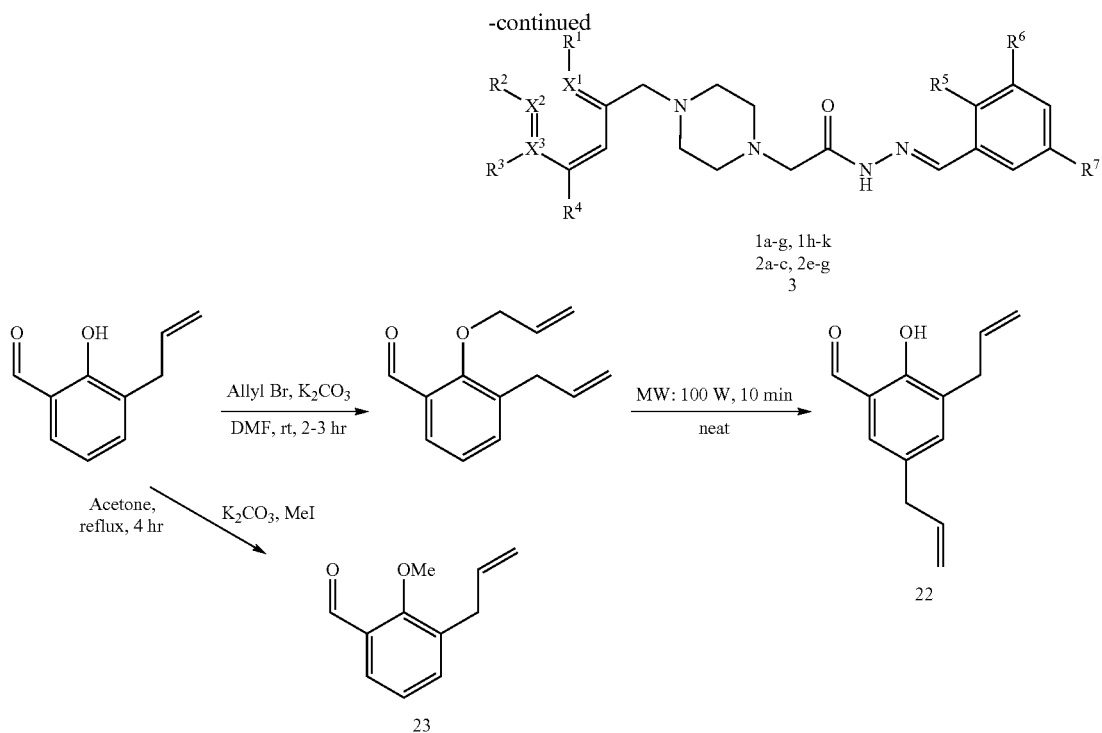
1a-g, 1h-k
2a-c, 2e-g
3
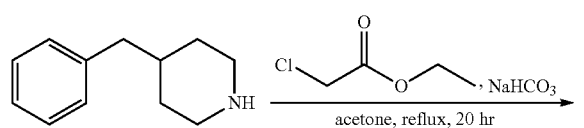
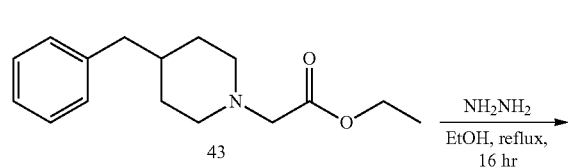
22
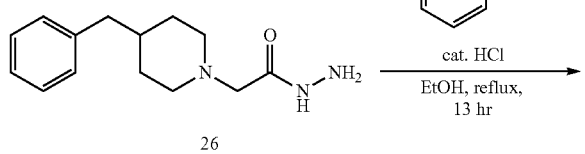
23
Scheme S2. Synthesis of 4c
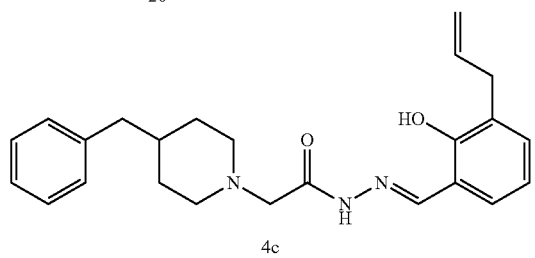
Scheme S3. Syntheses of 4a-b
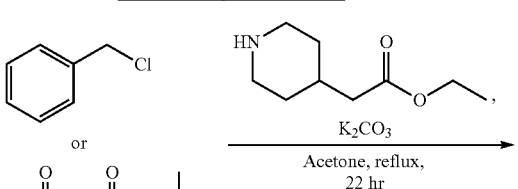
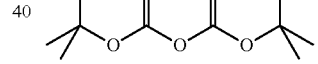
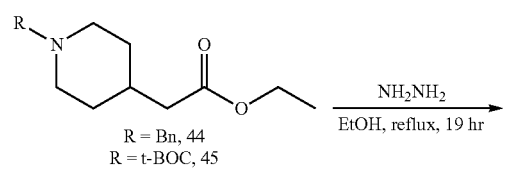
R = Bn, 44
R = t-BOC, 45
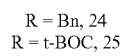
R = Bn, 24
R = t-BOC, 25

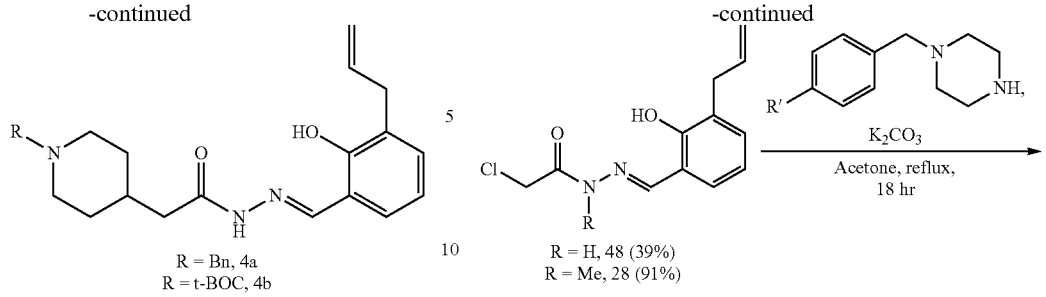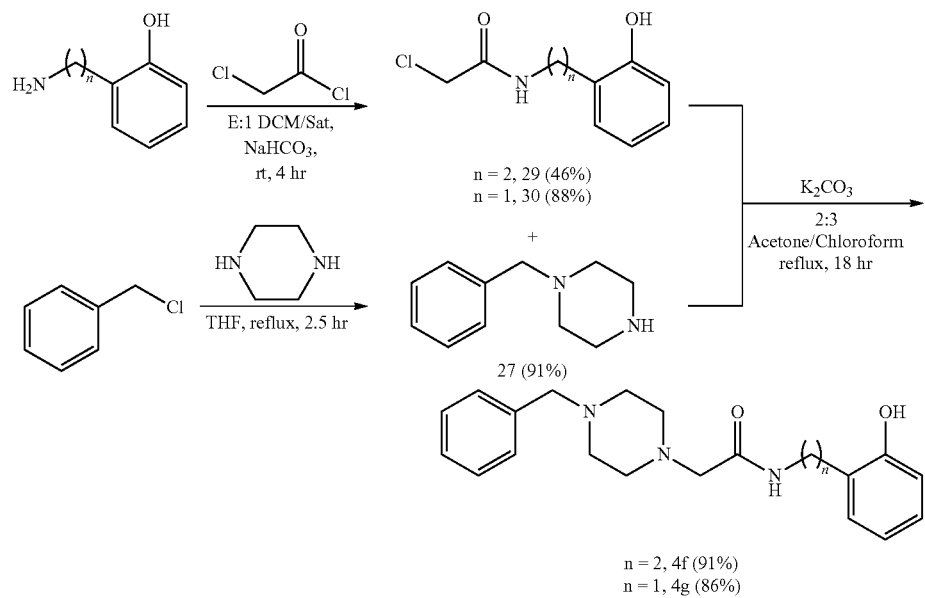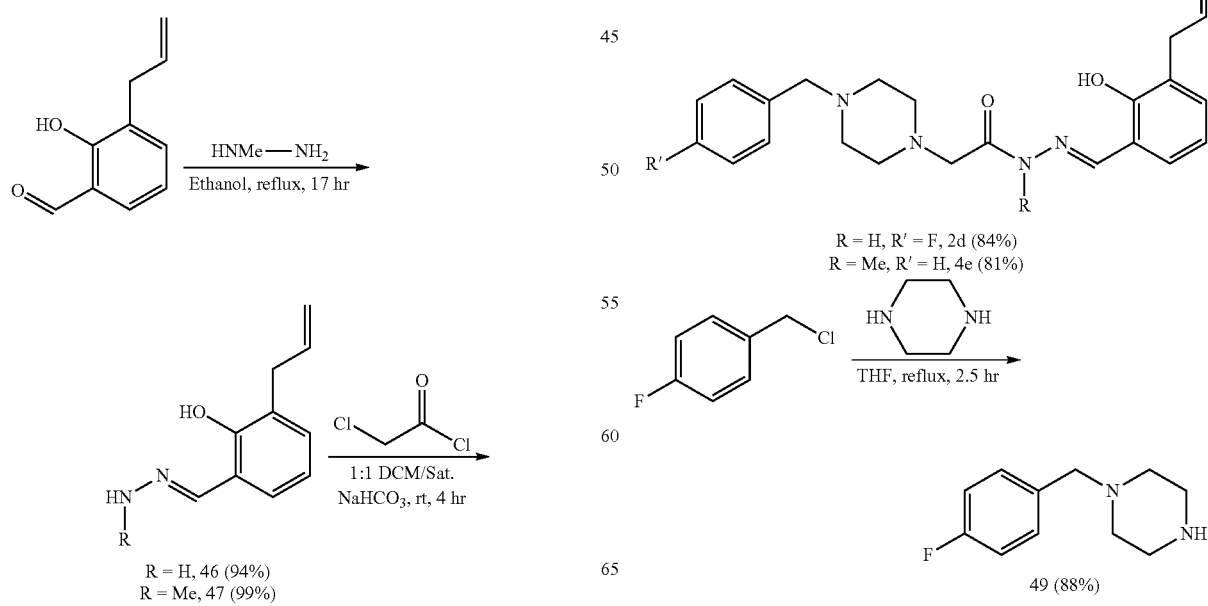

Example 3

Evaluation of PAC-1 Derivatives

Figure 11:
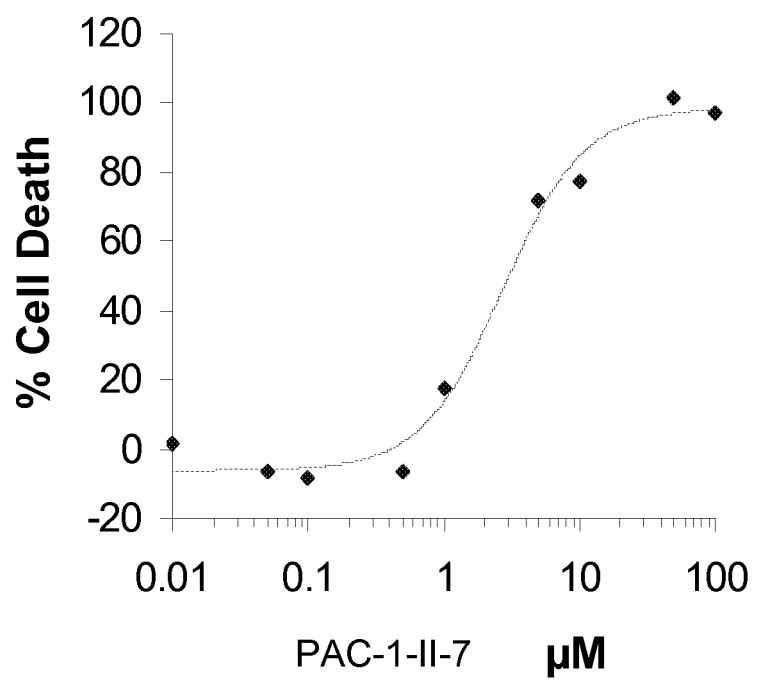
FIG. 11 shows percent cell death by varying concentrations of PAC-I-II-7.
Figure 12:
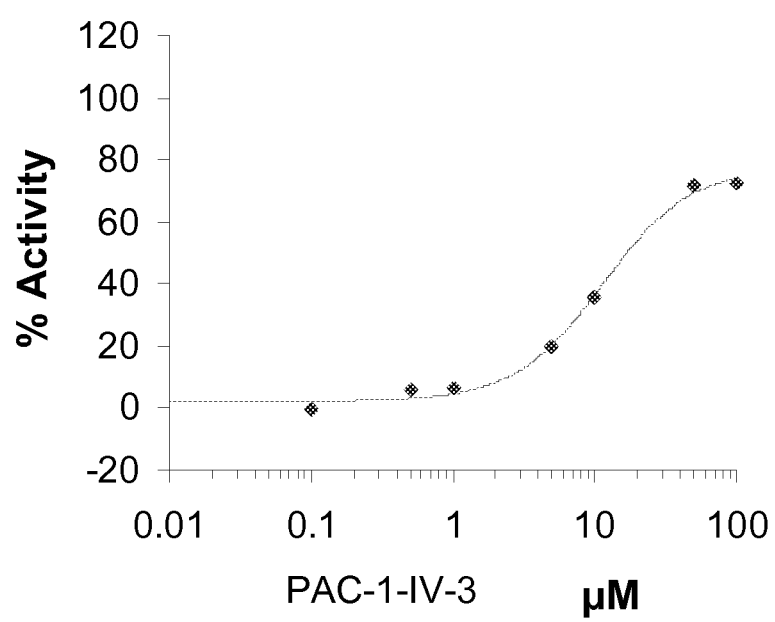
FIG. 12 shows percent cell death by varying concentrations of PAC-I-IV-3.
Figure 13:
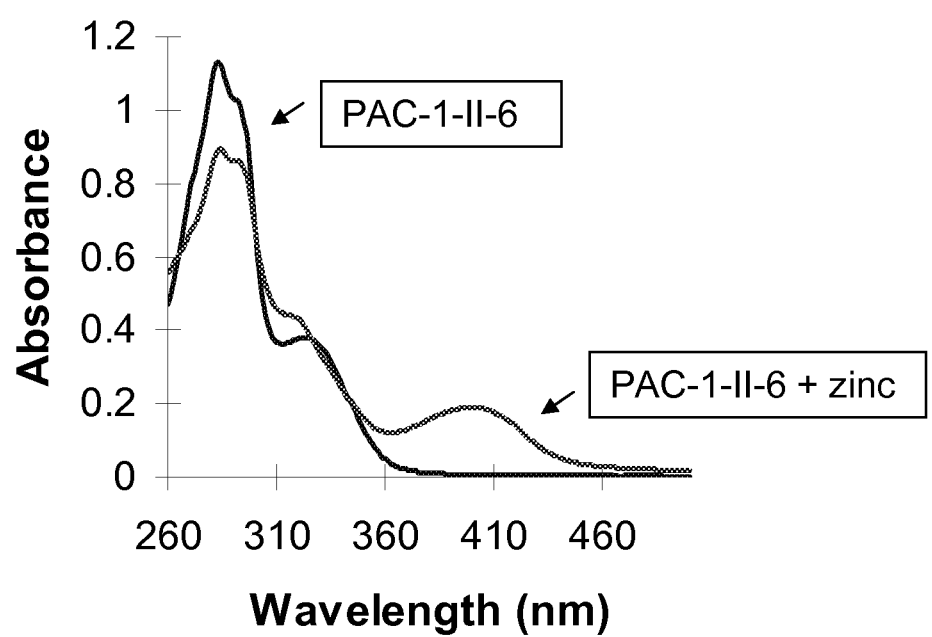
FIG. 13 shows Zinc Binding of PAC-1-II-6.

FIG. 11 shows relief of zinc mediated caspase-3 inhibition for compound 1-II-7. FIG. 12 shows relief of zinc mediated caspase-3 inhibition for compound 1-IV-3. The graphs represents three separate dose response experiments. The error bars represent the standard error of the mean for each data point. FIG. 13 shows the absorbance spectra for compound 1-II-6 with and without zinc.

PAC-1 derivatives were assessed in cell culture and in vitro assays for their ability to kill cancer cells, activate procaspase-3 in vitro, and bind zinc. Compounds that activate procaspase-3 generally have low 1050 values in U937 cells. Exemplary data is shown below in Tables 1-4.

The induction of cell death was determined using the U-937 (human lymphoma) cell line. U-937 cells grow in culture as a suspension. For these experiments, cells were exposed to a range of compound concentrations for 72 h, cell death was quantitated via a sulforhodamine B assay, and $IC_{50}$ values were calculated from logistical dose-response curves.

From the data, it is seen that (1) PAC-1 derivatives that are unable to bind zinc do not activate caspase-3 in vitro, and do not appreciably induce death in U-937 cells in culture. This information suggests that the zinc binding capacity of PAC-1 is important for its cell death-inducing properties. (2) The ortho-hydroxy N-acylhydrazone motif is critical for zinc binding. (3) Virtually all compounds that bind zinc activate caspase-3 in vitro and induce death in U-937 cells in culture. Only compounds I-IV-1 and I-IV-2, which show no in vitro caspase-3 activation but are still cytotoxic to U-937 cells, are exceptions to this trend. Interestingly, we find that these two compounds (at a concentration of 10 μM) are reasonably potent inhibitors of caspase-3 enzymatic activity; thus, any activating effect of the compound may be masked by this inhibition. This inhibition effect is consistent with previous data showing that PAC-1 will also inhibit procaspase-3/caspase-3 at high compound concentrations

TABLE 1

| Class I compounds | | | | |
| --- | --- | --- | --- | --- |
| Compound | Structure | U937 ($IC_{50}$ μM) | Caspase-3 (% Activation at 10 μM) | Zinc Binding ($K_D$) nM |
| PAC-1 | | 4.8 ± 1.0 | 45.8 ± 4.8 | 50 |
| PAC-1-I-1 | | 15.3 ± 2.0 | 30 ± 2 | 79 |
| PAC-1-I-2 | | 61 ± 22 | 0 | ND |
| PAC-1-I-3 | | >100 | 0 | ND |
| PAC-1-I-4 | | >100 | 0 | ND |
| PAC-1-I-5 | | >100 | 0 | ND |

TABLE 1-continued
Class I compounds
| Compound | Structure | U937 (IC$_{50}$ µM) | Caspase-3 (% Activation at 10 µM) | Zinc Binding (K$_D$) nM |
|---|---|---|---|---|
| PAC-1-I-6 | 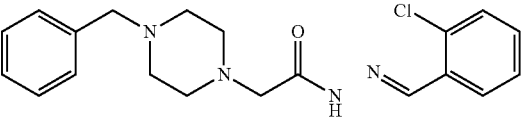 | 57 ± 5 | 0 | ND |
| PAC-1-I-7 | 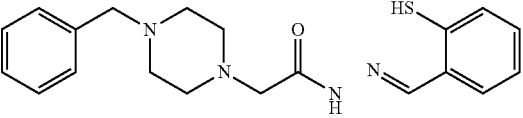 | >100 | 0 | ND |
| PAC-1-I-8 | 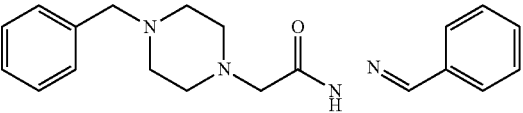 | >100 | 0 | ND |
| PAC-1-I-9 | 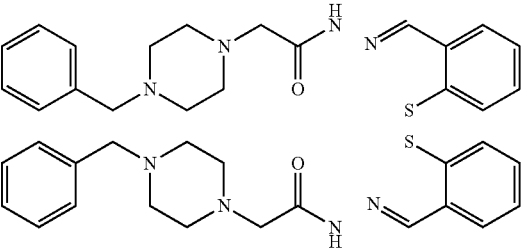 | >100 | 0 | ND |
| PAC-1-I-10 | 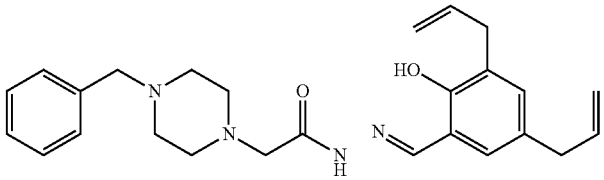 | 1.8 ± 0.4 | 59 ± 5 | 46 |
| PAC-1-I-11 | 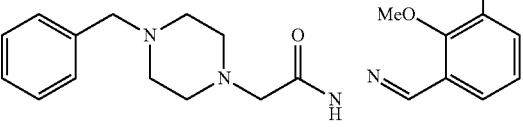 | 32 ± 12 | 0 | ND |
TABLE 2
Class II compounds
| Compound | Structure | U937 (IC$_{50}$ µM) | Caspase-3 (% Activation at 10 µM) | Zinc Binding (K$_D$) nM |
|---|---|---|---|---|
| PAC-1-II-1 | 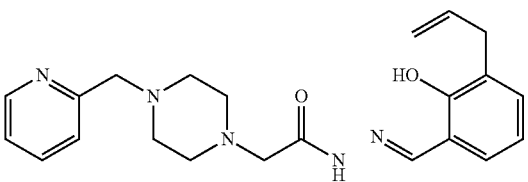 | 9.5 ± 1.8 | 48 ± 3 | 76 |

TABLE 2-continued

Class II compounds

| Compound | Structure | U937 (IC$_{50}$ µM) | Caspase-3 (% Activation at 10 µM) | Zinc Binding (K$_D$) nM |
| --- | --- | --- | --- | --- |
| PAC-1-II-2 | 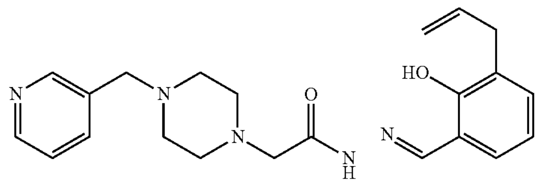 | 14 ± 2 | 20.6 ± 1.6 | 70 |
| PAC-1-II-3 | 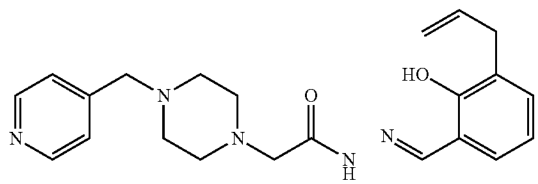 | 21 ± 6 | 26.3 ± 0.1 | 50 |
| PAC-1-II-4 | 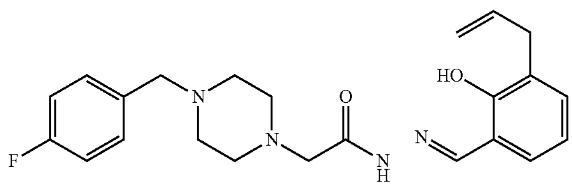 | 2.0 ± 0.2 | 24.2 ± 1.7 | 96 |
| PAC-1-II-5 | 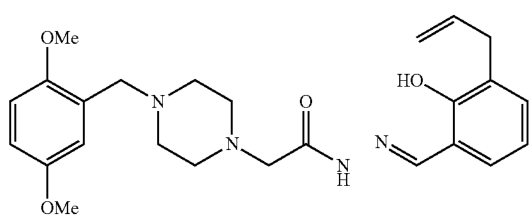 | 1.0 ± 0.1 | 31 ± 3.6 | 36 |
| PAC-1-II-6 | 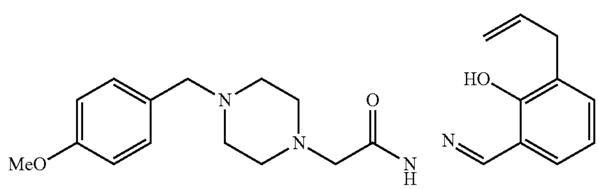 | 2.7 ± 0.8 | 24 ± 3.4 | 41 |

TABLE 3

Class III compounds

| Compound | Structure | U937 (IC$_{50}$ µM) | Caspase-3 (% Activation at 10 µM) | Zinc Binding (K$_D$) nM |
| --- | --- | --- | --- | --- |
| PAC-1-III-1 | 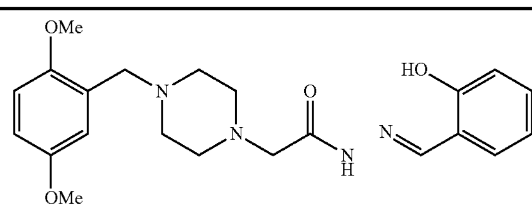 | 12 ± 2 | 30.7 ± 1.2 | 68 |

TABLE 4
| | Class IV compounds | | | | |
|---|---|---|---|---|---|
| Compound | Structure | | U937 (IC$_{50}$ µM) | Caspase-3 (% Activation at 10 µM) | Zinc Binding (K$_D$) nM |
| PAC-1-IV-1 | 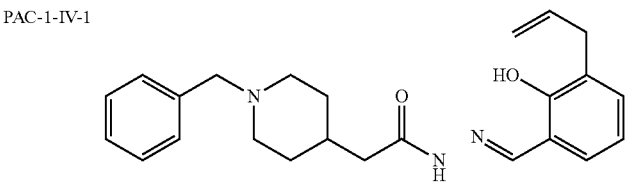 | | 2.8 ± 1.1 | 0 | ND |
| PAC-1-IV-2 | 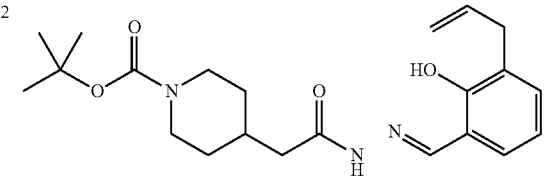 | | 6.5 ± 3.6 | 0 | ND |
| PAC-1-IV-3 | 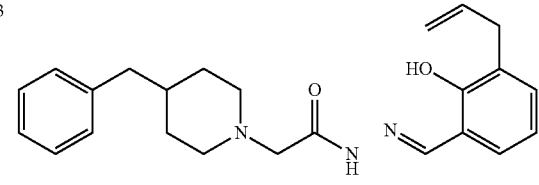 | | 2.7 ± 1.1 | 36 ± 3* | 50 |
| PAC-1-IV-4 | 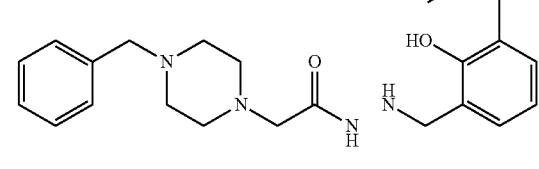 | | 59 ± 14 | 17.1 ± 1.2 | ND |
| PAC-1-IV-5 | 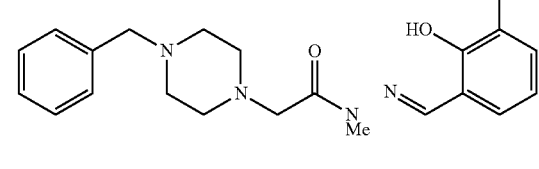 | | 22 ± 3 | 0 | ND |
| PAC-1-IV-6 | 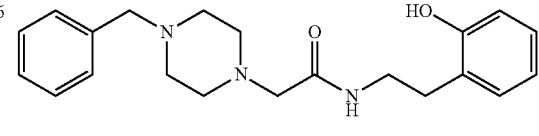 | | >100 | 4.1 ± 1.0 | ND |
| PAC-1-IV-7 | 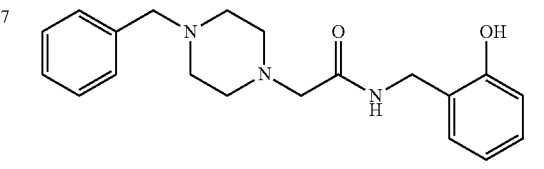 | | >100 | 4.4 ± 0.9 | ND |

Example 4

Confocal Microscopy

Confocal microscopy was performed with fluorescent PAC-1 to investigate the sub-cellular localization of PAC-1 in cells, so as to confirm that PAC-1 kills cancer cells by binding to Zn2+. The fluorescent version of PAC-1 was synthesized by "clicking" Alexa Fluor 350 to PAC-1 as shown in Scheme 5.

background levels of staining in both the red and green channels (shaded gray here). Cells treated only with FAM-DEVD-fmk do not show any staining above background levels. Cells treated only with AF-PAC-1 show punctate staining in the cytoplasm with no increase in the emission at 520 nm. Cells treated concurrently with AF-PAC-1 and FAM-DEVD-fmk show spots of intense caspase-3/-7 activity (pseudocolored) and punctate staining of AF-PAC-1 (pseudocolored), which exhibit good colocalization in the merged image.

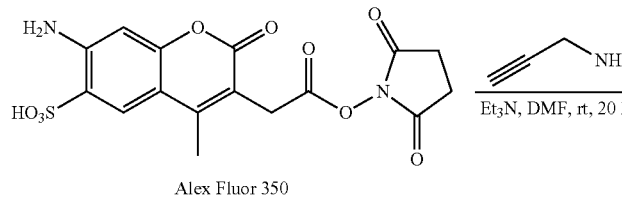

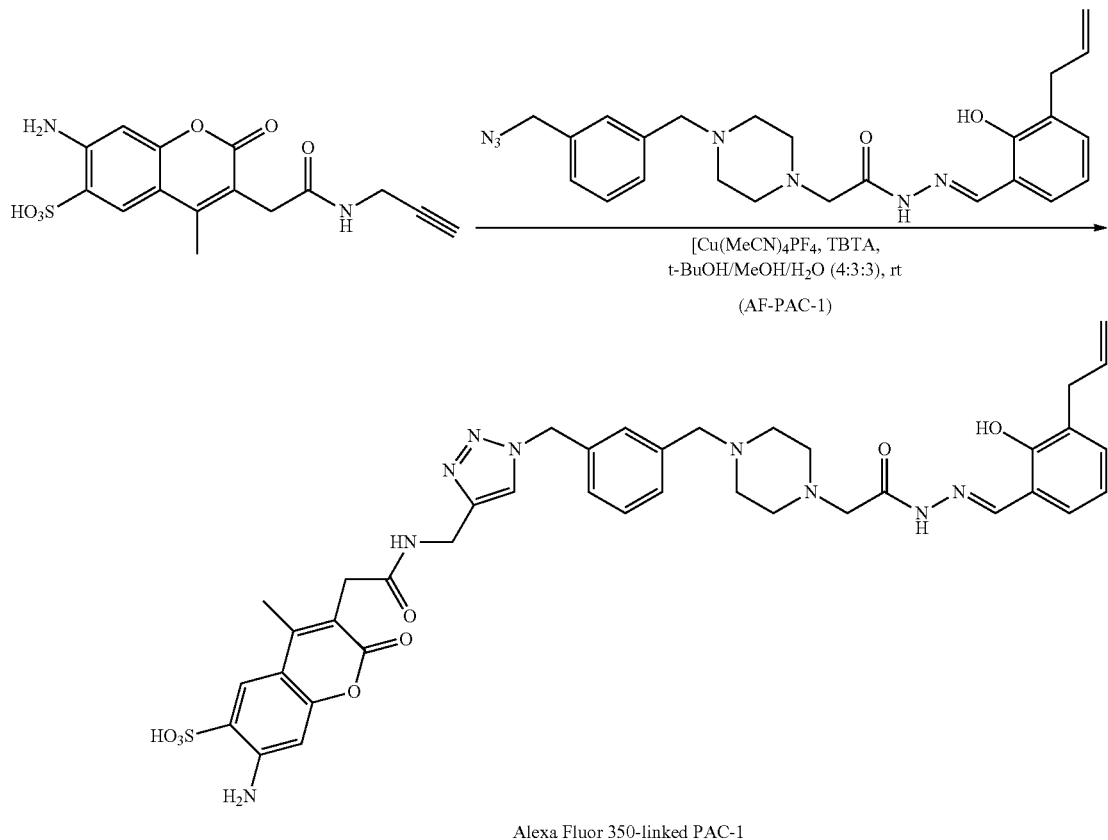

Figure 14:
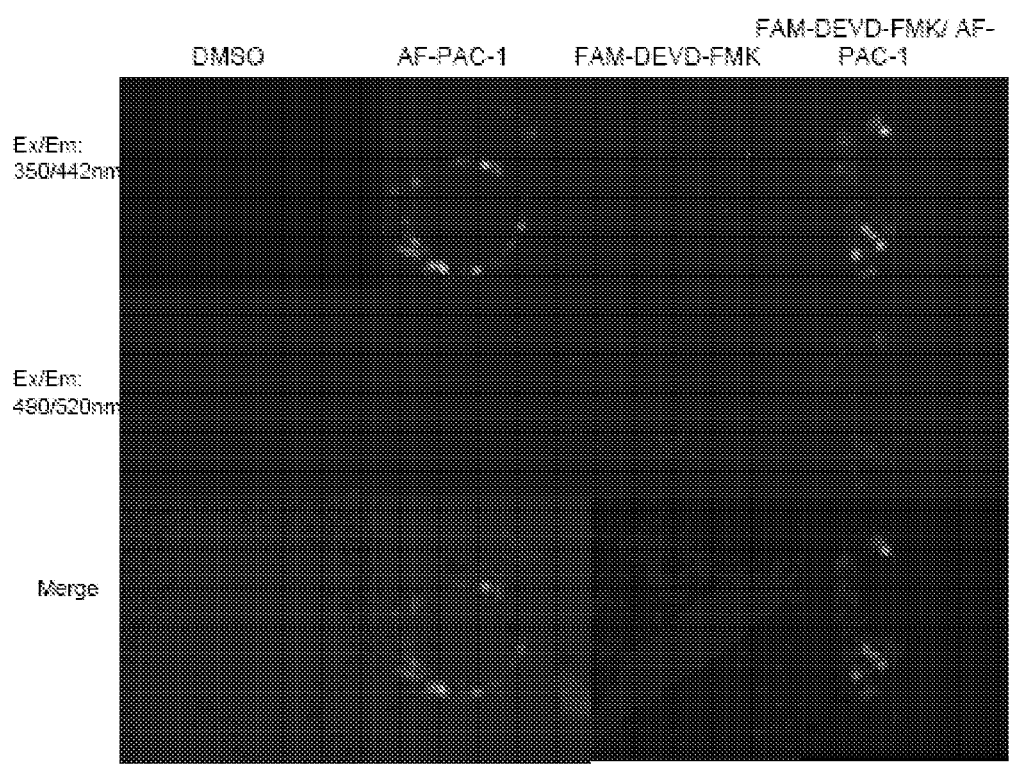
FIG. 14 shows results of a confocal microscopy study.

The fluorescently labeled compound AF-PAC-1 shown above has activity similar to that of PAC-1 in these assays (IC$_{50}$ versus U-937 cells=14.8 (3.2 µM; caspase-3 activation at 10 µM=6.3 (1.6% and at 50 µM=20 (3%; K$_d$ for zinc=61(9 nM). FIG. 14 shows results of the confocal microscopy study. Colocalization of AF-PAC-1 with sites of caspase-3/-7 enzymatic activity. SK-MEL-5 cells treated with DMSO show

Example 5

Clinical Trials with Dogs for PAC-1

Formulation of PAC-1 with 2-hydroxypropyl-β-cyclodextrin was administered into animals at higher doses. Dog experienced acute neurological toxicity (ataxia and seizure). Further studies in mice showed similar symptoms at high doses. It is believed that PAC-1 crosses the blood-brain barrier (BBB) and chelates the inhibitory zinc bound at the NMDA receptors. As a result, a new compound, PAC-II-9 was synthesized and tested. Further information about this compound is described elsewhere herein.

TABLE 5

Prediction of Blood-Brain Barrier (BBB) permeability

| Compound | Structure | U937 (IC50 μM) | LogBB | BB ([brain]/[blood]) |
|---|---|---|---|---|
| PAC-1 | 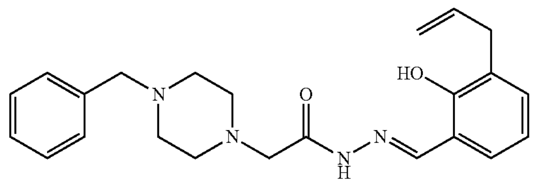 [SMILES: C=CCc1cccc(/C=N/NC(=O)CN2CCN(Cc3ccccc3)CC2)c1O] | 4.8 ± 1.0 | −0.07 | 0.85/1 |
| PAC-1-II-9 | 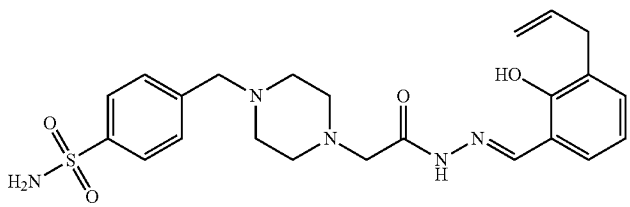 [SMILES: C=CCc1cccc(/C=N/NC(=O)CN2CCN(Cc3ccc(S(N)(=O)=O)cc3)CC2)c1O] | 3.9 ± 1.4 | −1.26 | 0.05/1 |

Preliminary Results
Mice

| PAC-1 (mg/kg) | Neurotoxicity | PAC-1-II-9 (mg/kg) | Neurotoxicity |
|---|---|---|---|
| 12.5 | No | 12.5 | No |
| 25.0 | Yes | 25.0 | No |
| 37.5 | Yes | 37.5 | No |

Dogs

| PAC-1 (mg/kg) | Neurotoxioity | PAC-1-II-9 (mg/kg) | Neurotoxicity |
|---|---|---|---|
| 25.0 | yes | 60.0 | No | logBB = −0.0148 × (PSA) + 0.152 × (ClogP) + 0.139 www.daylight.com     ChemDraw

Preliminary animal studies showed that PAC-1-II-9 was useful to improve the neurotoxicity issue.

Additional compounds and Log BB data are provided in Table 6.

TABLE 6

| Compound | Structure | U937 (IC50 μM) | Caspase-3 (% Activation at 10 μM) | Zinc Binding ($K_D$) nM | LogBB | Solubility in β-Cyclodextran (mg β-CD/μmol Compound) |
|---|---|---|---|---|---|---|
| PAC-1 | 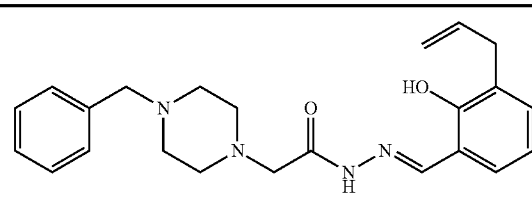 | 4.8 ± 1.0 | 45.8 ± 4.8 | 50 | −0.07 | 5.3 |

TABLE 6-continued

| Compound | Structure | U937 (IC50 μM) | Caspase-3 (% Activation at 10 μM) | Zinc Binding ($K_D$) nM | LogBB | Solubility in β-Cyclodextran (mg β-CD/μmol Compound) |
|---|---|---|---|---|---|---|
| PAC-1-I-1 | 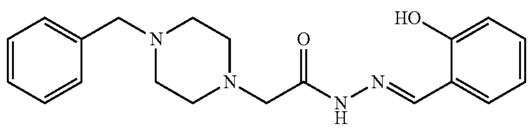 [SMILES: O=C(CN1CCN(Cc2ccccc2)CC1)N/N=C/c1ccccc1O] | 15.3 ± 2.0 | 90 ± 2 | 79 | −0.23 | |
| PAC-1-III-1 | 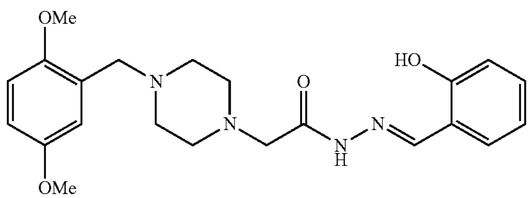 [SMILES: COc1ccc(OC)c(CN2CCN(CC(=O)N/N=C/c3ccccc3O)CC2)c1] | 12 ± 2 | 30.7 ± 1.2 | 68 | −0.52 | |
| PAC-1-I-10 | 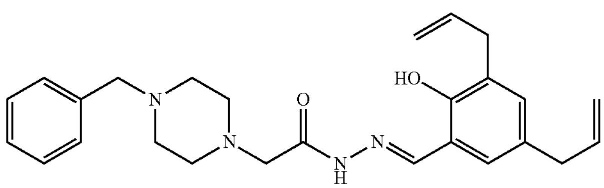 [SMILES: C=CCc1cc(/C=N/NC(=O)CN2CCN(Cc3ccccc3)CC2)c(O)c(CC=C)c1] | 1.8 ± 0.4 | 59 ± 5 | 46 | 0.08 | |
| PAC-1-II-1 | 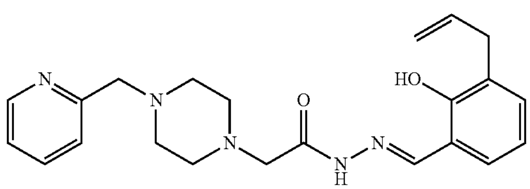 [SMILES: C=CCc1cccc(/C=N/NC(=O)CN2CCN(Cc3ccccn3)CC2)c1O] | 9.5 ± 1.8 | 48 ± 3 | 76 | −0.50 | |
| PAC-1-II-4 | 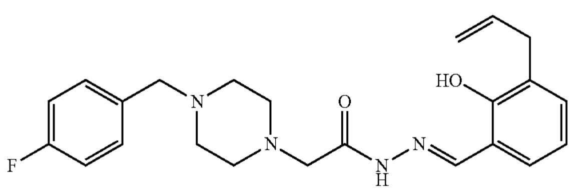 [SMILES: C=CCc1cccc(/C=N/NC(=O)CN2CCN(Cc3ccc(F)cc3)CC2)c1O] | 2.0 ± 0.2 | 24.2 ± 1.7 | 96 | −0.06 | |
| PAC-1-II-5 | 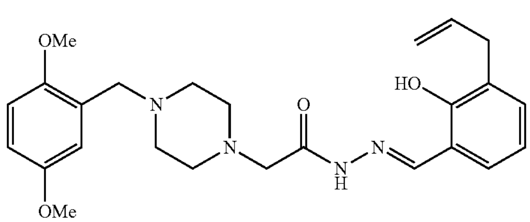 [SMILES: C=CCc1cccc(/C=N/NC(=O)CN2CCN(Cc3cc(OC)ccc3OC)CC2)c1O] | 1.0 ± 0.1 | 31 ± 3.6 | 96 | −0.36 | 15.2 |
| PAC-1-II-6 | 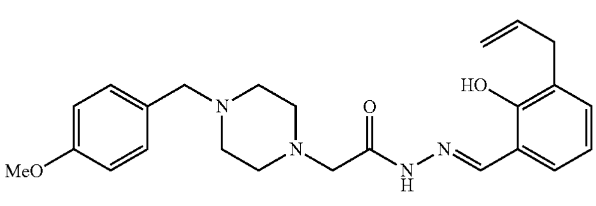 [SMILES: C=CCc1cccc(/C=N/NC(=O)CN2CCN(Cc3ccc(OC)cc3)CC2)c1O] | 2.7 ± 0.8 | 24 ± 3.4 | 41 | −0.24 | 7.1 |

TABLE 6-continued

| Compound | Structure | U937 (IC50 μM) | Caspase-3 (% Activation at 10 μM) | Zinc Binding ($K_D$) nM | LogBB | Solubility in β-Cyclodextran (mg β-CD/μmol Compound) |
|---|---|---|---|---|---|---|
| PAC-1-IV-3 | 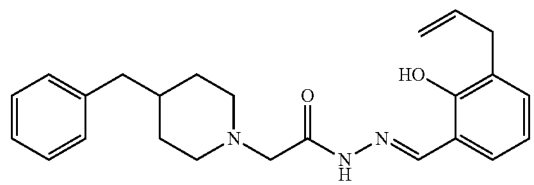 [SMILES: C=CCc1cccc(/C=N/NC(=O)CN2CCC(Cc3ccccc3)CC2)c1O] | 2.7 ± 1.1 | 36 ± 3* | 50 | 0.1 | |
| PAC-1-III-2 | 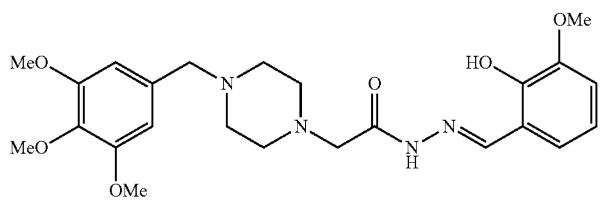 [SMILES: COc1cccc(/C=N/NC(=O)CN2CCN(Cc3cc(OC)c(OC)c(OC)c3)CC2)c1O] | 27 ± 9.4 | | | −0.9 | |
| PAC-1-III-3 | 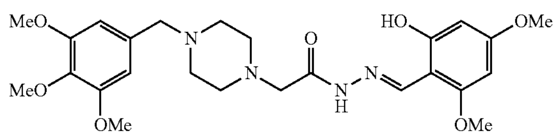 [SMILES: COc1cc(O)c(/C=N/NC(=O)CN2CCN(Cc3cc(OC)c(OC)c(OC)c3)CC2)c(OC)c1] | 38 ± 6.2 | | | −1.1 | |
| PAC-1-III-4 | 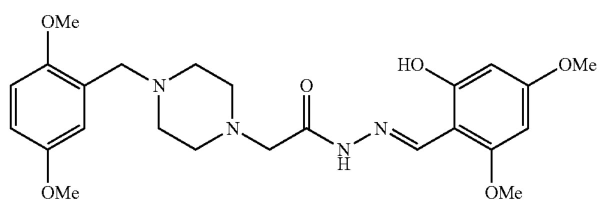 [SMILES: COc1ccc(OC)c(CN2CCN(CC(=O)N/N=C/c3c(O)cc(OC)cc3OC)CC2)c1] | 17.5 | | | −0.0 | |
| PAC-1-III-5 | 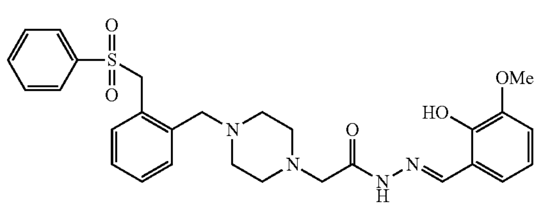 [SMILES: COc1cccc(/C=N/NC(=O)CN2CCN(Cc3ccccc3CS(=O)(=O)c3ccccc3)CC2)c1O] | 8.4 ± 1.8 | | | −0.9 | |
| PAC-1-III-6 | 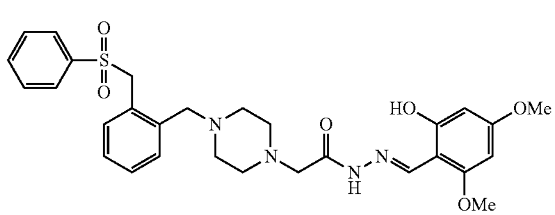 [SMILES: COc1cc(O)c(/C=N/NC(=O)CN2CCN(Cc3ccccc3CS(=O)(=O)c3ccccc3)CC2)c(OC)c1] | 5.5 ± 1.5 | | | −1.1 | |
| PAC-1-II-7 | 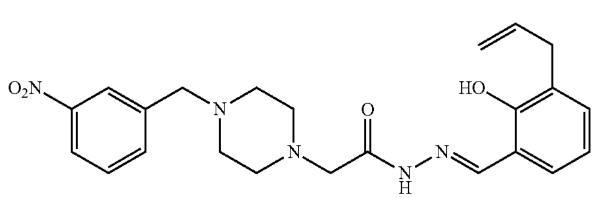 [SMILES: C=CCc1cccc(/C=N/NC(=O)CN2CCN(Cc3cccc([N+](=O)[O-])c3)CC2)c1O] | 4.6 ± 1.0 | | | −0.8 | 4.0 |

TABLE 6-continued

| Compound | Structure | U937 (IC50 μM) | Caspase-3 (% Activation at 10 μM) | Zinc Binding ($K_D$) nM | LogBB | Solubility in β-Cyclodextran (mg β-CD/μmol Compound) |
|---|---|---|---|---|---|---|
| PAC-1-II-8 | 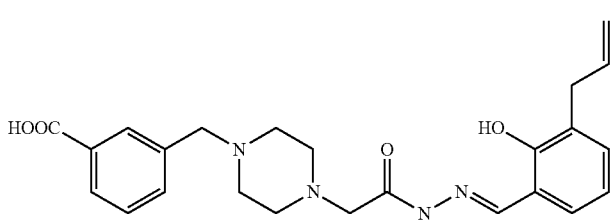 | 2.3 | | | −1.02 | 5.6 |
| PAC-1-II-9 | 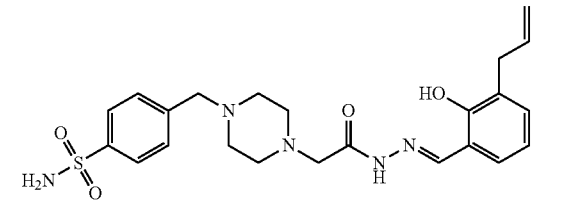 [SMILES: C=CCc1cccc(/C=N/NC(=O)CN2CCN(Cc3ccc(S(N)(=O)=O)cc3)CC2)c1O] | 3.6 | | | −1.26 | 3.5 |
| | 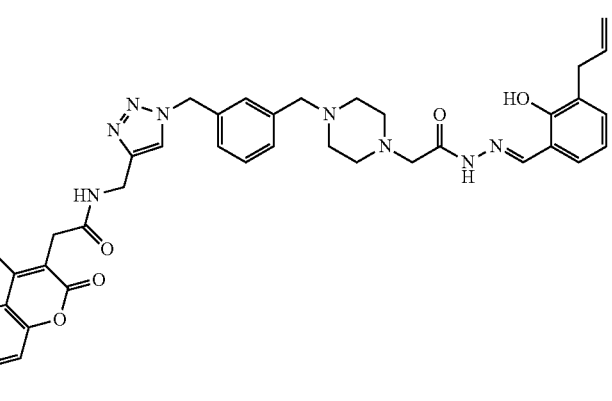 | 10.7 | | | | |

Example 6

PAC-II-9 (S-PAC-1) Reduces Neurotoxicity

Induction of apoptotic cell death is a promising anticancer strategy. A critical event in the cascade of apoptosis is the proteolytic activation of procaspase zymogens to the active caspases, cysteine proteases which then cleave scores of cellular substrates. In 2006, a small molecule that enhances the catalytic activity of procaspase-3 and induces its autoactivation to caspase-3 was reported. This compound, called PAC-1, induces apoptosis in cancer cells, and exhibits antitumor activity in murine xenograft models when administered orally as a lipid-based formulation or implanted subcutaneously as a cholesterol pellet. Herein the assessment of PAC-1 (delivered as an intravenous bolus) in mice is reported, and these studies reveal high dosages of PAC-1 induce neurotoxicity. Based on this finding and the putative mechanism of neurotoxicity, a PAC-1 derivative, called S-PAC-1, was designed, synthesized, and evaluated. Similar to PAC-1, S-PAC-1 activates procaspase-3 and induces apoptotic death in cancer cells; however, it induces no neurotoxicity, as evaluated in mice and dogs. A continuous intravenous infusion protocol was established for S-PAC-1 in dogs, allowing this compound to reach a steady state plasma concentration of ~15 μM for 24 hours. Five pet dogs with lymphoma were evaluated in a small clinical trial with S-PAC-1. Results show that S-PAC-1 is well-tolerated in these patients, and these treatments induced partial regression or stable disease in 4 of 5 patients.

In the last decade, the potential of targeted therapeutics as personalized anticancer strategies has been demonstrated. These approaches exploit specific proteins present in cancer cells to confer specificity versus normal cells (1). Such "personalized" drugs hit targets (2) that arise from a chromosomal translocation (Gleevec for the BCR-ABL fusion protein (3)), specific mutant forms of a protein resulting in constitutive activation (Iressa and EGFR mutation, (4) PLX4032 and mutant BRAF (5,6)), or a protein that is overexpressed in cancer cells (described further below). As one of the hallmarks of cancer is resistance to apoptosis (7-9), apoptotic proteins are particularly interesting targets for anticancer drug discovery (10). Indeed, anticancer activity has been demonstrated with compounds that target the dysregulated expression of apoptotic proteins, including small molecule disruptors of the p53-MDM2 interaction (11,12), inhibitors of Bcl-2 (13), and ligands for XIAP (14, 15).

Members of the caspase family of cysteine proteases are key players in both the initiation and execution of apoptosis. These enzymes exist in the cell as low activity zymogens (proenzymes) that are proteolytically activated to the mature, highly active enzyme. Most critical to apoptosis is the proteolytic conversion of procaspase-3 to the caspase-3. As both the intrinsic and extrinsic apoptotic pathways converge to activate procaspase-3, and as caspase-3 has over 100 cellular substrates, the activation of procaspase-3 to caspase-3 is a pivotal and committed event in the apoptotic cascade. Interestingly, procaspase-3 is overexpressed in a variety of tumor histologies including breast cancer (16), colon cancer (17), lung cancer (18), lymphoma (19), neuroblastoma (20), melanoma (21) and liver cancer (22), suggesting that a small molecule that activates procaspase-3 could have selectivity for cancer cells versus normal cells. In 2006 we reported the discovery of a small molecule, called PAC-1, which enhances procaspase-3 activity in vitro, induces death in cancer cells in culture, and has efficacy in multiple mouse xenograft models when administered orally as a lipid-base formulation or implanted subcutaneously as a cholesterol pellet (23). PAC-1 activates procaspase-3 in vitro through the chelation of inhibitory zinc ions (24), and derivative synthesis and evaluation revealed that the biological activity of PAC-1 is tied to having an intact ortho-hydroxy N-acyl hydrazone zinc-chelating motif (25). Much data suggests that PAC-1 induces apoptotic death in cancer cells through the chelation of zinc from procaspase-3, most notably the colocalization of a fluorescent PAC-1 derivative with sites of cellular caspase-3 activity (25).

As the first procaspase-activating compound, experiments with PAC-1 show the potential of procaspase-3 activation as a viable anticancer strategy. To further develop PAC-1 as an experimental therapeutic for the treatment of cancer in people, we sought to characterize the effect of this compound when administered intravenously and in more sophisticated in vivo tumor model systems, specifically, canines with spontaneous cancer. The evaluation of experimental therapeutics in pet dogs with cancer offers many advantages over murine xenograft models (26). Herein we report toxicity studies of intravenous PAC-1 in mice, and the discovery of a PAC-1 derivative (called S-PAC-1) that induces apoptosis in cancer cell lines in culture, is well-tolerated in mice and research dogs, and has efficacy in a small trial of canine patients with spontaneous lymphoma.

Formulation of PAC-1. To expedite the translational investigation of procaspase-3 activators for treating human cancer patients, the tolerability of PAC-1 when administered intravenously (the most common drug delivery route for conventional anticancer agents) was assessed. To this end we first optimized a formulation procedure which reliably maintained high concentrations of PAC-1, a lipophilic drug, in aqueous solution. The solubilizing agent allowing for the dissolution and maintenance of PAC-1 in aqueous solution was 2-hydroxypropyl-β-cyclodextrin. In an aqueous 200 mg/mL solution of 2-hydroxypropyl-β-cyclodextrin, PAC-1 is soluble at 20 mg/mL. Complete dissolution requires acidification of the aqueous solution to pH 1.5-2, and then the solution is restored to pH 5-6. Using this procedure PAC-1 will remain in solution and is stable for at least 5 days when stored at 4° C.

Toxicity of PAC-1. In an effort to characterize the feasibility and tolerability of intravenously administered PAC-1, C57/BL6 mice were administered PAC-1 (dissolved in 2-hydroxypropyl-β-cyclodextrin) at 10, 20, 30 and 50 mg/kg via lateral tail vein injection, and the animals were observed for 24 hours. At 10 mg/kg of PAC-1, no clinical signs of toxicity were observed. Mice that received 20 mg/kg of PAC-1 in this manner exhibited mild neurological symptoms including lethargy, and mild ataxia; these symptoms persisted for 20 minutes after injection, at which point the mice recovered and showed no further signs of toxicity. Mice that received 30 mg/kg of PAC-1 exhibited overt signs of neurotoxicity including spasms (1/3), ataxia (3/3) and loss of balance (3/3) with onset occurring within 5 minutes of injection and lasting approximately 15 minutes. Mice that received 50 mg/kg of PAC-1 exhibited acute neurotoxic symptoms with more pronounced ataxia and loss of balance. At this dosage muscle spasms were observed in all mice. Mice that received only the 2-hydroxypropyl-β-cyclodextrin vehicle did not exhibit toxicity. Despite this observed neurotoxicity in mice, PAC-1 has been administered safely to dogs at lower doses. To confirm that this neurotoxicity was not species specific, 60 mg/kg of PAC-1 was administered i.v. to one healthy research hound dog over the course of 10 minutes. Administration of this high concentration of PAC-1 resulted in similar neurotoxicity including ataxia and spasms which lasted for 20 minutes.

Given the known affinity of PAC-1 for zinc in vitro (24), and its demonstrated ability to bind to cellular zinc (25), we hypothesized that the neurotoxicity observed in mice and dogs that were administered PAC-1 in 2-hydroxypropyl-β-cyclodextrin was caused by the chelation of intracellular zinc at NMDA receptors within the central nervous system of the treated mice. This hypothesis is consistent with data from in vivo studies of other zinc chelators that induce a neurological phenotype reminiscent of what we observed with PAC-1. (27,28) Indeed, in silico analysis of PAC-1 to predict the partitioning across the blood-brain barrier (BBB)29 shows that PAC-1 has a calculated log BB of −0.07. This log BB would correlate to a partitioning ratio of 0.85/1.0 between the blood and the brain, suggesting that a significant amount of PAC-1 may be entering the central nervous system. Several studies have indicated that chelation of intracellular zinc stores relieves tonic suppression of NMDA receptors, resulting in neuronal hyperexcitation (28,30).

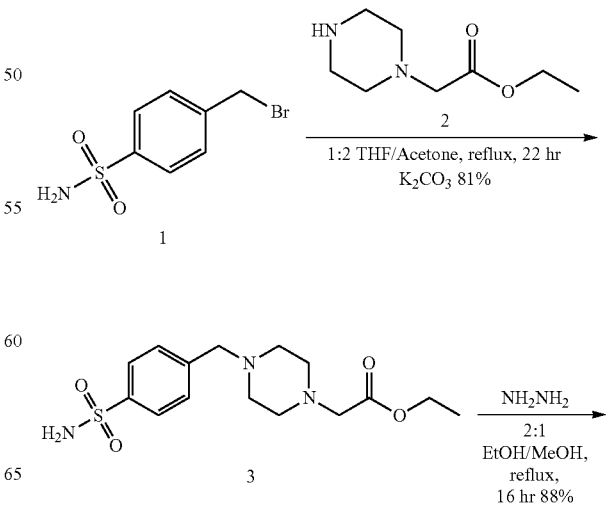

Scheme 1

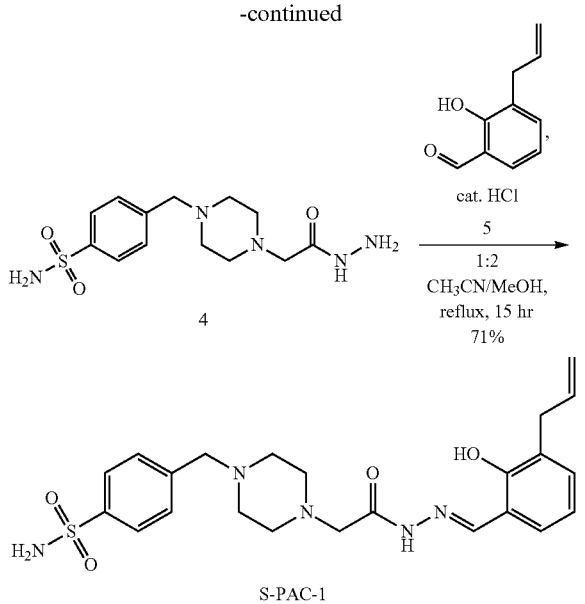

Grain-Scale synthesis of S-PAC-1.

Design of S-PAC-1. To overcome this neurotoxicity, we synthesized a derivative of PAC-1 that had a lower propensity to cross the BBB to exhibit decreased neurotoxicity and allow for dosing at higher concentrations. A polar functional group installed on the benzyl ring of PAC-1 should decrease the predicted log BB while maintaining the activity of the parent compound. As such S-PAC-1, a sulfonamide derivative of PAC-1, was designed as a compound predicted to have a markedly decreased ability to cross the BBB (log BB of −1.26). The synthetic route to S-PAC-1 is shown in Scheme 6; this route is a modification of the synthetic route to PAC-1 previously reported (23). Briefly, sulfonamide 1 is coupled with piperazine 2 to provide ester 3 in good yield. The ester is then reacted with hydrazine to produce hydrazide 4, which is then condensed with aldehyde 5 to furnish S-PAC-1. All experimental details for this route and spectral data for S-PAC-1 and the various intermediates can be found elsewhere herein. Notably, the reaction sequence is highly scalable; indeed, the yields listed in Scheme 6 are for production of 40 grams of S-PAC-1. Critical to this scale-up was the development of facile purification protocols for each intermediate. Thus, compound 2 is purified via recrystallization from ethanol, hydrazide 3 is purified through recrystallization from methanol, and the final product is purified through silica gel chromatography and recrystallization from methanol. By conducting this synthesis four times on a 40 gram scale, over 160 g of S-PAC-1 was successfully produced. Details of smaller scale synthesis of S-PAC-1 may be found elsewhere herein.

Figure 16:
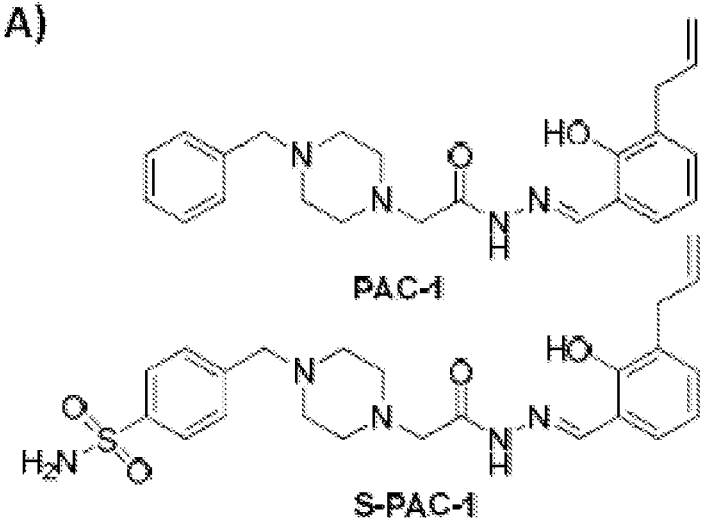
FIG. 16 shows in vitro characterization of S-PAC-1. A) Structures of PAC-1 and S-PAC-1. B) The formation curve of the $Zn^{2+}$:S-PAC-1 complex. S-PAC-1 binds zinc with a Kd of 46±5 nM. C) S-PAC-1 activates procaspase-3 D3A in vitro. A 10 µM concentration of uncleavable procaspase-3 (D3A) was incubated in the presence of 15 µM exogenous zinc. Addition of 50 µM S-PAC-1 results in a rapid increase in activity during the first five minutes followed by a slow increase over the subsequent 60 minutes. D) S-PAC-1 induces apoptosis in U-937 cells. U-937 cells were incubated with 50 µM S-PAC-1 for 12 hours and analyzed by annexin V/PI staining.
Figure 16:
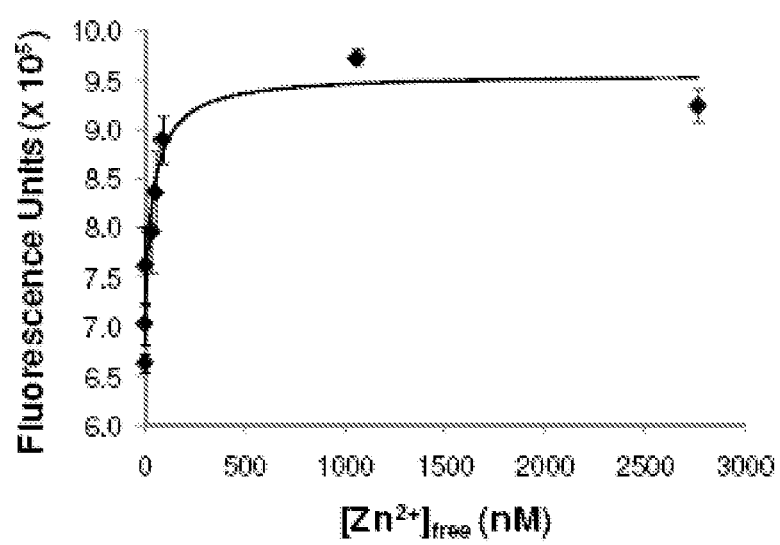
Figure 16:
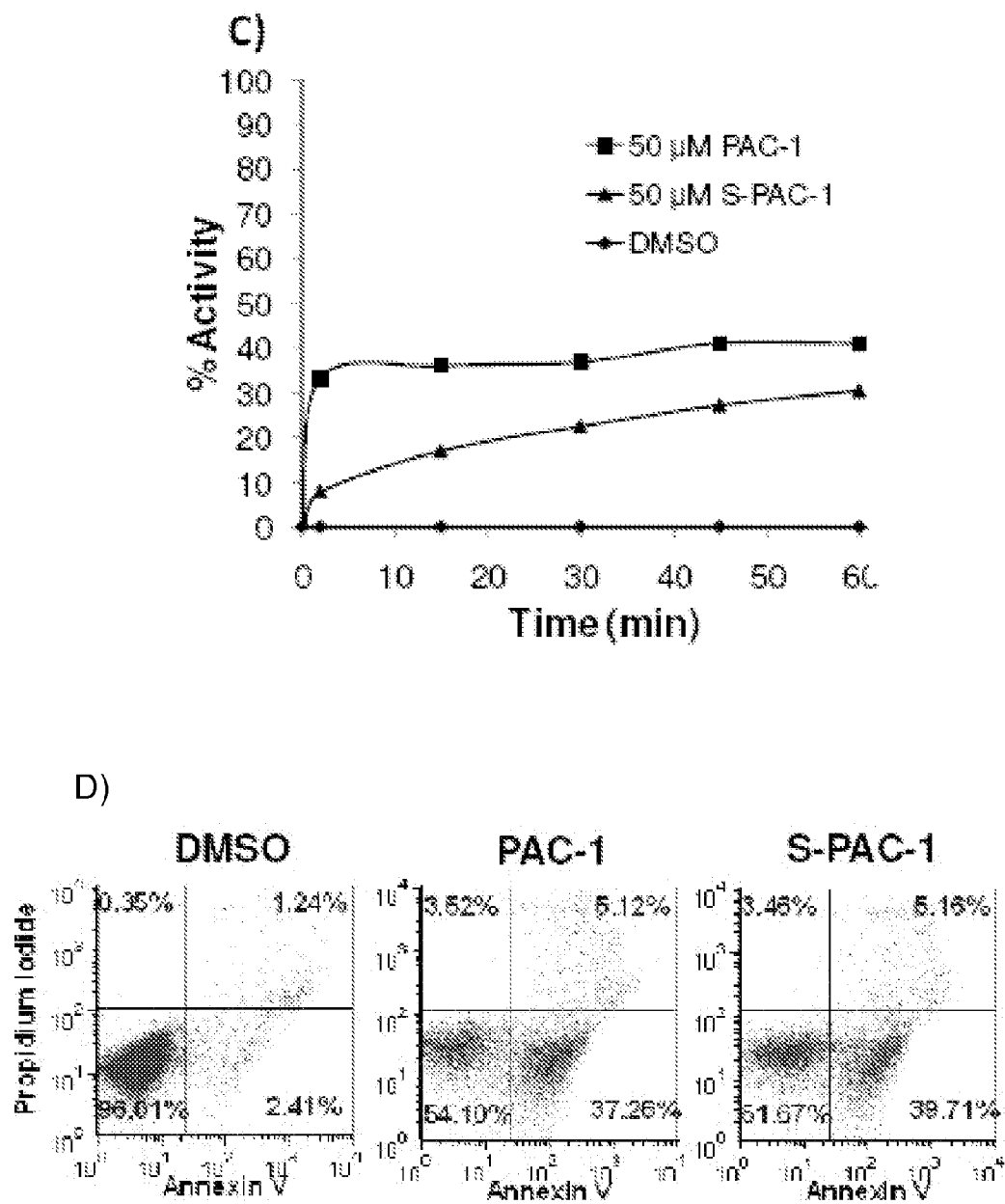
Figure 20:
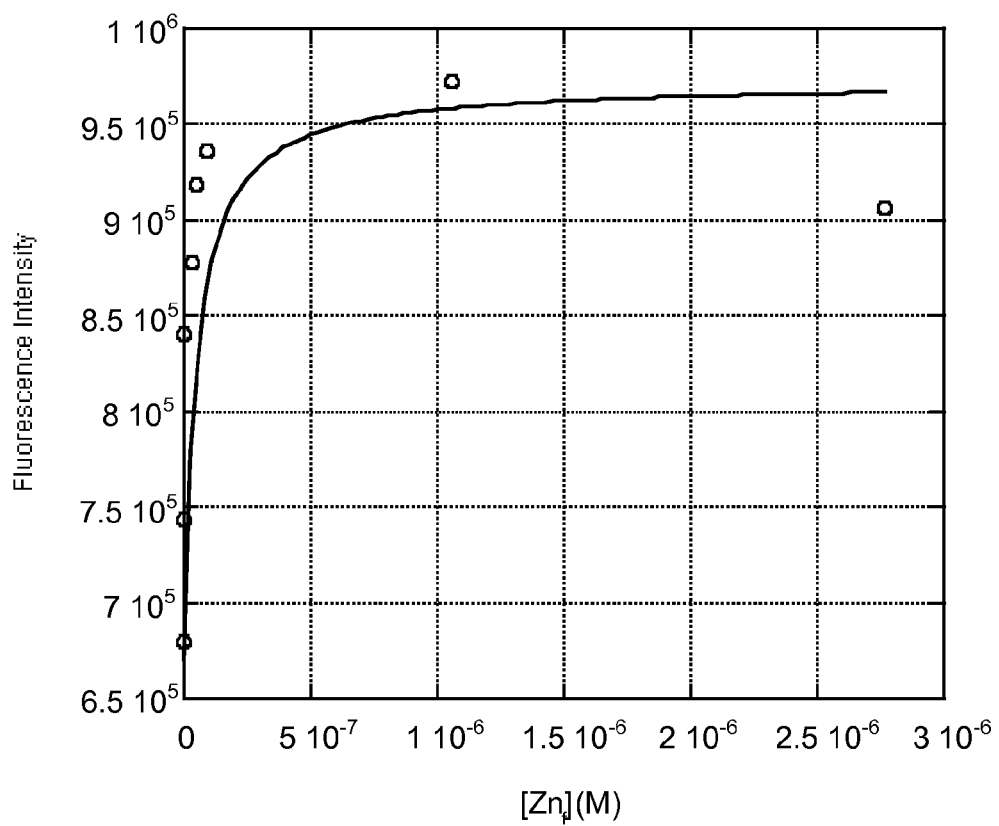
FIG. 20 shows a representative EGTA fluorescence titration assay data where S-PAC-1-Zn: $K_D$=46±5 nM.

S-PAC-1 binds zinc ions. The activity of S-PAC-1 was characterized in several biochemical assays. An EGTA competition titration experiment (31) was used to determine the binding constant for the S-PAC-1:$Zn^{2+}$ complex. In this experiment, a solution containing a known quantity of EGTA and S-PAC-1 was titrated with increasing concentrations of $Zn^{2+}$ and the fluorescence of S-PAC-1 was monitored at 475 nm. Changes in fluorescence in the presence of $Zn^{2+}$ were used to plot a formation curve (FIG. 16b). Using the known binding constant of EGTA, the free zinc concentration can be calculated and used to determine the binding constant of the S-PAC-1:$Zn^{2+}$ complex. This complex has a Kd of 46±5 nM compared to 52±2 nM for PAC-1:$Zn^{2+}$. (25) (FIG. 20).

EGTA Fluorescence Titration Assay—This titration assay is based on a published protocol. (Huang, Org. Lett. 2007, 9, 4999-5002). Before titration, cuvette was incubated with EDTA (10 mM) for 10 min, followed by sterile deionized water and acetone washing for removing any residue metal ions. PAC-1 or derivative (60 μM) was added to a cuvette containing buffer (Hepes: 50 mM, $KNO_3$: 100 mM, pH 7.2) with EGTA (7.3 mM) to achieve a 10-fold dilution (final PAC-1 concentration: 6 μM). $Zn(OTf)_2$ (0-10 mM) was added incrementally. The formation of Zn-PAC-1 (or derivative) complex was monitored by the increase in fluorescence intensity (ex/em: 410 nm/475 nm). Fluorescence intensity at 475 nm was plotted against free Zn concentration ($[Zn]_f$/M) calculated using MaxChelator program. (Patton, Cell Calcium, 2004, 35, 427-431). The data was analyzed using Kaleida-Graph and fitted to a formation curve based on Eq S1 derived by published protocol.

$$I=(I\min K_D+I\max[Zn]_f)/(K_D+[Zn]_f) \qquad \text{Eq S1}$$

where Imin and Imax were defined as the fluorescence intensity of the free probe (PAC-1 or derivative in this case) and that of the Zn-probe complex respectively.

S-PAC-1 activates procaspase-3 in vitro. The ability of S-PAC-1 to activate recombinantly expressed procaspase-3 in the presence of exogenous zinc in vitro was assessed. To ensure that the activity of the proenzyme was being monitored, a proteolytically uncleavable mutant of procaspase-3 (in which the three aspartic acid cleavage site residues are mutated to alanine (D9A/D28A/D175A)) was used (24,32). This recombinantly expressed protein was incubated in the presence of 10 μM zinc, and S-PAC-1 was added to the sample and the activity of the enzyme was monitored at 15 minute intervals. As shown in FIG. 16c, S-PAC-1 rapidly (within 5 minutes) enhances the enzymatic activity of the proenzyme by relief zinc-mediated inhibition.

S-PAC-1 induces cell death in multiple cancer cell lines in culture. Having confirmed that S-PAC-1 chelates zinc and activates procaspase-3 in vitro, the anticancer activity of S-PAC-1 was assessed against a panel of human, canine, and murine cancer cell lines. Cells were incubated with varying concentrations of compound for 72 hours after which cell death was assessed using a sulforhodamine B assay. (33) The IC50 values for PAC-1 and S-PAC-1 are reported in Table 1A. In most instances, S-PAC-1 is equipotent to PAC-1, although PAC-1 appears to be more potent in HeLa cells. Both PAC-1 and S-PAC-1 appear to be potent against all lymphoma cell lines tested regardless of the species of origin. Further analysis with U-937 cells shows that S-PAC-1 induces apoptosis in these cells. U-937 cells were treated with DMSO, 50 μM PAC-1 or 50 μM S-PAC-1 for 12 hours. After incubation, apoptosis was assessed by annexin V/PI staining and analyzed by flow cytometry (FIG. 16d). Both PAC-1 and S-PAC-1 treatment leads to an increase in the population of cells exhibiting annexin V staining. In this experiment, S-PAC-1 induces apoptosis to the same extent as PAC-1 (~40%).

In an effort to determine an appropriate treatment strategy for the evaluation of S-PAC-1 in vivo, the time dependency of S-PAC-1 cytotoxicity was evaluated. U-937 cells were treated with S-PAC-1 for various lengths of time. After treatment with S-PAC-1, cells were washed to remove compound and were cultured in growth media without compound. Cell death was assessed at 72 hours for all treatment times. An $IC_{50}$ value was determined for each exposure time and reported in Table 1B. At 3, 6 and 9 hours the $IC_{50}$ value was greater than the highest concentration tested. At 12 hours of exposure, a rapid reduction in the $IC_{50}$ value is observed. By 24 hours of exposure, the $IC_{50}$ value is near a minimum and shows little variation over the course of the subsequent 48 hours. These time dependency experiments suggest that S-PAC-1 will be most effective in vivo if cancer cells are exposed to the compound for at least 24 hours.

S-PAC-1 has no neurotoxic effect in mice. Having confirmed the activity of S-PAC-1 in vitro and in cell culture, the toxic effect of S-PAC-1 was assessed in C57/BL6 mice. In an analogous fashion to the toxicity determination of PAC-1, S-PAC-1 (solubilized with 2-hydroxypropyl-β-cyclodextrin) was administered to C57/BL6 mice via lateral tail vein injection at 12.5 mg/kg, 25 mg/kg, 37.5 mg/kg and 350 mg/kg. No neurotoxicity was observed even at the 350 mg/kg dose.

Figure 17:
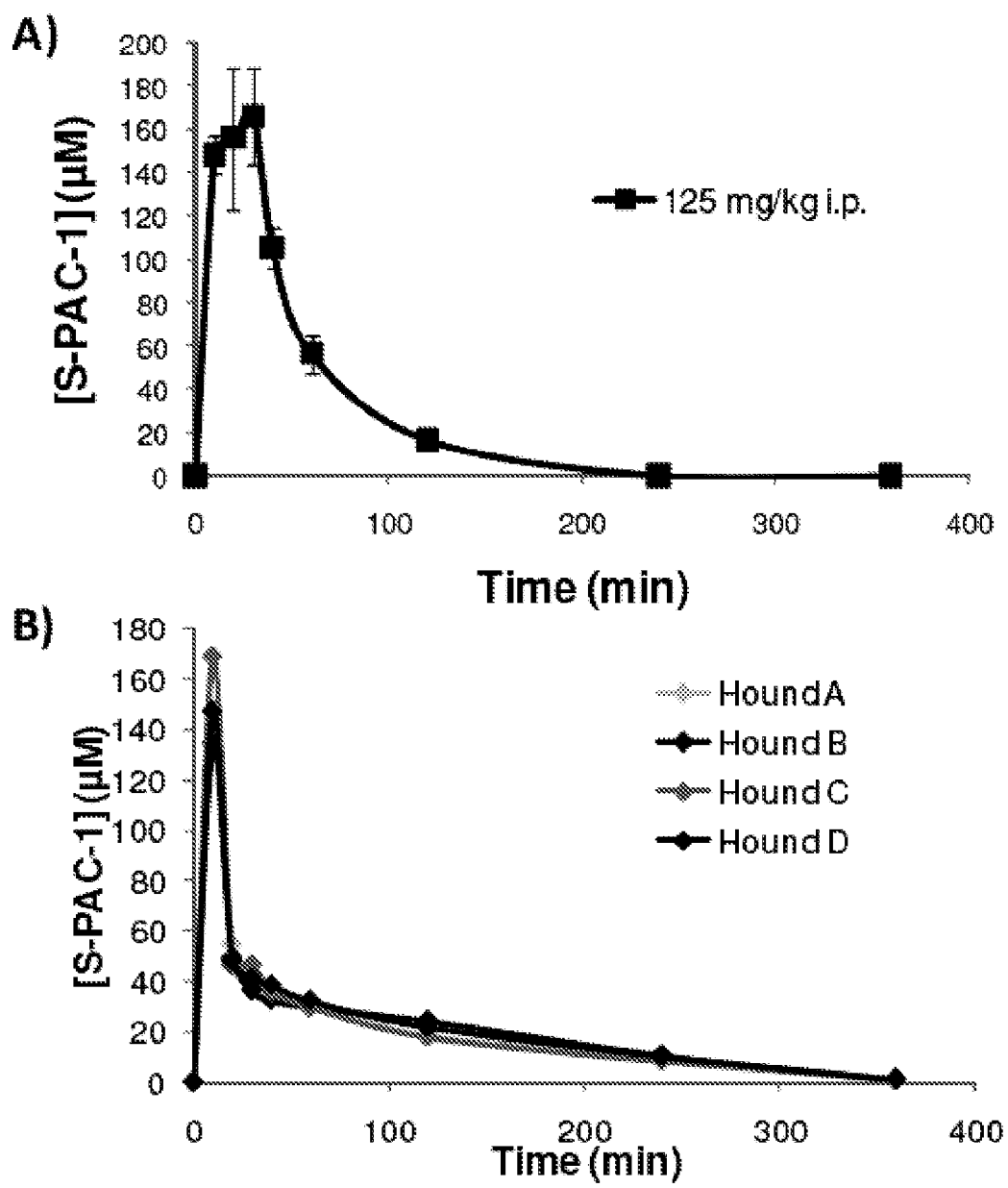
FIG. 17 shows characteristics of S-PAC-1. A) Pharmacokinetics of S-PAC-1 administered i.p. in mice. C57/BL6 mice were treated with 125 mg/kg of S-PAC-1 solublized in 2-hydroxypropyl-b-cyclodextrin via i.p. administration. Mice were sacrificed at various times and blood was drawn. The concentration of S-PAC-1 in the serum was determined by LC. 125 mg/kg S-PAC-1 has a peak plasma concentration of ~170 µM and a half life of ~1 hour. B) Pharmacokinetics of single-dose S-PAC-1 in research hound dogs. Four hound dogs were administered a single intravenous dose of S-PAC-1 (25 mg/kg in 2-hydroxypropyl-β-cyclodextrin), blood was drawn at various times, and S-PAC-1 concentration from serum was determined by LC. S-PAC-1 has a peak plasma concentration of ~150 µM and a half-life of ~3 hours in dogs. C) Three healthy hound dogs were administered a continuous infusion of S-PAC-1. Dogs received an initial loading dose over the course of 10 minutes followed by a constant rate infusion over the next 24 hours. Blood was drawn at various time points and S-PAC-1 concentration in the plasma was determined by LC analysis. Continuous infusion of S-PAC-1 was well-tolerated and successful in establishing a steady state serum concentration of S-PAC-1 in dogs.
Figure 17:
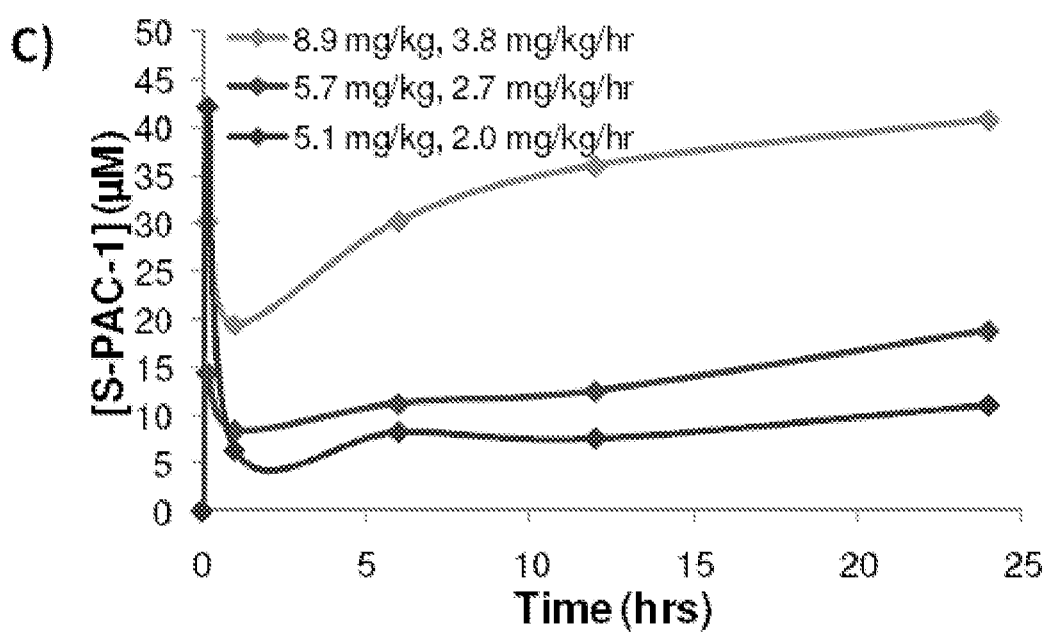

With the initial goal of assessing S-PAC-1 in murine tumor models, the pharmacokinetics of S-PAC-1 in mice was determined. If S-PAC-1 could be administered in a manner to allow for plasma concentrations of S-PAC-1 to exceed ~10 μM over the course of 24 hours, the treatment could be effective at inducing procaspase-3 activation and apoptosis in tumor cells. In order to develop a treatment strategy along these lines, C57/BL6 mice were treated with 125 mg/kg S-PAC-1 in 2-hydroxypropyl-β-cyclodextrin via i.p. administration. Mice were sacrificed and blood drawn at varying time points after administration. Blood samples were centrifuged and the serum was collected and analyzed by liquid chromatography to determine drug concentration. The drug concentration over time for S-PAC-1 is shown in FIG. 17A. The peak plasma concentration achieved by this dose is ~170 μM at 30 minutes after injection. The plasma concentration of S-PAC-1 then rapidly decreases with no S-PAC-1 remaining in the blood at 4 hours post injection. Analysis of this data indicates the elimination half life of S-PAC-1 to be ~1 hour in mice. Based on the peak plasma concentration achieved and the short half life of S-PAC-1 in mice, it was predicted that the mice would need to be treated with a 350 mg/kg dose of S-PAC-1 every two hours, to achieve and maintain a minimum plasma concentration of 10 μM over the course of 24 hours. Although this frequent dosing regimen for S-PAC-1 (i.p. every 2 hours for 24 hours) was technically feasible, further evaluation of S-PAC-1 as a novel therapeutic agent using murine tumor models was not methodologically practical. As such we sought to further investigate S-PAC-1 in a larger mammalian experimental system, specifically healthy and spontaneous cancer-bearing dogs, which conferred greater practicability for the maintenance of S-PAC-1 steady state concentrations for prolonged periods of time.

Assessment of S-PAC-1 in research dogs. Healthy research hound dogs were utilized for pharmacokinetic and toxicity investigations of S-PAC-1. Four research hound dogs were treated with 25 mg/kg S-PAC-1 (solubilized in 2-hydroxypropyl-β-cyclodextrin) via i.v. injection over 10 minutes. Multiple serum samples were collected over 24 hours to characterize the pharmacokinetic profile of intravenously administered S-PAC-1 in dogs. In addition to pharmacokinetic analysis, the hematologic and non-hematologic tolerability of single-dose, intravenous S-PAC-1 administration was monitored in research dogs weekly for 4 consecutive weeks. (Table 2A). As shown in FIG. 17B, the peak plasma concentration resulting from this 25 mg/kg i.v. bolus dose was ~150 μM, similar to that achieved in the mice treated with the 125 mg/kg i.p. dose. From analysis of the pharmacokinetic profile, the half life of S-PAC-1 in dogs was calculated to be 3 hours. Additionally, single-dose, intravenous S-PAC-1 treatment was well-tolerated by all 4 research dogs and no short or long term adverse events were observed with these animals as a result of treatment.

Although the half-life of 3 hours in dogs is a significant improvement over the half-life of S-PAC-1 in mice, pharmacokinetic calculations predicted that the drug would need to be administered several times during the course of a day to maintain serum levels above ~10 μM. Alternatively, continuous-rate infusion can be used to maintain a steady-state serum concentration of a drug during the course of the treatment. Continuous-rate infusion strategies have been used with other chemotherapeutic drugs such as dacarbazine (34), cytosine arabinoside (35), and gemcitabine (36) with infusion times up to 98 hours. Additionally, YM155, an investigational proapoptotic drug that exhibits increased activity with longer exposure times, is currently in clinical trials and utilizes a 168 hour continuous-rate infusion. (37)

Three healthy research dogs were utilized to determine if S-PAC-1 could be safely administered via a continuous-rate infusion regimen, and to determine appropriate dosing levels to maintain plasma concentrations above ~10 μM. Each dog received an initial loading dose via i.v. infusion over the course of 10 minutes followed by a maintenance dosage delivered by an infusion pump for an additional 24 hours. Each dog was observed throughout the course of their 24-hour infusions for adverse reactions and blood was drawn at intervals to assess the pharmacokinetic profile of S-PAC-1 treatment. In addition, following completion of S-PAC-1 infusion, research dogs were evaluated for hematologic and non-hematologic toxicity weekly for 4 consecutive weeks.

S-PAC-1 administered as a 24-hour continuous-rate infusion can be safely given to research dogs and easily reaches micromolar steady-state plasma concentrations. Pharmacokinetic profiles for the dogs administered S-PAC-1 in this manner show that steady state plasma concentrations correlate with dose escalation (FIG. 17C). Based on these results it was predicted that a 7 mg/kg loading dose and 3 mg/kg/hr constant rate infusion would be sufficient to achieve steady state plasma concentration of ~10 μM. Additionally, the continuous-rate infusion of S-PAC-1 was well tolerated at all doses examined and no hematologic or non-hematologic toxicities were observed in any of the research dogs.

Having confirmed the in vitro activity of S-PAC-1, shown that the compound can be safely administered via continuous-rate infusion, and that steady state plasma concentrations of S-PAC-1 of >10 μM may be achieved for a 24 hour duration, a small (n=5) clinical trial of client-owned pet dogs with spontaneous lymphoma was conducted. Spontaneously arising cancers in pet dogs share many similarities with human cancers including histologic appearance, tumor genetics, molecular targets, biologic and clinical behavior and response to therapy (38). Of these spontaneous canine cancers, multicentric lymphoma is the most common, occurring in 13 to 24 of every 100,000 dogs (39). The clinical progression and treatment of multicentric B-cell or T-cell canine lymphoma has many of the same characteristics of non-Hodgkin's lymphoma in humans. Canine lymphoma and human non-Hodgkin's lymphoma both respond clinically to the same cytotoxic drugs such as doxorubicin, vincristine and cyclophosphamide. These drugs are components of the CHOP treatment protocol, which is the first line therapy for diffuse large B-cell lymphoma in humans (40). When administered to dogs, the CHOP protocol will induce complete clinical remission in approximately 90% of dogs diagnosed with lymphoma (41,42). Similar to the human response, the majority of dogs who achieve remission with CHOP therapy will experience disease relapse (43). Given the commonalities between human and canine lymphoma, evaluation of S-PAC-1 in a canine lymphoma clinical trial provides important translational information for the development S-PAC-1 as a novel human therapeutic.

Inclusion criteria for S-PAC-1 trial. Dogs presented or referred to the University of Illinois-Urbana Champaign, College of Veterinary Medicine, Small Animal Clinic were considered for enrollment in the clinical trial. Inclusion criteria for eligible patients were the following: histologically or cytologically confirmed multicentric lymphoma; measurable tumor burden; favorable performance status; a life expectancy of >4 weeks; no previous chemotherapy within 3 weeks of study entry; and no significant co-morbid illness including renal or hepatic failure, history of congestive heart failure, or clinical coagulopathy. In addition, pet owners had to have signed a written informed consent form prior to study entry according to university guidelines.

Toxicity and pharmacokinetics of S-PAC-1 in canine lymphoma patients. Five patient dogs received treatment with S-PAC-1 via one of two treatment regimens (summarized in Table 7C). Patients enrolled in the first treatment regimen received a once-a-week 24 hour continuous infusion of S-PAC-1 for 4 weekly cycles. Patients enrolled in the second treatment regimen received a 72 hour continuous infusion of S-PAC-1 every other week for 2 treatment cycles. Blood was collected during each S-PAC-1 treatment cycle for pharmacokinetic analysis. In addition, blood was collected from all pet dogs at each scheduled follow up visit to characterize hematologic and non-hematologic toxicity. Between administrations, patients were monitored by pet owners for gastrointestinal toxicity observational scores adhering the Veterinary Co-operative oncology group common terminology and criteria for adverse events (VCOG_CTCAE) (44). All patients enrolled in either treatment regimens 1 or 2 did not demonstrate any clinically significant hematologic or non-hematologic toxicity (Table 7C and D). Only minor adverse events were reported by pet owners such as self-limiting and localized irritation at the infusion site (n=3), transient loss of appetite (n=1), and mild diarrhea (n=2). All adverse reactions subsided within 48 hours of the end of each treatment cycle.

Figure 18:
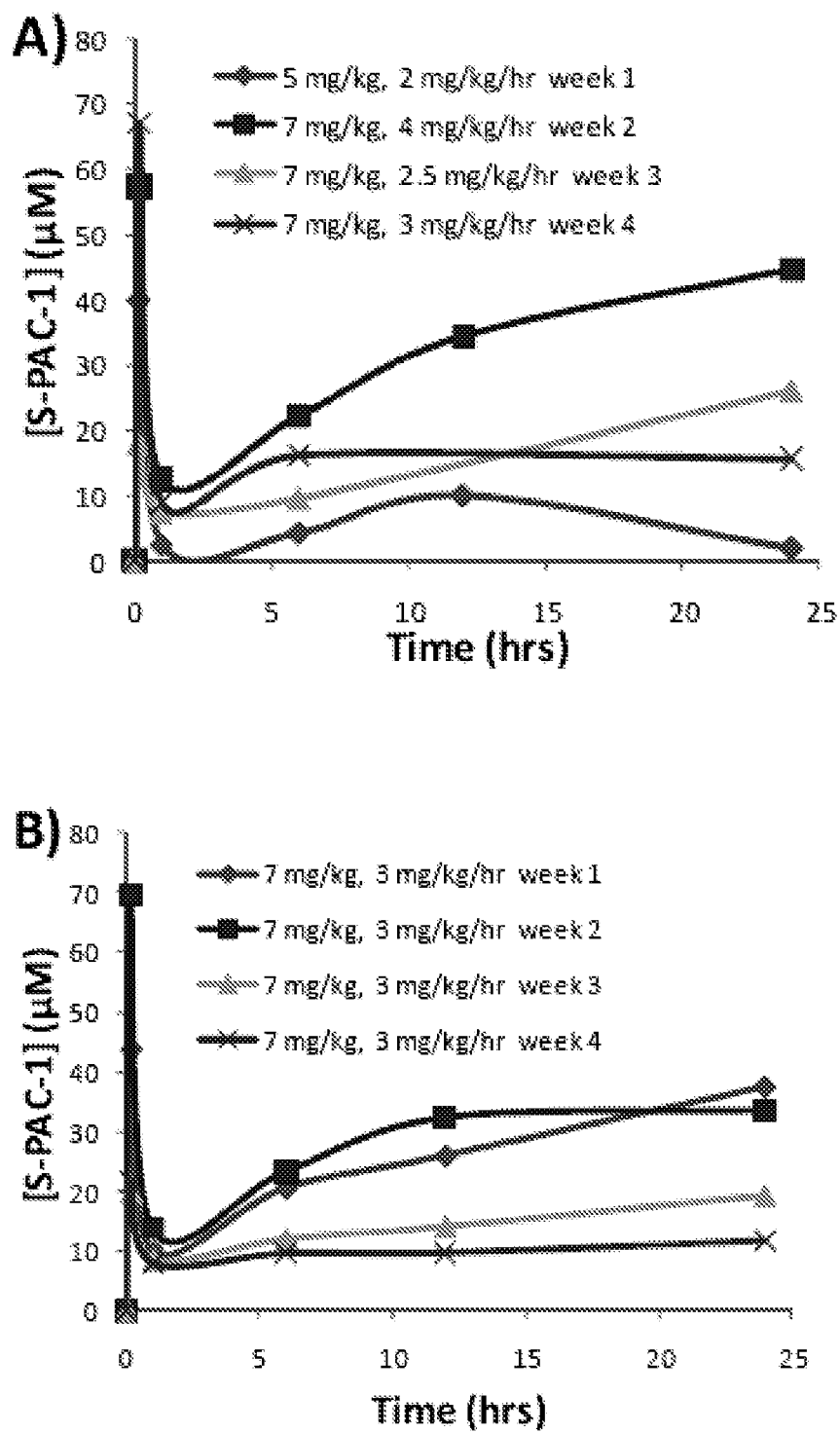
FIG. 18 shows pharmacokinetics of S-PAC-1 in lymphoma bearing dogs. Dogs enrolled in the clinical trial were administered S-PAC-1 at 7 mg/kg loading dose and 3 mg/kg/hr constant rate infusion for either 24 (A-C) or 72 (D-E) hours. Blood was drawn at various time points and the serum concentration of S-PAC-1 was determined by LC analysis.
Figure 18:
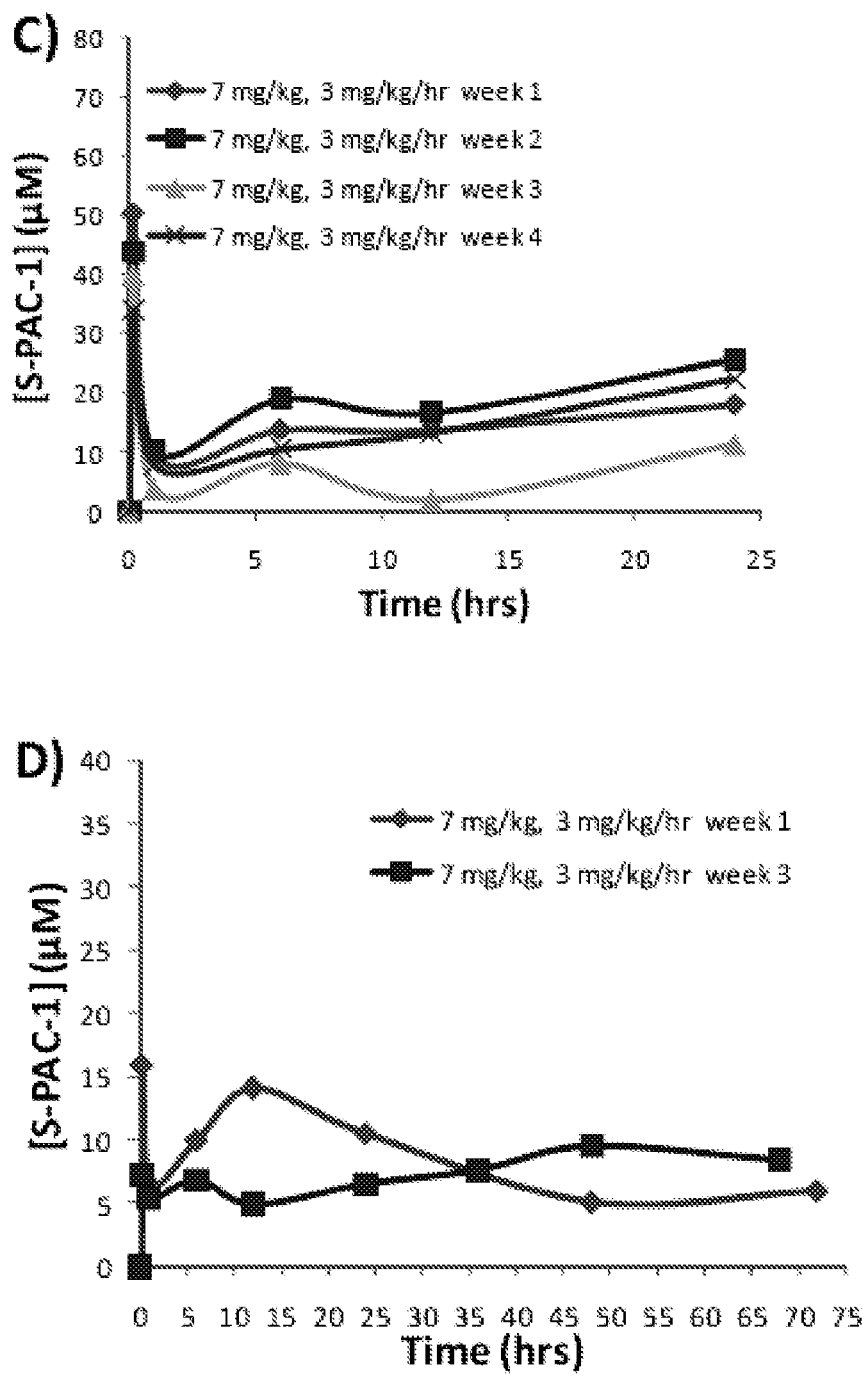
Figure 18:
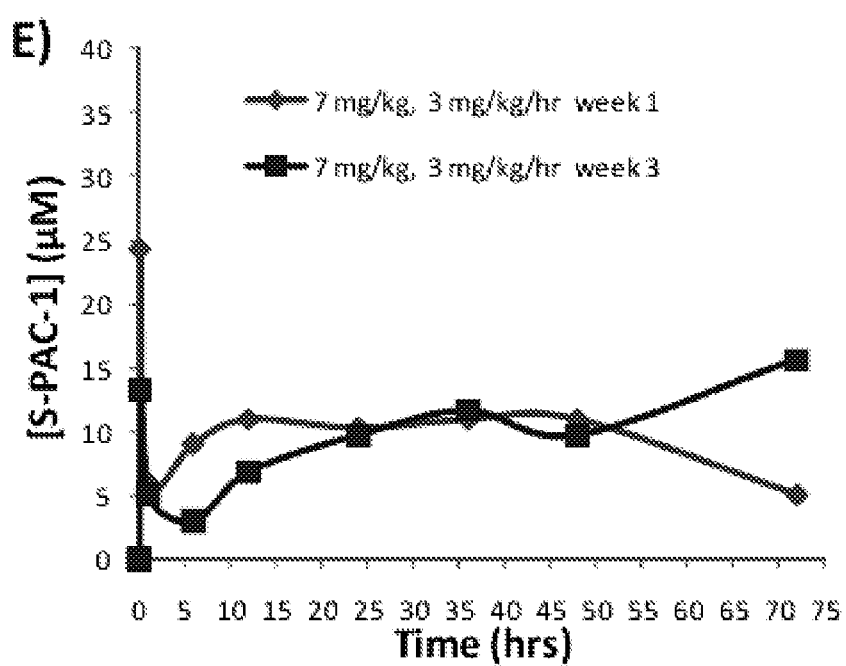

Pharmacokinetic analysis indicated that all patients had measurable serum concentrations of S-PAC-1, as shown in FIG. 18. S-PAC-1 concentrations reached a steady state within 6 hours of the beginning of infusion. In accordance with the prediction from the healthy research dogs, an infusion with a loading dose of 7 mg/kg and a constant rate infusion of 3 mg/kg/hr was sufficient to achieve steady state plasma concentrations of >10 µM in the majority of treatments.

Figure 19:
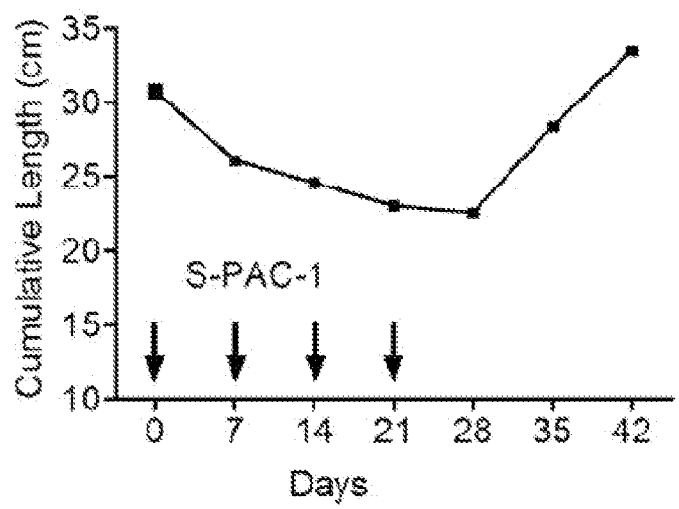
FIG. 19 shows anti-tumor effect of S-PAC-1 treatment. Top) RECIST scores for patient 1 over the course of 7 weeks. Arrows indicate treatment days. During the course of treatment patient 1 experienced a 27% decrease in RECIST score. After treatment ended, tumor size increased rapidly (day 42). Bottom) CT scans of the mandibular lymph nodes (outlined) indicate a significant decrease in tumor size prior to treatment (day 0) and one week after S-PAC-1 administration (Day 7).
Figure 19:
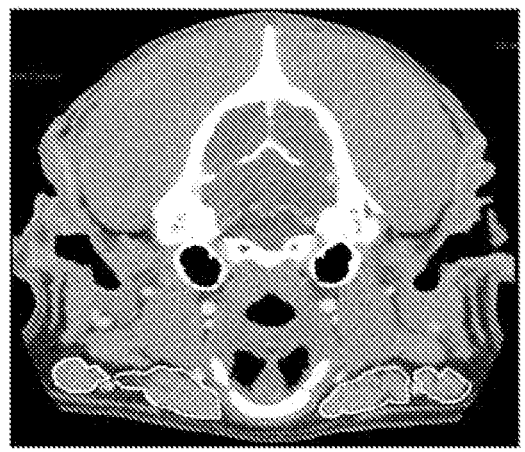
Figure 19:
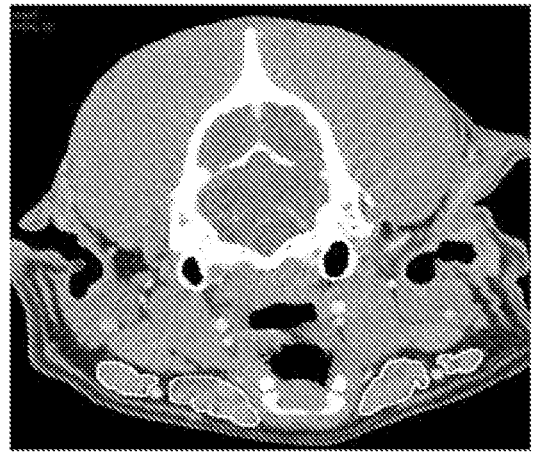

Antitumor activity of S-PAC-1. Assessment of tumor burden was monitored throughout the course of the study via cumulative caliper measurements of peripheral lymph nodes as well as CT scans of the mandibular lymph nodes. Caliper measurement was done according to the RECIST method (45). Briefly, the longest linear length measurement was recorded for 4 pairs of peripheral lymph nodes (mandibular, prescapular, inguinal, and popliteal), with the summation of these values giving a RECIST score. In addition to caliper measurements for all 4 sets of peripheral lymph nodes, CT scans were performed of the mandibular lymph nodes in every patient, allowing for accurate and objective measurement of maximal lymph node linear length. Of the 5 patients treated, one patient (patient 1) showed a partial response with a ~30% reduction in both RECIST score and the mandibular lymph node measurements by CT scan over the course of the 4 week treatment (FIGS. 19A and B). Following the four treatment cycles, drug administration was stopped and the dog was monitored by RECIST for 2 subsequent weeks. In the absence of treatment, the RECIST scores for this dog increased dramatically (day 36 and 42). In addition to this partial response, three patients showed stable disease (patients 2-4) while one patient showed disease progression (patient 5).

S-PAC-1 is the first compound in the PAC-1 class (and the first small molecule activator of procaspase-3) to be evaluated in a clinical trial of cancer patients. As such this data is important for the strategy of procaspase-3 activation as an anticancer therapy. It is perhaps not surprising that high doses of PAC-1 induce neurotoxicity, given the mechanism of action of the compound and its predicted permeability of the BBB. Further, the brief lag in onset of this neurotoxicity (~5 minutes) suggests that the neurotoxicity observed is not a result of the initial peak plasma concentration of PAC-1, but rather the result of a redistribution of PAC-1 across the BBB. Zinc homeostasis is important in the central nervous system (46), and NMDA receptors require bound zinc to provide a tonic inhibition (28). NMDA receptors bind zinc with a low affinity ($K_d$=5.5 µM) (47) which suggests that a zinc chelator with a higher affinity for zinc such as PAC-1 or S-PAC-1 ($K_d$=46 and 52 nM respectively) would be able to successfully sequester zinc from these receptors. Several studies indicate that intracellular zinc chelation results in hyperexcitation of these receptors (27), resulting in symptoms such as uncontrolled muscle movement and seizure (28). Indeed a cell permeable zinc chelator, TPEN, has been shown to induce severe neurotoxicity in mice at low concentrations and rapid death at higher concentrations (48).

There are several factors that affect the permeability of a compound through the BBB including polarity, lipophillicity, and size (29). One strategy for reducing the permeability of a compound to the BBB is to increase the polarity of the molecule. Addition of the sulfonamide functional group is a good candidate for such polarity increase as the aryl sulfonamide motif is common in a number of small molecule therapeutics. FDA approved drugs containing the aryl sulfonamide functional group include Celecoxib (Celebrex®), Tamsulosin (Flomax®), and hydrochlorothiazide.

Pet dogs with lymphoma represent a significant tool for the investigation of investigational new drugs (26). Nearly 1 in 4 pet dogs in the US die from cancer (49), and without treatment the mean survival time from diagnosis is 4-6 weeks. The standard of care for dogs with lymphoma is administration of CHOP therapy (26). This therapy consists of 16 courses of drug administration over 19 weeks and usually results in complete remission. Similar to the human disease, the majority of dogs that achieve remission will experience relapse often accompanied by drug resistance. As such, new pharmacophores are needed to address both primary and recurrent lymphoma. As shown in Table 6C, one dog enrolled in the current study (patient 1) was in remission for 5 months after CHOP therapy, and was recently diagnosed with recurrent lymphoma. Upon enrollment in the study this dog showed a 27% decrease in tumor size in response to S-PAC-1 treatment. This partial response is significant given the comparatively short treatment duration (4 weeks for S-PAC-1 vs. 19 weeks for CHOP). It is encouraging that four out of five patients achieved partial response or stable disease for 4 weeks in duration, as canine lymphoma is generally a rapidly progressive malignancy with dramatic enlargement of peripheral lymph nodes within weeks of disease diagnosis. This is further illustrated by the rapid enlargement observed in the lymph nodes of patient 1 after cessation of treatment.

Compounds in the PAC-1 class activate procaspase-3 via chelation of inhibitory zinc ions (25). Intracellular zinc is found principally in tightly-bound complexes in metalloproteases, zinc-finger domains, and other metal binding proteins; however, approximately 10% of cellular zinc is believed to exist in a loosely-bound, labile pool (50). A number of studies implicate labile zinc as an endogenous antiapoptotic regulator (51-54). Interestingly, chelation of the loosely-bound pool of zinc is an emerging anti-cancer strategy (24,25). Recently, another small molecule zinc chelator, ML-133, was reported to have anti-cancer properties in vitro and in a murine xenograft model of colon cancer (55). Although not reported by the authors, ML-133 may act in a similar manner to PAC-1 and S-PAC-1 (i.e. activation of procaspase-3). Thus, the evaluation of S-PAC-1 also is useful in the chelation of the labile zinc pool as an anti-cancer strategy.

In conclusion, S-PAC-1 is a potent cytotoxic small molecule with similar activity to the parent compound, PAC-1. While high doses of PAC-1 (when administered in 2-hydroxypropyl-β-cyclodextrin) induce neurotoxicity in vivo, S-PAC-1 does not cause this side-effect. S-PAC-1 can be safely administered to mice, research dogs, and lymphoma bearing dogs, and shows encouraging clinical effect in this preliminary one-dosage evaluation. Given the absence of neurotoxicity with S-PAC-1 it is anticipated that S-PAC-1 will prove to be safe at even higher doses than those evaluated here. A full canine clinical trial of S-PAC-1 including dose escalation in lymphoma dogs is currently underway.

TABLE 6

A) Cytotoxicity analysis of PAC-1 and S-PAC-1 in various cancer cell lines in culture. B) Time dependence of S-PAC-1 cytotoxicity in U-937 cells. C) Characteristics of the five lymphoma bearing dogs treated with S-PAC-1.

A)

| Cell line | Species | Origin | PAC-1 $IC_{50}$ Value (μM) | S-PAC-1 $IC_{50}$ Value (μM) |
|---|---|---|---|---|
| U-937 | Human | Lymphoma | 9.3 ± 0.5 | 7.7 ± 1.2 |
| EL-4 | Mouse | Lymphoma | 3.8 ± 0.9 | 7.1 ± 1.3 |
| 17-71[a] | Dog | Lymphoma | 2.5 ± 0.9 | 2.7 ± 0.8 |
| GL-1 | Dog | Lymphoma | 4.9 ± 0.3 | 7.1 ± 0.3 |
| OSW | Dog | Lymphoma | 8.6 ± 1.3 | 11.0 ± 0.9 |
| Jurkat | Human | Leukemia | 5.7 ± 2.8 | 4.5 ± 1.1 |
| SK-Mel-5 | Human | Melanoma | 11.5 ± 3.6 | 8.6 ± 1.3 |
| HeLa | Human | Cervical | 15.5 ± 3.8 | 28.4 ± 7.7 |
| MDA-MB-231 | Human | Breast | 9.9 ± 1.0 | 11.7 ± 5.3 |

B)

| Exposure Time (hr) | $IC_{50}$ (μM) |
|---|---|
| 1 | >100 |
| 3 | >100 |
| 6 | >100 |
| 9 | 20 ± 12 |
| 12 | 9.7 ± 1.1 |
| 24 | 5.9 ± 1.0 |
| 48 | 5.6 ± 0.8 |
| 72 | 5.2 ± 0.3 |

C)

| Patient | Breed | Male/Female | Age | Weight (lb) | Immunophenotype | Prior Therapy | Treatment |
|---|---|---|---|---|---|---|---|
| 1 | Mixed Breed | Castrated Male | 7 | 79 | B-Cell Lymphoma | CHOP | 24 hr |
| 2 | Labrador Retriever | Spayed Female | 7 | 89 | T-Cell Lymphoma | Naïve | 24 hr |
| 3 | Newfoundland | Intact Male | 4 | 160 | T-Cell Lymphoma | Naïve | 24 hr |
| 4 | Corgi | Spayed Female | 8 | 50 | B-Cell Lymphoma | Naïve | 72 hr |
| 5 | Golden Retriever | Spayed Female | 7 | 80 | B-Cell Lymphoma | Naïve | 72 hr |

[a]This cell line was assessed using the MTS cell viability assay.

TABLE 7

A) Select hematologic and non-hematologic parameters of research dogs treated with single dose of S-PAC-1, C) lymphoma bearing dogs treated with S-PAC-1 in a 24 hour continuous rate infusion every week for 4 consecutive treatments, and D) lymphoma bearing dogs treated with S-PAC-1 in a 72 hour constant rate infusion every other week for 2 consecutive treatments.

A)

| Parameter | Reference range | Day 0 | Day 7 | Day 14 | Day 21 |
|---|---|---|---|---|---|
| WBC | 6.0-17.0 × 1000 | 8.1 | 8.1 | 9 | 9.6 |
| Neutrophil | 3.0-11.5 × 1000 | 4.4 | 5 | 5.1 | 5.2 |
| Platelet | 1.5-9.0 × 100000 | 1.4 | 2 | 1.7 | 1.7 |
| Creatinine | 0.5-1.6 mg/ml | 0.7 | 0.8 | 0.6 | 0.8 |
| Liver ALT | 17.0-87.0 U/L | 31 | 29 | 29 | 30 |

C)

TABLE 7-continued

A) Select hematologic and non-hematologic parameters of research dogs treated with single dose of S-PAC-1, C) lymphoma bearing dogs treated with S-PAC-1 in a 24 hour continuous rate infusion every week for 4 consecutive treatments, and D) lymphoma bearing dogs treated with S-PAC-1 in a 72 hour constant rate infusion every other week for 2 consecutive treatments.

| Parameter | Reference Range | Day 0 | Day 7 | Day 14 | Day 21 | Day 28 |
|---|---|---|---|---|---|---|
| WBC | $6\text{-}17.0 \times 10^3$ | 8.8 ± 3.3 | 11.1 ± 4.2 | 9.7 ± 3.1 | 11.0 ± 3.9 | 10.1 ± 2.4 |
| Neutrophil | $3\text{-}11.5 \times 10^3$ | 6.7 ± 0.6 | 8.7 ± 0.8 | 7.2 ± 0.5 | 8.8 ± 1.1 | 7.6 ± 0.4 |
| Platelet | $2\text{-}9 \times 10^5$ | 2.6 ± 0.5 | 2.6 ± 0.8 | 2.7 ± 0.7 | 2.7 ± 1.0 | 2.4 ± 1.0 |
| Creatinine | 0.5-1.6 mg/dl | 1.2 ± 0.1 | 1.1 ± 0.1 | 1.2 ± 0.1 | 1.2 ± 0.2 | 1.6 ± 0.9 |
| ALT | 17-87 U/L | 50.7 ± 19.9 | 46.3 ± 11.0 | 41.0 ± 13.2 | 43.0 ± 15.5 | 53.0 ± 30.5 |
| BUN | 7.0-31.0 mg/dl | 17.2 ± 2.6 | 14.0 ± 1.6 | 14.6 ± 1.1 | 15.5 ± 2.8 | 24.5 ± 16.7 |
| Sodium | 141-161 mEq/L | 148.7 ± 2.1 | 145.3 ± 2.1 | 147.0 ± 1.7 | 149.3 ± 3.2 | 149.7 ± 1.5 |
| Potassium | 3.9-5.7 mEq/L | 4.4 ± 0.3 | 4.3 ± 0.2 | 4.4 ± 0.3 | 4.4 ± 0.4 | 4.0 ± 0.6 |
| Chloride | 104-125 mEq/L | 117.0 ± 1.0 | 111.3 ± 3.1 | 113.3 ± 1.5 | 118.0 ± 1.7 | 113.7 ± 4.9 |
| Calcium | 7.9-11.5 mg/dl | 11.3 ± 1.9 | 11.7 ± 2.1 | 11.4 ± 2.5 | 11.0 ± 1.1 | 12.0 ± 2.7 |
| Phosphorous | 2.4-6.5 mg/dl | 3.6 ± 1.0 | 3.5 ± 0.3 | 3.2 ± 0.3 | 3.2 ± 0.6 | 3.8 ± 0.8 |
| ALP | 1.2-110 U/L | 26.7 ± 11.2 | 37.3 ± 18.4 | 45.7 ± 16.5 | 45.0 ± 18.5 | 49.0 ± 20.7 |
| Bilirubin | 0.08-0.5 mg/dl | 0.1 ± 0.1 | 0.1 ± 0.1 | 0.1 ± 0.1 | 0.1 ± 0.0 | 0.1 ± 0.1 |

D)

| Parameter | Reference Range | Day 0 | Day 14 | Day 28 |
|---|---|---|---|---|
| WBC | $6\text{-}17.0 \times 10^3$ | 18.4 ± 5.3 | 11.8 ± 2.4 | 18.3 ± 12.2 |
| Neutrophil | $3\text{-}11.5 \times 10^3$ | 13.5 ± 1.4 | 8.1 ± 2.3 | 12.3 ± 0.8 |
| Platelet | $2\text{-}9 \times 10^5$ | 2.8 ± 0.8 | 2.7 ± 0.8 | 2.5 ± 0.0 |
| Creatinine | 0.5-1.6 mg/dl | 0.8 ± 0.2 | 0.7 ± 0.3 | 0.7 ± 0.2 |
| ALT | 17-87 U/L | 73.0 ± 42.4 | 81.0 ± 58.0 | 57.5 ± 46.0 |
| BUN | 7.0-31.0 mg/dl | 13.2 ± 4.5 | 16.0 ± 0.1 | 12.7 ± 0.9 |
| Sodium | 141-161 mEq/L | 148.0 ± 5.7 | 148.0 ± 0.0 | 148.0 ± 1.4 |
| Potassium | 3.9-5.7 mEq/L | 4.6 ± 0.2 | 4.2 ± 0.1 | 4.4 ± 0.0 |
| Chloride | 104-125 mEq/L | 117.5 ± 0.7 | 116.5 ± 3.5 | 115.0 ± 1.4 |
| Calcium | 7.9-11.5 mg/dl | 9.8 ± 0.7 | 9.9 ± 0.4 | 9.9 ± 0.3 |
| Phosphorous | 2.4-6.5 mg/dl | 4.3 ± 0.1 | 5.7 ± 0.3 | 3.5 ± 1.0 |
| ALP | 12-110 U/L | 98.0 ± 65.1 | 63.0 ± 65.1 | 81.5 ± 75.7 |
| Bilirubin | 0.08-0.5 mg/dl | 0.2 ± 0.1 | 0.2 ± 0.1 | 0.2 ± 0.1 |

WBC—white blood cell, ALT—alanine transferase, BUN—blood urea nitrogen, ALP—alkaline phosphatase

Materials and Methods

General

All reactions requiring anhydrous conditions were conducted under a positive atmosphere of nitrogen or argon in oven-dried glassware. Standard syringe techniques were used for anhydrous addition of liquids. Dry tetrahydrofuran was obtained by passing over activated alumina columns or molecular sieves in a commercial solvent purification system (Innovative Technologies). Unless otherwise noted, all starting materials, solvents, and reagents were acquired from commercial suppliers and used without further purification. Flash chromatography was performed using 230-400 mesh silica gel. Compound 1, 2, and 5 (Naganawa, Bioorg Med Chem, 2006, 14, 7121-7137). were prepared according to the literature methods.

Compound Analysis

All NMR experiments were recorded either in $D_2O$ (Sigma), $CD_3OD$ (sigma) or Acetone-d6 (Sigma) on a Varian Unity 400 MHz or 500 MHz spectrometer with residual undeuterated solvent as the internal reference. Chemical shift, δ (ppm); coupling constants, J (Hz); multiplicity (s=singlet, d=doublet, t=triplet, q=quartet, m=multiplet); and integration are reported. High-resolution mass spectral data was recorded on a Micromass Q-T of Ultima hybrid quadrupole/time-of-flight ESI mass spectrometer at the University of Illinois Mass Spectrometry Laboratory. All melting points are uncorrected. LC-MS performed on a C18 column, 2.1×5 mm, mobile phase A is 0.1% TFA in $H_2O$, B is acetonitrile using a gradient system with constant 0% B over 0-2 min, then 0-50% B from 2-5 min, then 50-100% B over 5-7 min, constant 100% over 7-8 min, and from 100-0% over 8-10.

Scheme 7. Minigram-scale synthesis of S-PAC-1.

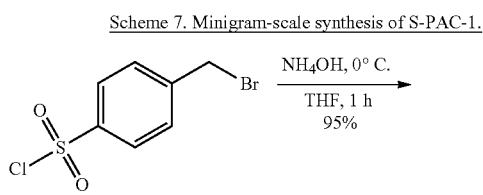

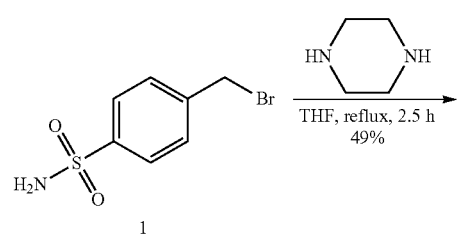

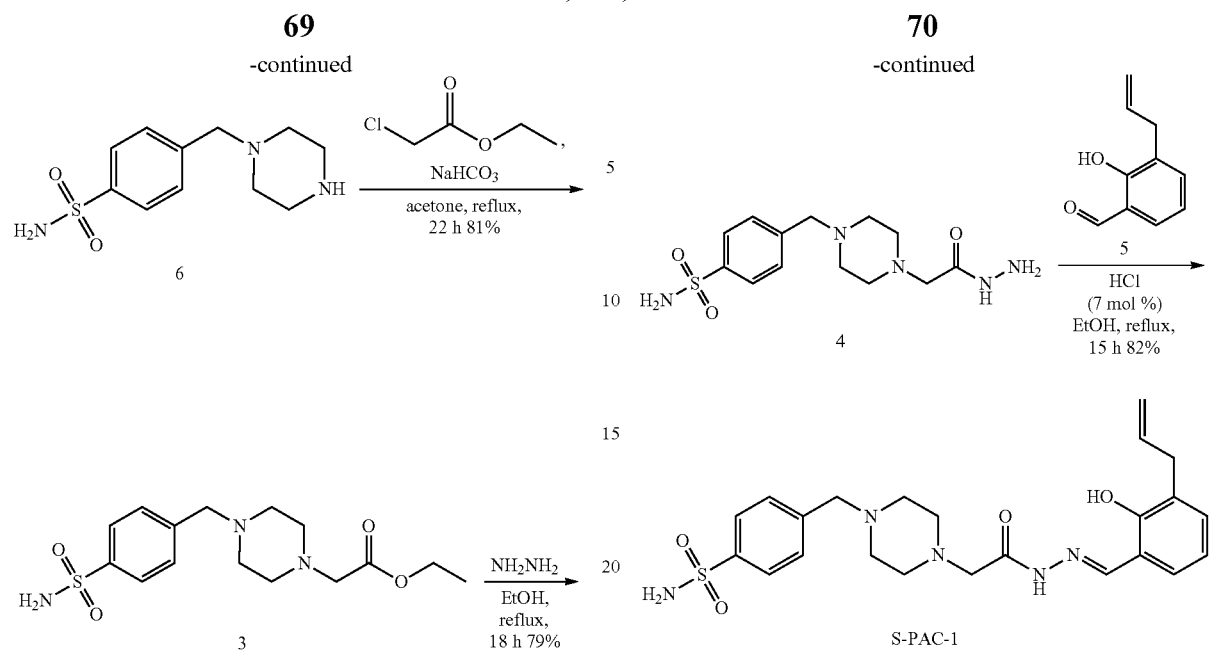
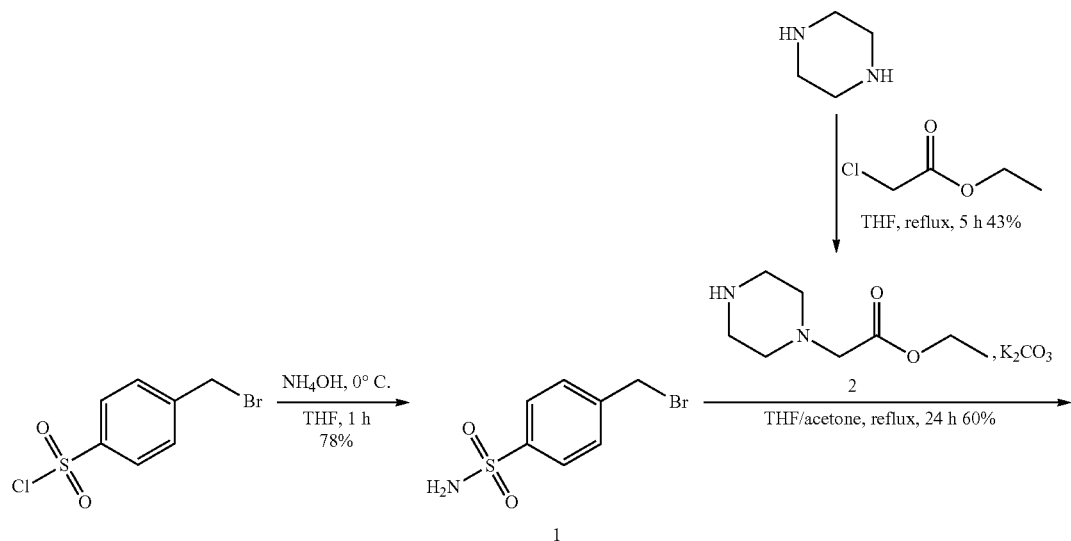
Scheme 8. Gram-scale synthesis of S-PAC-1.
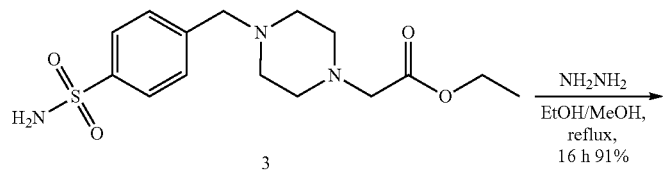

-continued

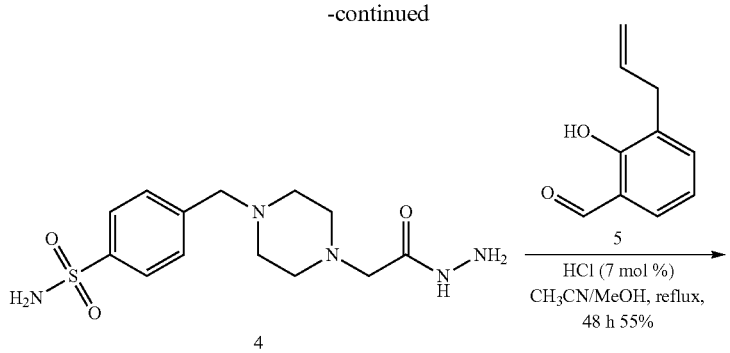

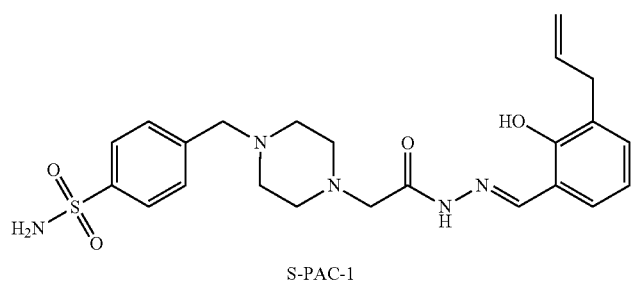

S-PAC-1

Ethyl 2-(4-(4-sulfamoylbenzyl)piperazin-1-yl)acetate (3)

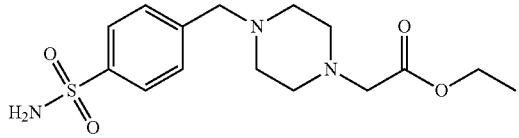 [SMILES: CCOC(=O)CN1CCN(Cc2ccc(S(N)(=O)=O)cc2)CC1]

To a stirred mixture of 1 (108 g, 440.7 mmol, 1.4 equiv.) and $K_2CO_3$ (132.4 g, 958.2 mmol, 3 equiv.) in 3:2 THF/acetone (2192 mL in total) was added ethyl 2-(piperazin-1-yl)acetate, 2 (79.9 g, 319.4 mmol, 1 equiv.). The reaction was refluxed for 24 h monitoring by TLC. The solution was filtered and the solid was washed with acetone (80 mL). The filtrate was concentrated in vacuo, and then purified by recrystallization in ethanol to afforded 3 (57.4 g, 60%) as light yellow solid. On the milligram-scale, the crude product was purified by flash column chromatography on silica gel (1:4 MeOH/EtOAc). $^1$H-NMR (500 MHz, $CD_3OD$): δ 7.86 (d, J=8.0 Hz, 2H), 7.52 (d, J=8.0 Hz, 2H), 4.17 (q, J=7.1 Hz, 2H), 3.61 (s, 2H), 3.24 (s, 2H), 2.58 (broad d, J=50.4 Hz, 8H), 1.26 (t, J=7.1 Hz, 3H). $^{13}$C NMR (126 MHz, $CD_3OD$): δ 170.4, 142.8, 142.4, 129.7, 126.0, 61.9, 60.6, 58.5, 52.5, 52.4, 13.3. HRMS (ESI): found 342.1487 (M+1). calcd for $C_{15}H_{24}N_3O_4S$: 342.1488. m.p.: 153.0-154.5. IR (neat): 3319, 1739, 1160 cm$^{-1}$.

4-((4-(2-hydrazinyl-2-oxoethyl)piperazin-1-yl)methyl)benzenesulfonamide (4)

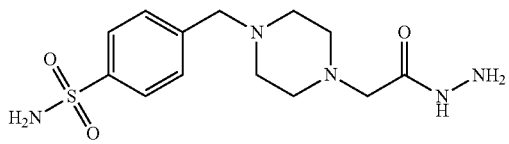 [SMILES: NNC(=O)CN1CCN(Cc2ccc(S(N)(=O)=O)cc2)CC1]

To a stirred solution of 3 (110.9 g, 324.8 mmol, 1 equiv.) in 2:1 ethanol/methanol (650 mL in total, 0.5 M) was added anhydrous hydrazine (30.6 mL, 974.5 mmol, 3 equiv.). The reaction was refluxed for 16 h monitoring by TLC (1:1 MeOH/EtOAc). The reaction mixture was concentrated in vacuo. The residue was dissolved in $CH_2Cl_2$ and washed with water (100 mL) and brine (100 mL). The aqueous layer was extracted with $CH_2Cl_2$ (3×80 mL) and EtOAc (80 mL). The combined organic layer was dried over $Na_2SO_4$, filtered and concentrated in vacuo. Purification with recrystallization in methanol gave 4 (96.3 g, 91%) as white solid. On the milligram-scale, the reaction was run in ethanol (0.06 M). $^1$H NMR (500 MHz, $CD_3OD$): δ 7.85 (d, J=8.2 Hz, 2H), 7.51 (d, J=8.2 Hz, 2H), 3.61 (s, 2H), 3.04 (s, 2H), 2.54 (broad s, 8H). $^{13}$C NMR (126 MHz, $CD_3OD$): δ 170.2, 142.8, 142.4, 129.7, 126.0, 61.9, 59.8, 53.0, 52.6. HRMS (ESI): found 328.1436 (M+1). calcd for $C_{13}H_{22}N_5O_3S$: 328.1443. m.p.: 194.5-196.0. IR (neat): 3320, 1670, 1158 cm$^{-1}$.

(E)-4-((4-(2-(2-(3-allyl-2-hydroxybenzylidene)hydrazinyl)-2-oxoethyl)piperazin-1-yl)methyl)benzenesulfonamide (S-PAC-1)

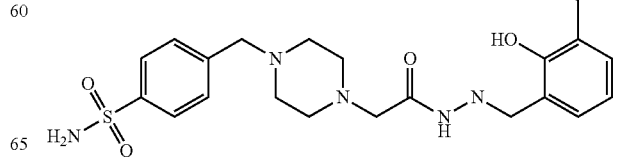

To a stirred solution of 5 (28.8 g, 177.3 mmol, 1 equiv.) in 1:2 acetonitrile/methanol (1180 mL in total, 0.15 M), 4 (98.7 g. 301.4 mmol, 1.7 equiv.) and HCl (7 mol %) were added. The reaction was refluxed for 48 h monitoring by TLC. The solution was concentrated in vacuo. The crude product was purified by flash column chromatography on silica gel (1:4 MeOH/EtOAc), and followed by recrystallization in methanol to afford S-PAC-1 (45.9 g, 55%) as off-white solid. On the milligram-scale, the reaction was run in ethanol (0.02 M). $^1$H NMR (500 MHz, (CD$_3$)$_2$CO): δ 11.86 (s, 1H), 10.79 (s, 1H), 8.51 (s, 1H), 7.85 (d, J=8.2 Hz, 2H), 7.53 (d, J=8.2 Hz, 2H), 7.19 (d, J=7.6 Hz, 2H), 6.86 (t, J=7.6 Hz, 1H), 6.56 (s, 2H), 6.02 (tdd, 1H, J=6.7 Hz, J=10.1 Hz, J=16.9 Hz), 5.04 (m, 2H), 3.60 (s, 2H), 3.42 (d, J=6.7 Hz, 2H), 3.18 (s, 2H) 2.57 (broad d, J=46.5 Hz, 8H). $^{13}$C NMR (126 MHz, (CD$_3$)$_2$CO): δ 165.7, 156.4, 150.0, 143.4, 143.2, 136.9, 131.8, 129.32, 129.30, 127.9, 126.2, 119.1, 117.8, 115.1, 62.0, 61.1, 53.7, 52.9, 33.8. HRMS (ESI): found 472.2014 (M+1). calcd for C$_{23}$H$_{30}$N$_5$O$_4$S: 472.2019. m.p.: 108.5-111.0. IR (neat): 3227, 1684, 1606, 1157 cm$^{-1}$. Purity: >99.5% (LC-MS).

4-(piperazin-1-ylmethyl)benzenesulfonamide (6)

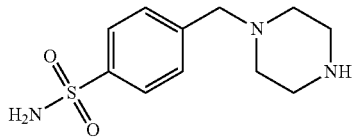 [SMILES: NS(=O)(=O)c1ccc(CN2CCNCC2)cc1]

Anhydrous piperazine (860 mg, 10.0 mmol, 5 equiv.) was added to THF (10 mL), and the mixture was heated to reflux until the piperazine was fully dissolved. To the solution 1 (500 mg, 2.0 mmol, 1 equiv.) was added. The reaction mixture was refluxed for 2.5 hr monitoring by TLC. The reaction mixture was neutralized with 1M KOH solution, and then concentrated in vacuo. Purification with flash column chromatography on silica gel (1:4 MeOH/EtOAc) afforded 6 (250 mg, 49%) as light yellow semi-solid. $^1$H NMR (400 MHz, D$_2$O/(OD$_3$)$_2$CO): δ 7.84 (d, J=8.4 Hz, 2H), 7.51 (d, J=8.4 Hz, 2H), 3.69 (s, 2H), 3.42 (s, 2H), 3.22 (m, 4H), 2.74 (m, 4H), 1.87 (apparent s, 1H). $^{13}$C NMR (126 MHz, CDCl$_3$): δ 140.93, 140.87, 131.0, 126.3, 61.1, 49.0, 43.13. HRMS (ESI): found 256.1114 (M+1). calcd for C$_{11}$H$_{18}$N$_3$O$_2$S: 256.1120. IR (neat): 3142, 1158 cm$^{-1}$.

Example 7

Pharmaceutical Embodiments

The following describes information relevant to pharmaceutical and pharmacological embodiments and is further supplemented by information in the art available to one of ordinary skill. The exact formulation, route of administration and dosage can be chosen by an individual physician in view of a patient's condition (see e.g. Fingl et. al., in The Pharmacological Basis of Therapeutics, 1975, Ch. 1 p. 1).

It should be noted that the attending physician would know how to and when to terminate, interrupt, or adjust administration due to toxicity, or to organ dysfunctions, etc. Conversely, the attending physician would also know to adjust treatment to higher levels if the clinical response were not adequate (in light of or precluding toxicity aspects). The magnitude of an administered dose in the management of the disorder of interest can vary with the severity of the condition to be treated and to the route of administration. The severity of the condition may, for example, be evaluated, in part, by standard prognostic evaluation methods. Further, the dose and perhaps dose frequency, can also vary according to circumstances, e.g. the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995) and elsewhere in the art. Suitable routes may include, for example, oral, rectal, transdermal, vaginal, transmucosal, or intestinal administration; parenteral delivery, including intramuscular, subcutaneous, or intramedullary injections, as well as intraocular, intrathecal, intravenous, or intraperitoneal administration.

For injection or other routes, agents of the invention may be formulated in aqueous solutions, preferably in physiologically compatible buffers such as Hanks' solution, Ringer's solution, water for injection, physiological saline buffer, or other solution. For transmucosal administration, penetrants appropriate to the barrier to be permeated can be used in the formulation. Such penetrants are generally known in the art.

Use of pharmaceutically acceptable carriers to formulate the compounds herein disclosed for the practice of the invention into dosages suitable for systemic or other administration is within the scope of the invention. With proper choice of carrier and suitable manufacturing practice, the compositions of the present invention, in particular those formulated as solutions, may be administered parenterally, such as by intravenous injection, or other routes. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, elixirs, solutions, suspensions and the like, e.g. for oral ingestion by a patient to be treated. For other routes, formulations can be prepared for creams, ointments, lotions, and the like.

Agents intended to be administered intracellularly may be administered using techniques well known to those of ordinary skill in the art. For example, such agents may be encapsulated into liposomes, other membrane translocation facilitating moieties, or other targeting moieties; then administered as described above. Liposomes can include spherical lipid bilayers with aqueous interiors. All molecules present in an aqueous solution at the time of liposome formation can be incorporated into the aqueous interior. The liposomal contents are both protected from the external microenvironment and, because liposomes fuse with cell membranes, are efficiently delivered into the cell cytoplasm. Additionally, due to hydrophobicity attributes, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art, especially in light of the disclosure provided herein and other information in the art.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, suspending, granulating, dragee-making, levitating, emulsifying, encapsulating, entrapping, lyophilizing, and other processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are optionally provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

This application incorporates by reference each of the following applications in entirety for all purposes: U.S. Provisional Application Ser. 60/684,807 filed May 26, 2005 inventors Paul J. Hergenrother, Karson S. Putt, Grace W. Chen, Jennifer M. Pearson; U.S. Provisional Application Ser. 60/743,878 filed Mar. 28, 2006 inventors Paul J. Hergenrother, Karson S. Putt, Grace W. Chen, Jennifer M. Pearson; U.S. patent application Ser. No. 11/420,425 filed May 25, 2006 inventors Paul J. Hergenrother, Karson S. Putt, Grace W. Chen, Jennifer M. Pearson; PCT International Application Serial PCT/US 06/020910 filed May 26, 2006 inventors Paul J. Hergenrother, Karson S. Putt, Grace W. Chen, Jennifer M. Pearson; PCT International Application Number PCT/US2008/061510 filed Apr. 25, 2008 inventors Paul J. Hergenrother, Karson S. Putt, Joseph S. Sandhorst, Quinn P. Peterson, and Valerie Fako; U.S. provisional application Ser. 60/914,592 filed Apr. 27, 2007 inventors Paul J. Hergenrother; Karson S. Putt; Joseph S. Sandhorst; Quinn P. Peterson; Valerie Fako. U.S. patent application Ser. No. 12/597,287, filed Oct. 23, 2009. Compounds claimed as compositions of matter in patent applications listed herein having an identical inventor to the present application are not intended to be claimed as compositions of matter in the present application and it is intended that sufficient disclosure be present in the present application to be able to exclude each compound from the claims individually or in combination.

STATEMENTS REGARDING INCORPORATION BY REFERENCE AND VARIATIONS

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive. For clarification, as used herein "comprising" is synonymous with "having," "including," "containing," or "characterized by," and is inclusive or open-ended and does not exclude additional, unrecited elements or method steps. As used herein, "consisting of" excludes any element, step, component, or ingredient not specified in the claim element. As used herein, "consisting essentially of" does not exclude materials or steps that do not materially affect the basic and novel characteristics of the claim (e.g., not affecting an active ingredient). In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

The invention has been described with reference to various specific and preferred embodiments and techniques. However, it should be understood that many variations and modifications may be made while remaining within the spirit and scope of the invention. It will be appreciated by one of ordinary skill in the art that compositions, methods, devices, device elements, materials, optional features, procedures and techniques other than those specifically described herein can be applied to the practice of the invention as broadly disclosed herein without resort to undue experimentation. All art-known functional equivalents of compositions, methods, devices, device elements, materials, procedures and techniques described herein; and portions thereof; are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation. The scope of the invention shall be limited only by the claims.

REFERENCES

U.S. Provisional Application Ser. 60/684,807 filed May 26, 2005; U.S. Provisional Application Serial 60743878 filed Mar. 28, 2006; U.S. patent application Ser. No. 11/420,425 filed May 25, 2006 (published as US 20070049602, Mar. 1, 2007); PCT International Application Serial PCT/US 06/020910 filed May 26, 2006 (published as WO2006/ 128173, 30 Nov. 2006), which are incorporated by reference herein, relate to the subject matter of the present application.

These applications are particularly incorporated by reference in entirety: U.S. Provisional Patent Application No. 60/516,556 by Hergenrother et al., filed Oct. 30, 2003; U.S. Provisional Patent Application No. 60/603,246 by Hergenrother et al., filed Aug. 20, 2004; U.S. Ser. No. 10/976,186 by Hergenrother et al., filed Oct. 27, 2004.

U.S. Provisional Application Ser. 60/684,807 filed May 26, 2005; U.S. Provisional Application Serial 60743878 filed Mar. 28, 2006; U.S. patent application Ser. No. 11/420,425 filed May 25, 2006; PCT International Application Serial PCT/US 06/020910 filed May 26, 2006; U.S. Provisional Application Ser. 60/914,592 filed Apr. 27, 2007.

U.S. Pat. No. 6,762,045 Membrane derived caspase-3, compositions comprising the same and methods of use therefore; U.S. Pat. No. 6,534,267 Polynucleotides encoding activators of caspases; U.S. Pat. No. 6,403,765 Truncated Apaf-1 and methods of use thereof; U.S. Pat. Nos. 6,303,329; 6,878, 743 by Choong, et al. issued Apr. 12, 2005; US 20040077542 by Wang, Xiaodong; et al., published Apr. 22, 2004; US 20040180828 by Shi, Yigong, published Sep. 16, 2004.

Slee E A et al., Benzyloxycarbonyl-Val-Ala-Asp (OMe) fluoromethylketone (Z-VAD.FMK) inhibits apoptosis by blocking the processing of CPP32, Biochem J. 1996 Apr. 1; 315 (Pt 1):21-4.

1. Papadopoulos, N., Kinzler, K. W. & Vogelstein, B. The role of companion diagnostics in the development and use of mutation-targeted cancer therapies. Nat Biotechnol 24, 985-95 (2006).
2. Vogelstein, B. & Kinzler, K. W. Cancer genes and the pathways they control. Nat Med 10, 789-99 (2004).
3. Druker, B. J. et al. Effects of a selective inhibitor of the Abl tyrosine kinase on the growth of Bcr-Abl positive cells. Nat Med 2, 561-6 (1996).
4. Ciardiello, F. et al. Antitumor Effect and Potentiation of Cytotoxic Drugs Activity in Human Cancer Cells by ZD-1839 (Iressa), an Epidermal Growth Factor Receptor-selective Tyrosine Kinase Inhibitor. Clinical Cancer Research 6, 2053-2063 (2000).
5. Sala, E. et al. BRAF silencing by short hairpin RNA or chemical blockade by PLX$^{4032}$ leads to different responses in melanoma and thyroid carcinoma cells. Mol Cancer Res 6, 751-9 (2008).
6. Salerno, P. et al. Cytostatic Activity of Adenosine Triphosphate-Competitive Kinase Inhibitors in BRAF Mutant Thyroid Carcinoma Cells. J Clin Endocrinol Metab (2009).
7. Hanahan, D. & Weinberg, R. A. The hallmarks of cancer. Cell 100, 57-70 (2000).
8. Igney, F. H. & Krammer, P. H. Death and anti-death: tumor resistance to apoptosis. Nature Rev. Cancer 2, 277-288 (2002).
9. Zornig, M., Hueber, A.-O., Baum, W. & Evan, G. Apoptosis regulators and their role in tumorigenesis. Biochim. Biophys. Acta 1551, F1-F37 (2001).
10. Fesik, S. W. Promoting apoptosis as a strategy for cancer drug discovery. Nat Rev Cancer 5, 876-885 (2005).
11. Vassilev, L. T. et al. In vivo activation of the p53 pathway by small-molecule antagonists of MDM2. Science 303, 844-848 (2004).
12. Tovar, C. et al. Small-molecule MDM2 antagonists reveal aberrant p53 signaling in cancer: Implications for therapy. Proc. Natl. Acad. Sci. USA 103, 1888-1893 (2006).
13. Oltersdorf, T. et al. An inhibitor of Bcl-2 family proteins induces regression of solid tumours. Nature 435, 677-681 (2005).
14. Li, L. et al. A small molecule Smac mimic potentiates TRAIL- and TNFalpha-mediated cell death. Science 305, 1471-1474 (2004).
15. Sun, H. et al. Design of small-molecule peptidic and nonpeptidic Smac mimetics. Acc. Chem. Res. 41, 1264-1277 (2008).
16. O'Donovan, N. et al. Caspase 3 in breast cancer. Clin Cancer Res 9, 738-42 (2003).
17. Roy, S. et al. Maintenance of caspase-3 proenzyme dormancy by an intrinsic "safety catch" regulatory tripeptide. Proc. Natl. Acad. Sci. 98, 6132-6137 (2001).
18. Krepela, E., Prochazka, J., Liul, X., Fiala, P. & Kinkor, Z. Increased expression of Apaf-1 and procaspase-3 and the functionality of intrinsic apoptosis apparatus in non-small cell lung carcinoma. Biol Chem 385, 153-68 (2004).
19. Izban, K. F. et al. Characterization of the interleukin-1 J3-converting enzyme/Ced-3-family protease, caspase-3/ CPP32, in Hodgkin's disease. Am. J. Pathol. 154, 1439-1447 (1999).
20. Nakagawara, A. et al. High levels of expression and nuclear localization of interleukin-1 β converting enzyme (ICE) and CPP32 in favorable human neuroblastomas. Cancer Res. 57, 4578-4584 (1997).
21. Fink, D. et al. Elevated procaspase levels in human melanoma. Melanoma Res 11, 385-393 (2001).
22. Persad, R. et al. Overexpression of caspase-3 in hepatocellular carcinomas. Mod Pathol. 17, 861-867 (2004).
23. Putt, K. S. et al. Small-molecule activation of procaspase-3 to caspase-3 as a personalized anticancer strategy. Nat Chem Biol 2, 543-550 (2006).
24. Peterson, Q. P. et al. PAC-1 Activates Procaspase-3 in Vitro through Relief of Zinc-Mediated Inhibition. J Mol Biol 388, 144-158 (2009).
25. Peterson, Q. P. et al. Procaspase-3 Activation as an Anti-Cancer Strategy: Structure-Activity Relationship of PAC-1, and its Cellular Co-Localization with Procaspase-3. J Med Chem 52, 5721-5731 (2009).
26. Paoloni, M. & Khanna, C. Translation of new cancer treatments from pet dogs to humans. Nat Rev Cancer 8, 147-156 (2008).
27. María-Isabel, D. et al. Neural Overexcitation and Implication of NMDA and AMPA Receptors in a Mouse Model of Temporal Lobe Epilepsy Implying Zinc Chelation. Epilepsia 47, 887-899 (2006).
28. Domnguez, M. I., Blasco-Ibez, J. M., Crespo, C., Marqus-Mar, A. I. & Martnez-Guijarro, F. J. Zinc chelation during 29. Clark, D. E. In silico prediction of blood-brain barrier permeation. Drug Discov Today 8, 927-33 (2003).
30. Lavoie, N. et al. Extracellular chelation of zinc does not affect hippocampal excitability and seizure-induced cell death in rats. J Physiol 578, 275-89 (2007).
31. Huang, S., Clark, R. J. & Zhu, L. Highly sensitive fluorescent probes for zinc ion based on triazolyl-containing tetradentate coordination motifs. Org. Lett. 9, 4999-5002 (2007).
32. Bose, K., Pop, C., Feeney, B. & Clark, A. G. An uncleavable procaspase-3 mutant has a lower catalytic efficiency but an active site similar to that of mature caspase-3. Biochemistry 42, 12298-12310 (2003).
33. Vichai, V. & Kirtikara, K. Sulforhodamine B colorimetric assay for cytotoxicity screening. Nat. Protocols 1, 1112-1116 (2006).
34. Zalupski, M. et al. Phase III Comparison of Doxorubicin and Dacarbazine Given by Bolus Versus Infusion in Patients With Soft-Tissue Sarcomas: A Southwest Oncology Group Study. J. Natl. Cancer Inst. 83, 926-932 (1991).
35. Tagawa, M. et al. Low-dose cytosine arabinoside regimen induced a complete remission with normal karyotypes in a case with hypoplastic acute myeloid leukaemia with No. 8-trisomy: in vitro and in vivo evidence for normal haematopoietic recovery. Br J Haematol 60, 449-55 (1985).
36. Anderson, H., Thatcher, N., Walling, J. & Hansen, H. A phase I study of a 24 hour infusion of gemcitabine in previously untreated patients with inoperable non-small-cell lung cancer. Br J Cancer 74, 460-2 (1996).
37. Satoh, T. et al. Phase I study of YM155, a novel survivin suppressant, in patients with advanced solid tumors. Clin. Cancer Res. 15, 3872-3880 (2009).
38. Breen, M. & Modiano, J. F. Evolutionarily conserved cytogenetic changes in hematological malignancies of dogs and humans—man and his best friend share more than companionship. Chromosome Res 16, 145-54 (2008).
39. Dorn, C. R., Taylor, D. O. & Schneider, R. The epidemiology of canine leukemia and lymphoma. Bibl Haematol, 403-15 (1970).
40. Kahl, B. Chemotherapy combinations with monoclonal antibodies in non-Hodgkin's lymphoma. Semin Hematol 45, 90-4 (2008).
41. Garrett, L. D., Thamm, D. H., Chun, R., Dudley, R. & Vail, D. M. Evaluation of a 6-month chemotherapy protocol with no maintenance therapy for dogs with lymphoma. J Vet Intern Med 16, 704-9 (2002).
42. Chun, R., Garrett, L. D. & Vail, D. M. Evaluation of a high-dose chemotherapy protocol with no maintenance therapy for dogs with lymphoma. J Vet Intern Med 14, 120-4 (2000).
43. Rassnick, K. M. et al. MOPP chemotherapy for treatment of resistant lymphoma in dogs: a retrospective study of 117 cases (1989-2000). J Vet Intern Med 16, 576-80 (2002).
44. Veterinary Co-operative Oncology Group—Common Terminology Criteria for Adverse Events (VCOG-CTCAE) following chemotherapy or biological antineoplastic therapy in dogs and cats v1.0. Vet Comp Oncol 2, 195-213 (2004).
45. Padhani, A. R. & Ollivier, L. The RECIST (Response Evaluation Criteria in Solid Tumors) criteria: implications for diagnostic radiologists. Br J Radiol 74, 983-6 (2001).
46. Frederickson, C. J., Koh, J.-Y. & Bush, A. I. The neurobiology of zinc in health and disease. Nat Rev Neurosci 6, 449-462 (2005).
47. Karakas, E., Simorowski, N. & Furukawa, H. Structure of the zinc-bound amino-terminal domain of the NMDA receptor NR2B subunit. EMBO J. 28, 3910-3920 (2009).
48. Adler, M., Dinterman, R. E. & Wannemacher, R. W. Protection by the heavy metal chelator N,N,N',N'-tetrakis (2-pyridylmethyl)ethylenediamine (TPEN) against the lethal action of botulinum neurotoxin A and B. Toxicon 35, 1089-1100 (1997).
49. Khanna, C. et al. The dog as a cancer model. Nat Biotechnol 24, 1065-6 (2006).
50. Franklin, R. B., Milon, B., Feng, P. & Costello, L. C. Zinc and zinc transporters in normal prostate and the pathogenesis of prostate cancer. Front Biosci 10, 2230-2239 (2005).
51. Beyersmann, D. & Haase, H. Functions of zinc in signaling, proliferation and differentiation of mammalian cells. BioMetals 14, 331-341 (2001).
52. Aiuchi, T. et al. Zinc ions prevent processing of caspase-3 during apoptosis induced by geranylgeraniol in HL-60 cells. J. Biochem. (Tokyo) 124, 300-303 (1998).
53. Chai, F., Truong-Tran, A. Q., Ho, L. H. & Zalewski, P. D. Regulation of caspase activation and apoptosis by cellular zinc fluxes and zinc deprivation: A review. Immunol. Cell Biol. 77, 272-278 (1999).
54. Chimienti, F., Seve, M., Richard, S., Mathieu, J. & Favier, A. Role of cellular zinc in programmed cell death: temporal relationship between zinc depletion, activation of caspases, and cleavage of Sp family transcription factors. Biochem. Pharmacol. 62, 51-62 (2001).
55. Huesca, M. et al. A novel small molecule with potent anticancer activity inhibits cell growth by modulating intracellular labile zinc homeostasis. Molecular Cancer Therapeutics 8, 2586-2596 (2009).
Huang, S.; Clark, R. J.; Zhu, L., Highly Sensitive Fluorescent Probes for Zinc Ion Based on Triazolyl-Containing Tetradentate Coordination Motifs. Org. Lett. 2007, 9, 4999-5002. Patton, C.; Thompson, S.; Epel, D., Some precautions in using chelators to buffer metals in biological solutions. Cell Calcium 2004, 35, 427-431.
Naganawa, A.; Matsui, T.; Ima, M.; Saito, T.; Murota, M.; Aratani, Y.; Kijima, H.; Yamamoto, H.; Maruyama, T.; Ohuchida, S.; Nakaia, H.; Todaaet, M., Further optimization of sulfonamide analogs as EP1 receptor antagonists: synthesis and evaluation of bioisosteres for the carboxylic acid group. Bioorg Med Chem 2006, 14, 7121-7137.
Putt, K. S.; Chen, G. W.; Pearson, J. M.; Sandhorst, J. S.; Hoagland, M. S.; Kwon, J.-T.; Hwang, S.-K.; Jin, H.; Churchwell, M. I.; Cho, M.-H.; Doerge, D. R.; Helferich, W. G.; Hergenrother, P. J., Small molecule activation of procaspase-3 to caspase-3 as a personalized anticancer strategy. Nature Chem Biol 2006, 2, 543-550. Dauzonne, D.; Folléas, B.; Martinez, L.; Chabot, G. G., Synthesis and in vitro cytotoxicity of a series of 3-aminoflavones. European Journal of Medicinal Chemistry 1997, 32, (1), 71-82.
Hanahan, D. & Weinberg, R. A. The hallmarks of cancer. Cell 100, 57-70 (2000).
Okada, H. & Mak, T. W. Pathways of apoptotic and non-apoptotic death in tumour cells. Nature Rev. Cancer 4, 592-603 (2004).
Roy, S. et al. Maintenance of caspase-3 proenzyme dormancy by an intrinsic "safety catch" regulatory tripeptide. Proc. Natl. Acad. Sci. 98, 6132-6137 (2001).
Svingen, P. A. et al. Components of the cell death machine and drug sensitivity of the National Cancer Institute Cell Line Panel. Clin. Cancer Res. 10, 6807-6820 (2004).
Lowe, S. W., Cepero, E. & Evan, G. Intrinsic tumor suppression. Nature 432, 307-315 (2004).

Vogelstein, B. & Kinzler, K. W. Achilles' heel of cancer. Nature 412, 865-866 (2001).

Traven, A., Huang, D. C. & Lithgow, T. Protein hijacking: key proteins held captive against their will. Cancer Cell 5, 107-108 (2004).

Soengas, M. S. et al. Inactivation of the apoptosis effector Apaf-1 in malignant melanoma. Nature 409, 207-211 (2001).

Wajant, H. Targeting the FLICE inhibitory protein (FLIP) in cancer therapy. Mol. Interv. 3, 124-127 (2003).

Denicourt, C. & Dowdy, S. F. Targeting apoptotic pathways in cancer cells. Science 305, 1411-1413 (2004).

Vassilev, L. T. et al. In vivo activation of the p53 pathway by small-molecule antagonists of MDM2. Science 303, 844-848 (2004).

Degterev, A. et al. Identification of small-molecule inhibitors of interaction between the BH3 domain and Bcl-XL. Nature Cell Biol. 3, 173-182 (2001).

Becattini, B. et al. Rational design and real time, in-cell detection of the proapoptotic activity of a novel compound targeting Bcl-XL. Chem. Biol. 11, 389-395 (2004).

Wang, J.-L. et al. Structure-based discovery of an organic compound that binds Bcl-2 protein and induces apoptosis of tumor cells. Proc. Natl. Acad. Sci. 97, 7124-7129 (2000).

Li, L. et al. A small molecule Smac mimic potentiates TRAIL- and TNFa-mediated cell death. Science 305, 1471-1474 (2004).

Nguyen, J. T. & Wells, J. A. Direct activation of the apoptosis machinery as a mechanism to target cancer cells. Proc. Natl. Acad. Sci. U.S.A. 100, 7533-7538 (2003).

Jiang, X. et al. Distinctive roles of PHAP proteins and prothymosin-α in a death regulatory pathway. Science 299, 223-226 (2003).

Boatright, K. M. & Salvesen, G. S. Mechanisms of caspase activation. Curr. Opin. Cell. Biol. 15, 725-731 (2003).

Nakagawara, A. et al. High levels of expression and nuclear localization of interleukin-1 β converting enzyme (ICE) and CPP32 in favorable human neuroblastomas. Cancer Res. 57, 4578-4584 (1997).

Izban, K. F. et al. Characterization of the interleukin-1 β-converting enzyme/Ced-3-family protease, caspase-3/CPP32, in Hodgkin's disease. Am. J. Pathol. 154, 1439-1447 (1999).

Persad, R. et al. Overexpression of caspase-3 in hepatocellular carcinomas. Modern Patholo. 17, 861-867 (2004).

Pop, C., Feeney, B., Tripathy, A. & Clark, A. C. Mutations in the procaspase-3 dimer interface affect the activity of the zymogen. Biochemistry 42, 12311-12320 (2003).

Stennicke, H. R. et al. J. Biol. Chem. 273, 27084-27090 (1998).

Denault, J.-B. & Salvesen, G. S. Human caspase-7 activity and regulation by its N-terminal peptide. J. Biol. Chem. 278, 34042-24050 (2003).

Putt, K. S., Beilman, G. J. & Hergenrother, P. J. Direct quantitation of Poly(ADP-ribose) polymerase (PARP) activity as a means to distinguish necrotic and apoptotic death in cell and tissue samples. ChemBioChem 6, 53-55 (2005).

Liang, Y., Nylander, K. D., Yan, C. & Schor, N. F. Role of caspase 3-dependent Bcl-2 cleavage in potentiation of apoptosis by Bcl-2. Mol. Pharmacol. 61, 142-149 (2002).

Fujita, N., Nagahshi, A., Nagashima, K., Rokudai, S. & Tsuruo, T. Acceleration of apoptotic cell death after the cleavage of Bcl-XL protein by caspase-3-like proteases. Oncogene 17, 1295-1304 (1998).

Earnshaw, W. C., Martins, L. M. & Kaufmann, S. H. Mammalian caspases: structure, activation, substrates, and functions during apoptosis. Annu. Rev. Biochem. 68, 383-424 (1999).

Koty, P. P., Zhang, H. & Levitt, M. L. Antisense bcl-2 treatment increases programmed cell death in non-small cell lung cancer cell lines. Lung Cancer 23, 115-127 (1999).

National Center for Biotechnology Information (NCBI) Database of the National Library of Medicine/National Institutes of Health (NIH) website: http://www.ncbi.nlm.nih.gov/using the Gene database to search for CASP3 (caspase 3, apoptosis-related cysteine protease [Homo sapiens] GeneID: 836 Locus tag: HGNC:1504; MIM: 600636 updated 15 May 2005. Other Aliases: HGNC: 1504, APOPAIN, CPP32, CPP32B, SCA-1; Other Designations: Human procaspase3 coding sequence; PARP cleavage protease; SREBP cleavage activity 1; Yama; caspase 3; cysteine protease CPP32).

Hergenrother P J. Obtaining and screening compound collections: a user's guide and a call to chemists. Curr Opin Chem. Biol. 2006

Silverman S K, Hergenrother P J. Combinatorial chemistry and molecular diversity Tools for molecular diversification and their applications in chemical biology. Curr Opin Chem. Biol. 2006.

Goode D R, Sharma A K, Hergenrother P J. Using peptidic inhibitors to systematically probe the S1' site of caspase-3 and caspase-7. Org. Lett. 2005 Aug. 4; 7(16):3529-32. PMID: 16048334

Dothager R S, Putt K S, Allen B J, Leslie B J, Nesterenko V, Hergenrother P J. Synthesis and identification of small molecules that potently induce apoptosis in melanoma cells through G1 cell cycle arrest. J Am Chem. Soc. 2005 Jun. 22; 127(24):8686-96. PMID: 15954774

Putt K S, Hergenrother P J. A nonradiometric, high-throughput assay for poly(ADP-ribose) glycohydrolase (PARG): application to inhibitor identification and evaluation. Anal Biochem. 2004 Oct. 15; 333(2):256-64. PMID: 15450800

Putt K S, Hergenrother P J. An enzymatic assay for poly (ADP-ribose) polymerase-1 (PARP-1) via the chemical quantitation of NAD(+): application to the high-throughput screening of small molecules as potential inhibitors. Anal Biochem. 2004 Mar. 1; 326(1):78-86. PMID: 14769338

Nesterenko V, Putt K S, Hergenrother P J. Identification from a combinatorial library of a small molecule that selectively induces apoptosis in cancer cells. J Am Chem. Soc. 2003 Dec. 3; 125(48):14672-3. PMID: 14640619

Putt, Karsone et al., Small scale activation of procaspase-3 as a personalized anticancer strategy, Nature Chemical Biology 2(10):543-550, S543/1-S543/29 (2006).

Peterson, J. Mol. Biol. 2009, 388, 144-158.

Charkoudian, J. Am. Chem. Soc., 2006, 128, 12424-12425.

Peterson, J. Med. Chem., 2009, 52, 5721-5731.

We claim:

1. A compound having formula (FX1):

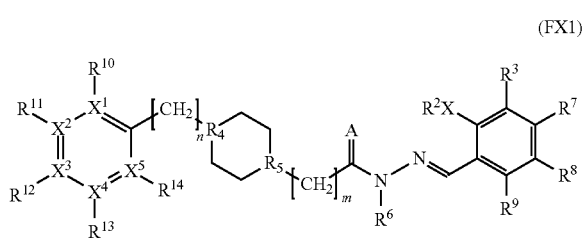

(FX1)

wherein $X^1$, $X^2$, $X^3$, $X^4$, and $X^5$ are each independently C or N, wherein when $X^1$, $X^2$, $X^3$, $X^4$, or $X^5$ is N, the corresponding $R^{10}$, $R^{11}$, $R^{12}$, $R^{13}$, or $R^{14}$ is absent;

one of $R^{10}$, $R^{11}$, $R^{12}$, $R^{13}$, and $R^{14}$ is

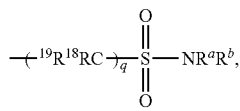

where $R^a$ and $R^b$ are each independently selected from the group consisting of hydrogen, C1-C6 alkyl, and C1-C6 alkoxy; $R^{18}$ and $R^{19}$ are each independently selected from the group consisting of hydrogen and C1-C6 alkyl; and q is an integer from 0 to 3;

$R^7$, $R^8$, and $R^9$, and the others of $R^{10}$, $R^{11}$, $R^{12}$, $R^{13}$, and $R^{14}$, are each independently selected from the group consisting of: hydrogen, halogen, a hydroxyl group, a sulfonamide group, a nitro group, an amino group, a carboxylate group, a sulfonyl group, an aryl sulfonyl group, C1-C6 alkyl, C1-C6 alkoxy, and C2-C6 alkenyl;

$R^3$ is methoxy or allyl;

n and m are each independently integers from 1 to 3;

$R_4$ and $R_5$ are each independently CH or N;

A is O or S;

$R^6$ is hydrogen or $C_1$-$C_6$ alkyl;

X is oxygen; and $R^2$ is hydrogen or C1-C6 alkyl.

2. The compound of claim 1 having formula (FX1):

wherein the others of $R^{10}$, $R^{11}$, $R^{12}$, $R^{13}$, and $R^{14}$ are each independently selected from the group consisting of: hydrogen, halogen, a hydroxyl group, a sulfonamide group, a nitro group, an amino group, a carboxylate group, a sulfonyl group, an aryl sulfonyl group, and C1-C6 alkoxy; and $R^7$, $R^8$, and $R^9$ are each independently selected from hydrogen, halogen, C1-C6 alkyl, C1-C6 alkoxy or C2-C6 alkenyl.

3. The compound of claim 1, wherein $R^2$ is hydrogen.

4. A compound having formula (FX1):

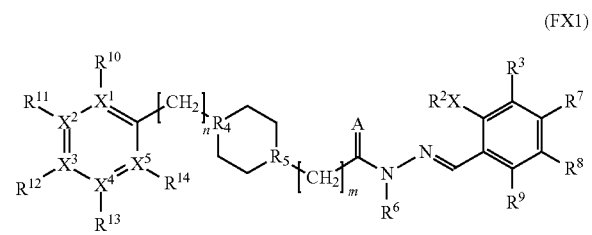

(FX1)

wherein $X^1$, $X^2$, $X^3$, $X^4$, and $X^5$ are each independently C or N, wherein when $X^1$, $X^2$, $X^3$, $X^4$, or $X^5$ is N, the corresponding $R^{10}$, $R^{11}$, $R^{12}$, $R^{13}$, or $R^{14}$ is absent;

$R^{10}$, $R^{11}$, $R^{13}$, $R^{14}$, $R^3$, $R^7$, $R^8$, and $R^9$ are each independently selected from the group consisting of: hydrogen, halogen, a hydroxyl group, a sulfonamide group, a nitro group, an amino group, a carboxylate group, a sulfonyl group, an aryl sulfonyl group, C1-C6 alkyl, C1-C6 alkoxy, and C2-C6 alkenyl;

$R^{12}$ is

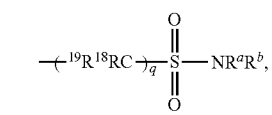

where $R^a$ and $R^b$ are each independently selected from the group consisting of hydrogen, C1-C6 alkyl, and C1-C6 alkoxy; $R^{18}$ and $R^{19}$ are each independently selected from the group consisting of hydrogen and C1-C6 alkyl; and q is an integer from 0 to 3;

n and m are each independently integers from 1 to 3;

$R_4$ and $R_5$ are each independently CH or N;

A is O or S;

$R^6$ is hydrogen or $C_1$-$C_6$ alkyl;

X is oxygen; and $R^2$ is hydrogen or C1-C6 alkyl.

5. The compound of claim 4, wherein $R^a$ and $R^b$ are each hydrogen and q is 0.

6. The compound of claim 4, wherein $R^3$ is allyl, and $R^2$ is hydrogen.

7. The compound of claim 1, wherein one, two or three of $R^{11}$, $R^{12}$, and $R^{13}$ are methoxy.

8. The compound of claim 1, wherein $R^3$ is allyl, and $R^2$ is hydrogen.

9. The compound of claim 1, wherein one or two of $X^1$, $X^2$, $X^3$, $X^4$, and $X^5$ are N.

10. The compound of claim 1, which includes a fluorescent label.

11. A medicament comprising an effective amount of one or more compounds of claim 1 and a pharmaceutical carrier or excipient.

12. The compound of claim 4, wherein $R^a$ and $R^b$ are each hydrogen; q is 0; $R^3$ is allyl; and $R^2$ is hydrogen.

13. The compound of claim 4 that has the structure:

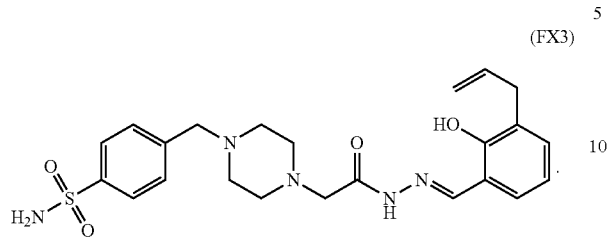

(FX3)

14. A pharmaceutical composition comprising the compound of claim 4 and a pharmaceutical carrier or excipient.

15. A pharmaceutical composition comprising the compound of claim 12 and a pharmaceutical carrier or excipient.

16. A pharmaceutical composition comprising the compound of claim 13 and a pharmaceutical carrier or excipient.

* * * * *